US011771758B2

(12) United States Patent
Backman et al.

(10) Patent No.: US 11,771,758 B2
(45) Date of Patent: Oct. 3, 2023

(54) COMPOSITIONS INCLUDING SBI ADJUVANTS AND METHODS OF USE THEREOF

(71) Applicant: Helix Nanotechnologies, Inc., Walnut, CA (US)

(72) Inventors: Kyle Backman, Arlington, MA (US); Nikhil Dhar, Boston, MA (US); Nikolai Eroshenko, Boston, MA (US); Taylor Gill, Cambridge, MA (US); Kemo Jammeh, Cambridge, MA (US); Marianna Keaveney, Walpole, MA (US); Justin Quinn, Malden, MA (US); Hannu Rajaniemi, Point Richmond, CA (US); Everett Webster, North Andover, MA (US)

(73) Assignee: Helix Nanotechnologies, Inc., Boston, MA (US)

( * ) Notice: Subject to any disclaimer, the term of this patent is extended or adjusted under 35 U.S.C. 154(b) by 0 days.

(21) Appl. No.: 17/685,717

(22) Filed: Mar. 3, 2022

(65) Prior Publication Data

US 2022/0362373 A1 Nov. 17, 2022

Related U.S. Application Data

(60) Provisional application No. 63/156,860, filed on Mar. 4, 2021.

(51) Int. Cl.

| | |
|---|---|
| ***C07K 14/47*** | (2006.01) |
| ***A61K 39/215*** | (2006.01) |
| ***C07K 14/11*** | (2006.01) |
| ***C07K 14/165*** | (2006.01) |
| ***C07K 14/31*** | (2006.01) |
| *A61K 39/00* | (2006.01) |

(52) U.S. Cl.

CPC ............ *A61K 39/215* (2013.01); *C07K 14/11* (2013.01); *C07K 14/165* (2013.01); *C07K 14/31* (2013.01); *C07K 14/472* (2013.01); *A61K 2039/575* (2013.01)

(58) Field of Classification Search

None

See application file for complete search history.

(56) References Cited

U.S. PATENT DOCUMENTS

2019/0282683 A1 9/2019 Van Den Elsen et al.

FOREIGN PATENT DOCUMENTS

| | | | |
|---|---|---|---|
| WO | WO-2007/138328 | A2 | 12/2007 |
| WO | WO-2012/042213 | A1 | 4/2012 |
| WO | WO-2018/096089 | A1 | 5/2018 |
| WO | WO-2022/187424 | A1 | 9/2022 |

OTHER PUBLICATIONS

Almansoor (Development of vaccine conjugates based on Dengue virus using staphylococcal immune evasion protein, 2017, p. 1-66).*

Amanat, F. et al., A serological assay to detect SARS-CoV-2 seroconversion in humans, Nat Med, 26:1033-1036 (2020).

Burman, J. D. et al., Interaction of Human Complement with Sbi. a Staphylococcal Immunoglobulin-binding Protein: Indications of a Novel Mechanism of Complement Evasion by *Staphylococcus aureus**, J. Biol. Chem; 283:17579-17593 (2008).

Clark, E. A. et al., A structural basis for Staphylococcal complement subversion: X-ray structure of the complement-binding domain of *Staphylococcus aureus* protein Sbi in complex with ligand C3d, Mol Immunol., 48(4): 452-462 (2011).

Nie, J. et al., Quantification of SARS-CoV-2 neutralizing antibody by a pseudotyped virus-based assay, Nat Biotech, 15:3699-3715 (2020).

Raymond, D. D. et al., Conserved epitope on influenza-virus hemagglutinin head defined by a vaccine-induced antibody, PNAS 115(1):168-173 (2018).

Yang, Y. et al., Utilization of Staphylococcal Immune Evasion Protein Sbi as a Novel Vaccine Adjuvant, Frontiers in Immunology, 9(3139):1-17 (2019).

International Search Report for PCT/US22/18610, 9 pages (dated Mar. 6, 2022).

Sun, S. et al., Recombinant Fe-fusion vaccine of RBD induced protection against SARS-CoV-2 in nonhuman primate and mice, bioRxiv, (2020).

Written Opinion for PCT/US22/18610, 13 pages (dated Mar. 6, 2022).

Yang, J. et al., A vaccine targeting the RBD of the S protein of SARS-CoV-2 induces protective immunity, Nature, 586(7830):572-577 (2020).

* cited by examiner

*Primary Examiner* — Agnieszka Boesen

(74) *Attorney, Agent, or Firm* — Choate, Hall & Stewart LLP; Stephanie L. Schonewald; Mandeep Kaur

(57) ABSTRACT

Disclosed herein are fusion polypeptides comprising: (i) a fragment antigen comprising an epitope of a target protein antigen; and (ii) a complement binding polypeptide. The disclosure also provides fusion polynucleotides (e.g., mRNA) encoding the same. Also disclosed herein are methods of making and using the fusion polypeptides and fusion polynucleotides of the present disclosure.

27 Claims, 10 Drawing Sheets

Specification includes a Sequence Listing.

a.

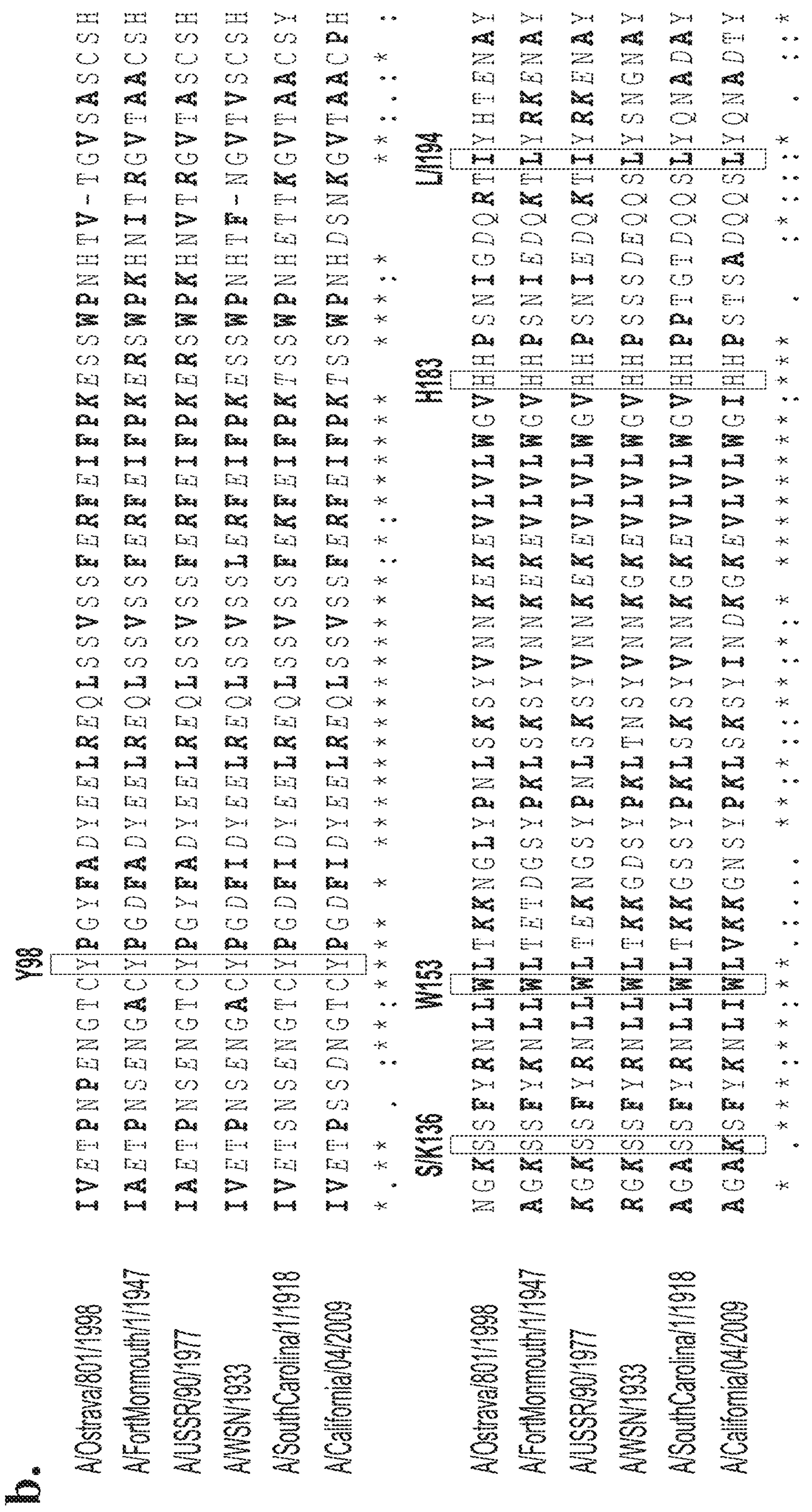

FIG. 7B b.

|  | S/K136 | | Y98 | | | | |
|---|---|---|---|---|---|---|---|
| A/Ostrava/801/1998 | | IVETPNPENGTCYPGYFADYEELREQLSSVSSFERFEIFPKESSWPNHHTV-TGVSASCSH |
| A/FortMonmouth/1/1947 | | IAETPNSENGACYPGYFADYEELREQLSSVSSFERFEIFPKERSWPKHNITRGVTAACSH |
| A/USSR/90/1977 | | IAETPNSENGACYPGYFADYEELREQLSSVSSFERFEIFPKERSWPKHNVTRGVTASCSH |
| A/WSN/1933 | | IVETPNSENGACYPGDFIDYEELREQLSSVSSLERFEIFPKESSWPNHTF-NGVTVSCSH |
| A/SouthCarolina/1/1918 | | IVETSNSENGTCYPGDFIDYEELREQLSSVSSFE

COMPOSITIONS INCLUDING SBI ADJUVANTS AND METHODS OF USE THEREOF

CROSS-REFERENCE TO RELATED APPLICATIONS

This application claims priority to U.S. Provisional Patent Application 63/156,860 filed on Mar. 4, 2021, the entire contents of which is hereby incorporated by reference.

SEQUENCE LISTING

The instant application contains a Sequence Listing which has been submitted electronically in ASCII format and is hereby incorporated by reference in its entirety. Said ASCII copy, created on Apr. 19, 2022, is named 2012611-0035_SL.txt and is 119,138 bytes in size.

BACKGROUND

In recent years, progress has been made in the development of vaccines for a variety of diseases and conditions. However, these efforts have not been able to generate broadly neutralizing vaccines.

SUMMARY

The present disclosure provides compositions for stimulating an immune response against an antigen and/or for enhancing immunogenicity of an antigen. In some embodiments, compositions disclosed herein comprise immunogenic compositions comprising: (1) an antigen fragment or an antigen variant, fused to (2) an adjuvant comprising a complement C3d-binding region. In some embodiments, an immunogenic composition disclosed herein can enhance the titers of the resulting antibody response and/or result in a measurable T cell response. In some embodiments, the adjuvant is or comprises a complement C3d-binding region of a Sbi protein from *Staphylococcus aureus* (e.g., Sbi III and/or Sbi IV). Also provided herein are pharmaceutical compositions and methods of using said pharmaceutical compositions to stimulate an immune response against an antigen and/or to enhance immunogenicity of an antigen.

The present disclosure provides a polypeptide comprising a complement C3d-binding polypeptide from an immunoglobulin-binding protein (Sbi) of *Staphylococcus aureus*. In some embodiments, a polypeptide is a fusion polypeptide comprising: (i) a fragment antigen that comprises an epitope of a target protein antigen; and (ii) a complement C3d-binding polypeptide from an immunoglobulin-binding protein (Sbi) of *Staphylococcus aureus*.

In some embodiments, a complement C3d-binding polypeptide is or comprises one or both of domain III and domain IV of the Sbi of *Staphylococcus aureus*, or a functional fragment or a variant thereof. In some embodiments, a complement C3d-binding polypeptide is or comprises domain III of the Sbi of *Staphylococcus aureus*, or a functional fragment or a variant thereof. In some embodiments, a complement C3d-binding polypeptide is or comprises domain IV of the Sbi of *Staphylococcus aureus*, or a functional fragment or a variant thereof. In some embodiments, a complement C3d-binding polypeptide is or comprises domain III and domain IV of the Sbi of *Staphylococcus aureus*, or a functional fragment or a variant thereof.

In some embodiments, a fragment antigen has an amino acid sequence length of at least 5%, 10%, 20%, 30%, 40%, 50%, 60%, 70%, 80%, 90% or 95% compared to the amino acid sequence length of the target protein antigen. In some embodiments, a fragment antigen has an amino acid sequence length of no more than 50% of the amino acid sequence length of the target protein antigen. In some embodiments, a fragment antigen has an amino acid sequence length of no more than 40%, 30%, 20%, 10% or 5% of the amino acid sequence length of the target protein antigen.

In some embodiments, a fragment antigen has about 10-300 amino acid residues in length. In some embodiments, a fragment antigen has at least 10 amino acid residues in length. In some embodiments, a fragment antigen has less than about 300 amino acid residues in length. In some embodiments, a fragment antigen has about 10-300, 10-250, 10-200, 10-150, 10-100, 10-90, 10-80, 10-70, 10-60, 10-50, 10-40, 10-30, 10-20, 20-300, 30-300, 40-300, 50-300, 60-300, 70-300, 80-300, 90-100, 100-300, 150-300, 200-300, 250-300, 20-250, 30-200, 40-150, 50-100, 60-90, or 70-80 amino acids residues in length. In some embodiments, a fragment antigen has about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 amino acids residues in length.

Also provided herein is a fusion polypeptide comprising: (i) an antigen variant or a fragment antigen variant that comprises an epitope of a target protein antigen; and (ii) a complement C3d-binding polypeptide from an immunoglobulin-binding protein (Sbi) of *Staphylococcus aureus*.

In some embodiments, a complement C3d-binding polypeptide is or comprises one or both of domain III and domain IV of the Sbi of *Staphylococcus aureus*, or a functional fragment or a variant thereof. In some embodiments, a complement C3d-binding polypeptide is or comprises domain III of the Sbi of *Staphylococcus aureus*, or a functional fragment or a variant thereof. In some embodiments, a complement C3d-binding polypeptide is or comprises domain IV of the Sbi of *Staphylococcus aureus*, or a functional fragment or a variant thereof. In some embodiments, a complement C3d-binding polypeptide is or comprises domain III and domain IV of the Sbi of *Staphylococcus aureus*, or a functional fragment or a variant thereof.

In some embodiments, an antigen variant or fragment antigen variant amino acid sequence length is identical to the amino acid sequence length of the target protein antigen.

In some embodiments, an antigen variant or fragment antigen variant comprises at least one modified amino acid compared to the target protein antigen. In some embodiments, a modified amino acid comprises N-linked glycosylation. In some embodiments, an antigen variant or fragment antigen variant comprises at least one amino acid mutation compared to the target protein antigen. In some embodiments, an antigen variant or fragment antigen variant comprises 2, 3, 4, 5, 6, 7, 8, 9, 10, 15, 20, 30, 40 or 50 amino acid mutations compared to the target protein antigen. In some embodiments, the mutation introduces a Serine, a Threonine, an Alanine, or an amino acid at a particular position which is different from the amino acid present at that position in the target protein antigen. In some embodiments, the mutation prevents formation of a disulfide bond.

In some embodiments, a fragment antigen is characterized in that when expressed in vivo, it binds to a Major Histocompatibility Complex (MHC) molecule. In some embodiments, a MHC molecule is or comprises a MHC I molecule or a MHC II molecule.

In some embodiments, a fragment antigen is characterized in that when expressed in vivo, it does not bind to a MHC molecule.

In some embodiments, a fragment antigen is characterized in that when expressed in vivo, it folds into a three-dimensional conformation that is substantially identical to the three-dimensional conformation of the fragment antigen as it is in its native position in the target protein antigen.

In some embodiments, a fragment antigen, antigen variant or fragment antigen variant further comprises an amino acid sequence from a second target protein antigen.

In some embodiments, a target protein antigen is or comprises an infectious disease antigen. In some embodiments, an infectious disease antigen is or comprises a viral antigen, a bacterial antigen, a fungal antigen, or combinations thereof. In some embodiments, a viral antigen is or comprises an influenza antigen. In some embodiments, a viral antigen is or comprises a coronavirus polypeptide. In some embodiments, a coronavirus polypeptide is or comprises a SARS-CoV-2 protein. In some embodiments, a SARS-CoV-2 protein is or comprises a Spike protein (SARS-CoV-2 S) or fragment thereof; an Envelope protein (SARS-CoV-2 E) or fragment thereof; a Membrane protein (SARS-CoV-2 M) or fragment thereof; a nucleocapsid protein (SARS-CoV-2 N) or fragment thereof an accessory factor polypeptide or fragment thereof; or any combination thereof. In some embodiments, a SARS-CoV-2 protein comprises a Spike protein or a fragment thereof (e.g., RBD).

In some embodiments, a target protein antigen is or comprises a cancer antigen.

In some embodiments, a fragment antigen, antigen variant or fragment antigen variant has an amino acid sequence at least 80%, 85%, 90%, 91%, 92%, 93%, 94%, 95%, 96%, 97%, 98%, 99% or 100% identity to the amino acid sequence of SEQ ID NO: 3.

In some embodiments, a fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 4.

In some embodiments, a fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 5.

In some embodiments, a fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 6.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 7.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 20.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 21.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 22.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 23.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 24.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 25.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO:26.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 27.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 28.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 29.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 30.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 31.

In some embodiments, a fragment antigen, antigen variant or fragment antigen variant has at least 80%, 85%, 90%, or 100% identity to the amino acid sequence of SEQ ID NO: 8.

In some embodiments, a complement C3d-binding polypeptide comprises an Sbi domain III having at least 80%, 85%, 90%, 91%, 92%, 93%, 94%, 95%, 96%, 97%, or 100% identity to the amino acid sequence of SEQ ID NO: 9.

In some embodiments, a complement C3d-binding polypeptide comprises an Sbi domain IV having at least 80%, 85%, 90%, 91%, 92%, 93%, 94%, 95%, 96%, 97%, or 100% identity to the amino acid sequence of SEQ ID NO: 10.

In some embodiments, a Sbi domain III and a Sbi domain IV are contiguous.

In some embodiments, a Sbi domain III and a Sbi domain IV are separated by a linker.

In some embodiments, (a) and (b) are encoded by a nucleotide sequence and are disposed in the same nucleotide sequence or in different nucleotide sequences. In some embodiments, (a) is disposed N-terminus of (b). In some embodiments, (a) is disposed C-terminus of (b).

In some embodiments, (a) and (b) are contiguous or separated by a linker. In some embodiments, the linker is a peptidyl linker. In some embodiments, the peptidyl linker comprises at least 60% glycine and/or serine. In some embodiments, the linker is chosen from a Gly-Gly-Gly-Gly-Ser (Gly4-Ser) linker (SEQ ID NO: 60), or a Histidine linker. In some embodiments, the linker is a Gly4-Ser linker (SEQ ID NO: 60). In some embodiments, the linker comprises 1, 2, 3, 4, 5, 6, 7, 8, 9, or 10 repeats of the Gly4-Ser linker (SEQ ID NO: 61). In some embodiments, the linker comprises 3 repeats of the Gly4-Ser linker (SEQ ID NO: 11). In some embodiments, the linker comprises the sequence of SEQ ID NO: 11.

In some embodiments, a fusion polypeptide further comprises a secretion peptide. In some embodiments, the secretion peptide is about 10-30 amino acids in length. In some embodiments, a secretion peptide is about 10, 11, 12, 13, 14, 15, 16, 17, 18, 19, 20, 21, 22, 23, 24, 25, 26, 27, 28, 29 or 30 amino acids in length. In some embodiments, a secretion peptide comprises an amino acid having at least 80%, 85%, 90%, or 100% identity to the amino acid sequence of SEQ ID NO: 1. In some embodiments, a secretion peptide comprises an amino acid having at least 80%, 85%, 90%, or 100% identity to the amino acid sequence of SEQ ID NO: 2.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 12.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 13.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 14.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 15.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 16.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 17.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 18.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 19.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 32.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 33.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 34.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:35.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:36.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:37.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:38.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:39.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:40.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:41.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:42.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 43.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 44.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:45.

In some embodiments, a fusion polypeptide is encoded by a polynucleotide which is or comprises RNA. In some embodiments, a fusion polynucleotide is or comprises messenger RNA.

In some embodiments, a fusion polypeptide is encoded by a polynucleotide which is or comprises DNA.

Disclosed herein is a fusion polynucleotide encoding any one of the fusion polypeptides disclosed herein.

Also disclosed herein is a fusion polynucleotide comprising a nucleotide sequence encoding: (i) a fragment antigen that comprises an epitope of a target protein antigen; and (ii) a complement C3d-binding polypeptide from an immunoglobulin-binding protein (Sbi) of *Staphylococcus aureus.*

Disclosed herein is a polynucleotide comprising a nucleotide sequence encoding: (i) an antigen variant or a fragment antigen variant that comprises an epitope of a target protein antigen; and (ii) a complement C3d-binding polypeptide from an immunoglobulin-binding protein (Sbi) of *Staphylococcus aureus.*

In some embodiments, a fusion polynucleotide is or comprises RNA. In some embodiments, a polynucleotide is or comprises messenger RNA.

In some embodiments, a fusion polynucleotide is or comprises DNA.

In some embodiments, a complement C3d-binding polypeptide encoded by the polynucleotide is or comprises one or both of domain III and domain IV of the Sbi of *Staphylococcus aureus*, or a functional fragment or a variant thereof. In some embodiments, a complement C3d-binding polypeptide encoded by the polynucleotide is or comprises domain III of the Sbi of *Staphylococcus aureus*, or a functional fragment or a variant thereof. In some embodiments, a complement C3d-binding polypeptide encoded by the polynucleotide is or comprises domain IV of the Sbi of *Staphylococcus aureus*, or a functional fragment or a variant thereof. In some embodiments, a complement C3d-binding polypeptide encoded by the polynucleotide is or comprises domain III and domain IV of the Sbi of *Staphylococcus aureus*, or a functional fragment or a variant thereof.

In some embodiments, a fusion polynucleotide encodes a fragment antigen that has an amino acid sequence length of at least 5%, 10%, 20%, 30%, 40%, 50%, 60%, 70%, 80%, 90% or 95% compared to the amino acid sequence length of the target protein antigen. In some embodiments, a fusion polynucleotide encodes a fragment antigen that has an amino acid sequence length of no more than 50% of the amino acid sequence length of the target protein antigen. In some embodiments, a fusion polynucleotide encodes a fragment antigen has an amino acid sequence length of no more than 40%, 30%, 20%, 10% or 5% of the amino acid sequence length of the target protein antigen.

In some embodiments, a fusion polynucleotide encodes an antigen variant or fragment antigen variant having an amino acid sequence length that is identical to the amino acid sequence length of the target protein antigen.

In some embodiments, a fusion polynucleotide encodes an antigen variant or fragment antigen variant which comprises at least one modified amino acid compared to the target protein antigen.

In some embodiments, a fusion polynucleotide encodes a fragment antigen which is characterized in that when expressed in vivo, it binds to a Major Histocompatibility Complex (MHC) molecule. In some embodiments, a MHC molecule is or comprises a MHC I molecule or a MHC II molecule.

In some embodiments, a fusion polynucleotide encodes a fragment antigen which is characterized in that when expressed in vivo, it does not bind to a MHC molecule.

In some embodiments, a fusion polynucleotide encodes a fragment antigen which is characterized in that when expressed in vivo, it folds into a three-dimensional conformation that is substantially identical to the three-dimensional conformation of the fragment antigen as it is in its native position in the target protein antigen.

In some embodiments, a fusion polynucleotide encodes a fragment antigen, antigen variant or fragment antigen variant which further comprises an amino acid sequence from a second target protein antigen.

In some embodiments, a target protein antigen is or comprises an infectious disease antigen. In some embodiments, an infectious disease antigen is or comprises a viral antigen, a bacterial antigen, a fungal antigen, or combinations thereof. In some embodiments, an antigen is or comprises a viral antigen. In some embodiments, a viral antigen is or comprises an influenza antigen. In some embodiments, a viral antigen is or comprises a coronavirus polypeptide. In some embodiments, a coronavirus polypeptide is or comprises a SARS-CoV-2 protein. In some embodiments, a SARS-CoV-2 protein is or comprises a Spike protein (SARS-CoV-2 S) or fragment thereof; an Envelope protein (SARS-CoV-2 E) or fragment thereof; a Membrane protein (SARS-CoV-2 M) or fragment thereof; a nucleocapsid protein (SARS-CoV-2 N) or fragment thereof an accessory factor polypeptide or fragment thereof; or any combination thereof. In some embodiments, the SARS-CoV-2 protein comprises a Spike protein or a fragment thereof (e.g., RBD).

In some embodiments, a target protein antigen is or comprises a cancer antigen.

In some embodiments, (a) is disposed C-terminus of (b). In some embodiments, (a) and (b) are contiguous or separated by a nucleotide sequence encoding a linker. In some embodiments, the linker is a peptidyl linker. In some embodiments, the peptidyl linker comprises at least 60% glycine and/or serine. In some embodiments, the linker is chosen from a Gly-Gly-Gly-Gly-Ser (Gly4-Ser) linker (SEQ ID NO: 60), or a Histidine linker.

In some embodiments, a fusion polynucleotide further comprises a nucleotide sequence encoding a secretion peptide.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 46.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 47.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 48.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 49.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 50.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 51.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 52.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 53.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 54.

Disclosed herein is an expression vector comprising any one of the fusion polynucleotides disclosed herein.

In some embodiments, an expression vector comprises a viral vector. In some embodiments, a viral vector comprises a retrovirus vector, an adenovirus vector, an adeno-associated virus vector or a lentivirus vector or an RNA vector.

Also disclosed herein is a composition for delivering any one of the fusion polypeptides disclosed herein.

Disclosed herein is a composition for delivering any one of the fusion polynucleotides disclosed herein.

This disclosure provides a pharmaceutical composition that delivers a fusion polypeptide disclosed herein, a fusion polynucleotide disclosed herein, or an expression vector comprising a fusion polynucleotide disclosed herein.

In some embodiments, a pharmaceutical composition further comprises a pharmaceutically acceptable excipient, a diluent, or a combination thereof.

Disclosed herein is a method of making comprising: recombinantly joining a first nucleotide sequence that encodes a fragment antigen comprising an epitope of a target protein antigen, and a second nucleotide sequence that encodes a complement C3d-binding polypeptide from a immunoglobulin-binding protein (Sbi) of *Staphylococcus aureus* to form a polynucleotide comprising the first nucleotide sequence and the second nucleotide sequence.

In some embodiments, the method further comprises expressing the polynucleotide in a cell to produce a fusion polypeptide encoded by the polynucleotide.

Disclosed herein is a cell comprising a fusion polypeptide disclosed herein, a fusion polynucleotide disclosed herein, or an expression vector comprising a fusion polynucleotide disclosed herein.

In some embodiments, the cell is contacted with the fusion polynucleotide, fusion polypeptide or expression vector. In some embodiments, contacting occurs in vivo, in vitro or ex vivo.

Disclosed herein is a kit comprising a fusion polypeptide disclosed herein, a fusion polynucleotide disclosed herein, or an expression vector comprising a fusion polynucleotide disclosed herein, and instructions for use.

In some embodiments, the kit further comprises: a polynucleotide comprising a nucleotide sequence that encodes a target protein antigen; or a target protein antigen encoded by the polynucleotide.

The disclosure provides, a method comprising administering to a subject in need thereof at least one dose of a pharmaceutical composition comprising a fusion polypeptide disclosed herein, a fusion polynucleotide disclosed herein, or an expression vector comprising a fusion polynucleotide disclosed herein.

In some embodiments, the at least one dose is administered in an effective amount to induce an immune response against the fragment antigen in the subject.

In some embodiments, the immune response comprises generation of a neutralizing antibody titer against the fragment antigen.

In some embodiments, a neutralizing antibody titer is increased by at least 50%, as compared to a neutralizing antibody titer induced by a fragment antigen in the absence of the complement C3d-binding polypeptide from an immunoglobulin-binding protein (Sbi) of *Staphylococcus aureus*.

In some embodiments, the generation of a neutralizing antibody titer has been established in a mouse model using a dose of at least 0.1 μg.

In some embodiments, the at least one dose is administered in an effective amount to stimulate B cells while reducing induction of T cell response.

Disclosed herein is a method comprising administering to a subject: a first dose of a pharmaceutical composition disclosed herein; and a second dose of a pharmaceutical composition disclosed herein. In some embodiments, a pharmaceutical composition comprises a fusion polypeptide disclosed herein, a fusion polynucleotide disclosed herein, or an expression vector comprising a fusion polynucleotide disclosed herein.

In some embodiments, a first dose and a second dose are administered by at least 3 days, 4 days, 5 days, 6 days, 7 days, 2 weeks, 3 weeks, or 4 weeks apart.

In some embodiments, a first dose and a second dose are in the same amount.

In some embodiments, a first dose and a second dose are in different amounts.

Further disclosed herein is a method comprising: administering to a subject in need thereof a dose of a pharmaceutical composition disclosed herein, such that the subject receives: a first dose of a pharmaceutical composition that delivers a polynucleotide comprising a nucleotide sequence that encodes a target protein antigen or a target protein antigen encoded by the polynucleotide; and a second dose of a pharmaceutical composition disclosed herein.

In some embodiments, (a) the polynucleotide comprising a nucleotide sequence that encodes a target protein antigen further comprises a nucleotide sequence encoding a complement C3d-binding polypeptide from an immunoglobulin-binding protein (Sbi) of *Staphylococcus aureus*; or (b) the target protein antigen encoded by the polynucleotide further comprises a complement C3d-binding polypeptide from an immunoglobulin-binding protein (Sbi) of *Staphylococcus aureus*.

In some embodiments, the method further comprises, prior to the administering step, administering to the subject the first dose of the pharmaceutical composition that delivers a polynucleotide comprising a nucleotide sequence that encodes a target protein antigen or a target protein antigen encoded by the polynucleotide.

This disclosure provides, a method comprising: administering to a subject in need thereof a dose of a pharmaceutical composition disclosed herein, such that the subject receives: a first dose of the pharmaceutical composition of claim disclosed herein, and a second dose of a pharmaceutical composition that delivers a polynucleotide comprising a nucleotide sequence that encodes a target protein antigen or a target protein antigen encoded by the polynucleotide.

In some embodiments, (a) the polynucleotide comprising a nucleotide sequence that encodes a target protein antigen further comprises a nucleotide sequence encoding a complement C3d-binding polypeptide from an immunoglobulin-binding protein (Sbi) of *Staphylococcus aureus*; or (b) the target protein antigen encoded by the polynucleotide further comprises a complement C3d-binding polypeptide from an immunoglobulin-binding protein (Sbi) of *Staphylococcus aureus*.

Disclosed herein is a method comprising: administering to a subject in need thereof a dose of a pharmaceutical composition disclosed herein, such that the subject receives: a first dose of a pharmaceutical composition that delivers a polynucleotide comprising a nucleotide sequence that encodes a fusion polypeptide comprising (i) a target protein antigen and (ii) a complement C3d-binding polypeptide from an immunoglobulin-binding protein (Sbi) of *Staphylococcus aureus*; or a fusion polypeptide encoded by the polynucleotide; and a second dose of the pharmaceutical composition disclosed herein.

In some embodiments, the method further comprises, prior to the administering step, administering to the subject the first dose of the pharmaceutical composition that delivers a polynucleotide comprising a nucleotide sequence that encodes a fusion polypeptide comprising (i) a target protein antigen and (ii) a complement C3d-binding polypeptide from an immunoglobulin-binding protein (Sbi) of *Staphylococcus aureus*; or a fusion polypeptide encoded by the polynucleotide.

In some embodiments, a first dose and a second dose are administered by at least 3 days, 4 days, 5 days, 6 days, 7 days, 2 weeks, 3 weeks, or 4 weeks apart.

In some embodiments of any of the methods disclosed herein, the subject in need thereof is a subject who is suffering from or is susceptible to a disease, disorder, or condition induced by the target protein antigen.

In some embodiments, a subject is a mammalian subject.

In some embodiments, a subject is a human subject.

In some embodiments, administration can be performed by intramuscular administration, intradermal administration, intravenous administration, subcutaneous administration, or combinations thereof.

Disclosed herein is a composition comprising a fusion polypeptide disclosed herein, or a fusion polynucleotide disclosed herein, or a pharmaceutical composition disclosed herein, for use in enhancing the immunogenicity of an antigen.

Also disclosed herein is a composition comprising a fusion polypeptide disclosed herein, or a fusion polynucleotide disclosed herein, or a pharmaceutical composition disclosed herein, for use in stimulating an immune response against an antigen.

Further disclosed herein is a composition comprising a fusion polypeptide disclosed herein, or a fusion polynucleotide disclosed herein, or a pharmaceutical composition disclosed herein, for use in method of treating a disease or ameliorating a symptom of a disease.

This disclosure provides, a method for enhancing the immunogenicity of an antigen, comprising administering to a subject in need thereof, a fusion polypeptide disclosed herein, or a fusion polynucleotide disclosed herein, or a pharmaceutical composition disclosed herein.

This disclosure also provides a method for stimulating an immune response against an antigen, comprising administering to a subject in need thereof, a fusion polypeptide disclosed herein, or a fusion polynucleotide disclosed herein, or a pharmaceutical composition disclosed herein.

Additionally provided herein is a method of treating a disease or ameliorating a symptom of a disease comprising administering to a subject in need thereof, a fusion polypeptide disclosed herein, or a fusion polynucleotide disclosed herein, or a pharmaceutical composition disclosed herein.

This disclosure provides use of a composition comprising a fusion polypeptide disclosed herein, or a fusion polynucleotide disclosed herein, or a pharmaceutical composition disclosed herein in the preparation of a medicament for enhancing the immunogenicity of a fragment antigen.

This disclosure also provides, use of a composition comprising a fusion polypeptide disclosed herein, or a fusion polynucleotide disclosed herein, or a pharmaceutical composition disclosed herein, in the preparation of a medicament for stimulating an immune response against a antigen.

Further provided herein is use of a composition comprising a fusion polypeptide disclosed herein, or a fusion polynucleotide disclosed herein, or a pharmaceutical composition disclosed herein, in the preparation of a medicament for treating a disease or ameliorating a symptom of a disease.

Provided herein is the use of a composition comprising a fusion polypeptide disclosed herein, or a fusion polynucleotide disclosed herein, or a pharmaceutical composition disclosed herein, for enhancing the immunogenicity of a fragment antigen.

Further provided herein is the use of a composition comprising a fusion polypeptide disclosed herein, or a fusion polynucleotide disclosed herein, or a pharmaceutical composition disclosed herein, for stimulating an immune response against a antigen.

This disclosure provides use of a composition comprising a fusion polypeptide disclosed herein, or a fusion polynucleotide disclosed herein, or a pharmaceutical composition disclosed herein, for treating a disease or ameliorating a symptom of a disease.

In some embodiments of any of the methods or uses disclosed herein, the subject is a mammal.

In some embodiments of any of the methods or uses disclosed herein, the subject is a human.

In some embodiments of any of the methods or uses disclosed herein, a single dose of the fusion polypeptide, fusion polynucleotide or pharmaceutical composition is administered.

In some embodiments of any of the methods or uses disclosed herein, a plurality of doses of the fusion polypeptide, fusion polynucleotide or pharmaceutical composition is administered.

In some embodiments of any of the methods or uses disclosed herein, the fusion polypeptide, fusion polynucleotide or pharmaceutical composition is administered at a dose of about 0.5 micrograms to 10 micrograms.

In some embodiments of any of the methods or uses disclosed herein, administration of the fusion polynucleotide, fusion polypeptide or pharmaceutical composition results in a humoral response. In some embodiments, the humoral response is an antibody response.

In some embodiments of any of the methods or uses disclosed herein, administration of the fusion polynucleotide, fusion polypeptide or pharmaceutical composition results in an increased titer of an antibody response. In some embodiments, the increase in titer is an increase of about 10 fold to about 500 fold. In some embodiments, the increased titer of the antibody response is compared to administration of an otherwise similar fusion polynucleotide that does not comprise an Sbi domain III, or a fragment or variant thereof; and Sbi domain IV, or a fragment or a variant thereof. In some embodiments, the increased titer of the antibody response is compared to administration of an otherwise similar fusion polypeptide that does not comprise an Sbi domain III, or a fragment or variant thereof; and an Sbi domain IV, or a fragment or a variant thereof. In some embodiments, the increased titer of the antibody response is compared to administration of an otherwise similar pharmaceutical composition that does not comprise a nucleotide sequence encoding Sbi domain III, or a fragment or variant thereof; and Sbi domain IV, or a fragment or a variant thereof.

In some embodiments of any of the methods or uses disclosed herein, the composition is administered via any one of the following routes of administration: intramuscular, intravenous, subcutaneous, intrathecal, intradermal, ocular, intranasal, sublingual, or oral.

This disclosure provides, an in vitro method of selecting a fragment antigen by identifying a polypeptide fragment that folds into a three-dimensional conformation that is substantially identical to the three-dimensional conformation as in a target protein antigen from which the fragment is derived.

In some embodiments, the method comprises the steps of: providing a mammalian cell display system that displays a library of fragment antigen candidates on cell surface; exposing the mammalian cell display system to a composition comprising antibodies that bind to a target protein antigen from which the fragment antigen candidates are derived; detecting fragment antigen candidates that bind to the target protein antigen-binding antibodies, wherein the binding of a fragment antigen candidate that binds to at least one of the target protein antigen-binding antibodies is indicative of its likelihood to fold into a three-dimensional conformation that is substantially identical to the three-dimensional conformation as in the target protein antigen.

In some embodiments, the method further comprises a step of generating antibodies that bind to the target protein antigen.

In some embodiments, the generation of the antibodies comprises (i) immunizing animals with a target protein antigen or a polynucleotide encoding the same from which the fragment antigen candidates are derived; and (ii) identifying antibodies that bind to the target protein antigen.

In some embodiments, the mammalian cell display system comprises HEK293T cells, HeLa cells, or CHO cells.

In some embodiments, the polypeptide fragment is identified based on binding affinity to the antibody in a serum binding assay or a similar assay.

Also provided herein is a recombinant polynucleotide comprising a nucleotide sequence encoding an immunoglobulin-binding protein (Sbi) of *Staphylococcus aureus*, or a fragment thereof.

In some embodiments, the polynucleotide comprises a sequence encoding a complement C3d-binding polypeptide from Sbi.

In some embodiments, the complement C3d-binding polypeptide is or comprises one or both of domain III and domain IV of the Sbi of *Staphylococcus aureus*, or a functional fragment or a variant thereof.

In some embodiments, the polynucleotide is or comprises RNA. In some embodiments, the polynucleotide is or comprises messenger RNA.

In some embodiments, the polynucleotide is or comprises DNA.

In some embodiments, the polynucleotide encodes a polypeptide which has at least 80%, 85%, 90%, 91%, 92%, 93%, 94%, 95%, 96%, 97%, 98%, 99% or 100% identity to the nucleotide sequence of SEQ ID NO: 9.

In some embodiments, the polynucleotide encodes a polypeptide which has at least 80%, 85%, 90%, 91%, 92%, 93%, 94%, 95%, 96%, 97%, 98%, 99% or 100% identity to the nucleotide sequence of SEQ ID NO: 10.

This disclosure provides an isolated polypeptide comprising an immunoglobulin-binding protein (Sbi) of *Staphylococcus aureus*.

In some embodiments, the polypeptide comprises a complement C3d-binding polypeptide from Sbi.

In some embodiments, the complement C3d-binding polypeptide is or comprises one or both of domain III and domain IV of the Sbi of *Staphylococcus aureus*, or a functional fragment or a variant thereof.

In some embodiments, the polypeptide has at least 80%, 85%, 90%, 91%, 92%, 93%, 94%, 95%, 96%, 97%, or 100% identity to the amino acid sequence of SEQ ID NO: 9.

In some embodiments, the polypeptide has at least 80%, 85%, 90%, 91%, 92%, 93%, 94%, 95%, 96%, 97%, or 100% identity to the amino acid sequence of SEQ ID NO: 10.

Also provided herein is an expression vector comprising a recombinant polynucleotide comprising a nucleotide sequence encoding an immunoglobulin-binding protein (Sbi) of *Staphylococcus aureus*, or a fragment thereof.

Further provided herein is a composition for delivering an isolated polypeptide comprising an immunoglobulin-binding protein (Sbi) of *Staphylococcus aureus*.

This disclosure also provides a composition for delivering a recombinant polynucleotide comprising a nucleotide sequence encoding an immunoglobulin-binding protein (Sbi) of *Staphylococcus aureus*, or a fragment thereof.

Provided herein is a pharmaceutical composition that delivers a recombinant polynucleotide comprising a nucleotide sequence encoding an immunoglobulin-binding protein (Sbi) of *Staphylococcus aureus*, or a fragment thereof; an isolated polypeptide comprising an immunoglobulin-binding protein (Sbi) of *Staphylococcus aureus*; or an expression vector comprising a recombinant polynucleotide comprising a nucleotide sequence encoding an immunoglobulin-binding protein (Sbi) of *Staphylococcus aureus*, or a fragment thereof.

In some embodiments, the pharmaceutical composition further comprises a pharmaceutically acceptable excipient, a diluent, or a combination thereof.

This disclosure provides a method comprising administering to a subject in need thereof at least one dose of a pharmaceutical composition comprising: a recombinant polynucleotide comprising a nucleotide sequence encoding an immunoglobulin-binding protein (Sbi) of *Staphylococcus aureus*, or a fragment thereof; an isolated polypeptide comprising an immunoglobulin-binding protein (Sbi) of *Staphylococcus aureus*; or an expression vector comprising a recombinant polynucleotide comprising a nucleotide sequence encoding an immunoglobulin-binding protein (Sbi) of *Staphylococcus aureus*, or a fragment thereof.

Further disclosed herein is a method for enhancing the immunogenicity of an antigen, comprising administering to a subject in need thereof, a recombinant polynucleotide comprising a nucleotide sequence encoding an immunoglobulin-binding protein (Sbi) of *Staphylococcus aureus*, or a fragment thereof; an isolated polypeptide comprising an immunoglobulin-binding protein (Sbi) of *Staphylococcus aureus*, or a pharmaceutical composition comprising the same.

This disclosure also provides a method for stimulating an immune response against an antigen, comprising administering to a subject in need thereof, a recombinant polynucleotide comprising a nucleotide sequence encoding an immunoglobulin-binding protein (Sbi) of *Staphylococcus aureus*, or a fragment thereof; an isolated polypeptide comprising an immunoglobulin-binding protein (Sbi) of *Staphylococcus aureus*, or a pharmaceutical composition comprising the same.

Also provided herein is the use of an immunoglobulin-binding protein (Sbi) of *Staphylococcus aureus* as an adjuvant in an immunogenic composition.

This disclosure provides an immunoglobulin-binding protein (Sbi) of *Staphylococcus aureus* for use as an adjuvant in an immunogenic composition.

These, and other aspects encompassed by the present disclosure, are described in more detail below and in the claims.

BRIEF DESCRIPTION OF THE DRAWINGS

FIG. 1A is a schematic showing a likely mechanism of action of Sbi(III-IV) fusions. Sbi(III-IV) binds to C3d, which in turn can drive B cell activation by binding to CR2. C3d-driven B cell co-stimulation is orthogonal to helper T cell activation, which canonically occurs through TCR recognition of a cognate MHCII-peptide complex and CD40 signaling. FIG. 1B is a graph showing a fusion of the RBD domain of SARS-CoV-2 S protein to Sbi(III-IV) leads to increased IgG titers in BALB/c mice at day 21 following a 10 μg dose of IM-delivered mRNA. Co-delivering an RBD fused to the transmembrane domain of S protein (at total mRNA dose of 10 μg) leads to a further increase in titer. The top and bottom horizontal lines indicate the detection limit of the dilution series used in the titer measurement. Sera that had titers that fell outside of that range were given values from the extreme ends of the dilution series. Values are calculated as geometric means, with the error bars corresponding to geometric standard deviation. FIG. 1C is a graph with ELISPOT counts of the number of IFNγ/IL2 double-stained colonies. For each condition, spleens from 5 mice were pooled and plated to 4 wells at 500,000 cells/well. 2 wells each were stimulated by either N-terminal or C-terminal S protein peptide pools (PepMix SARS-CoV-2 Spike Glycoprotein mix). Rates were calculated by pooling colony counts across the 4 wells, and the error bars were calculated as the Poisson error of the pooled colony counts. FIG. 1D is a graph depicting fusion fragments of RBD domain of S protein can lead to detectable humoral responses. Data displayed as described in FIG. 1B.

FIG. 2A is a schematic of a screen for protein folding. Anti-sera are generated by vaccinating mice with an mRNA vaccine encoding the full-length protein of interest. The collected anti-sera are then used to detect properly folded fragments presented in the context of a mammalian display system in a library of protein fragments. FIG. 2B is a graph showing positive and negative controls to validate the screening strategy. RBD from SARS-CoV-2 presented on the surface of HEK 293T cells and stained with anti-sera collected from RBD-vaccinated mice.

FIGS. 7A-7B depict conserved hemagglutinin HA1 residues. FIG. 7A shows the context of Y98, S/K136, W153, H183, and L/I194 receptor-contacting residues within the structure of an HA1 glycoprotein trimer. FIG. 7B depicts the conservation of receptor-contacting residues across strains spanning 92 years of seasonal influenza (SEQ ID NOs: 63-74).

CERTAIN DEFINITIONS

Figures 1A, 1B, 1C, 1D:
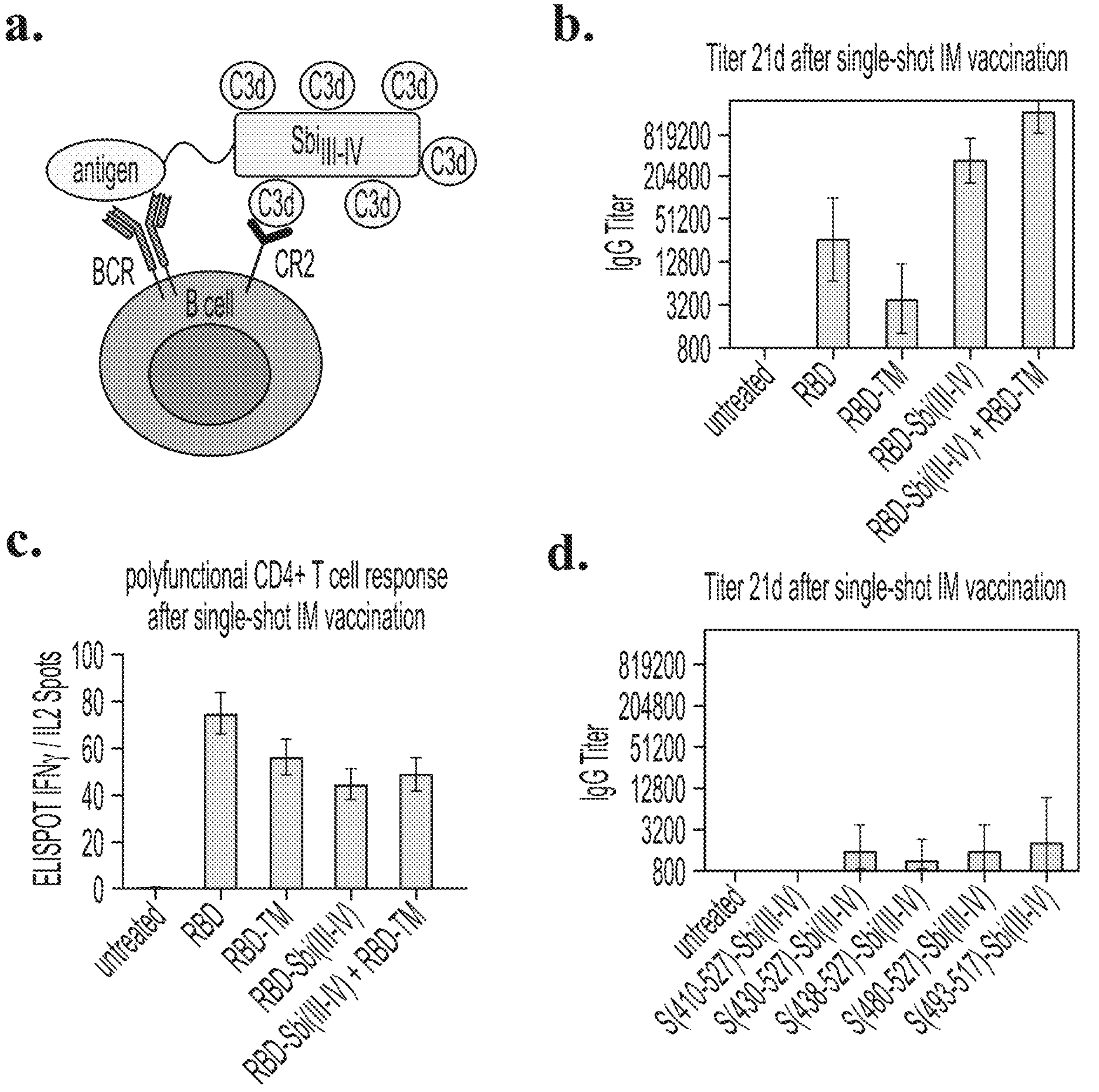
FIGS. 1A-1D describe improved antigenicity of isolated SARS-CoV-2 S protein domains with Sbi(III-IV) fusions.

About or approximately: As used herein, the terms "about" and "approximately," when used herein in reference to a value, refers to a value that is similar, in context to the referenced value. In general, those skilled in the art, familiar with the context, will appreciate the relevant degree of variance encompassed by "about" or "approximately" in that context. For example, in some embodiments, the term "about" or "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administering: As used herein, the term "administering" or "administration" typically refers to administration of a composition to a subject to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Adjuvant: The term "adjuvant," as used herein, refers to an agent that modulates and/or enhances an immune response to an agent that elicits an immune response. In some embodiments, an adjuvant is administered before, concurrently with or after administration of an agent that elicits an immune response. In some embodiments, an adjuvant and an agent that elicits an immune response are in one composition. In some embodiments, an adjuvant and an agent that elicits an immune response are in different compositions. In some embodiments, an adjuvant is or comprises a nucleic acid, polypeptide, polysaccharide, or small molecule. In some embodiments, an adjuvant is or comprises a complement binding domain. In some embodiments, an adjuvant is or comprises a C3d binding domain. In some embodiments, an adjuvant is or comprises a domain III of Sbi immunoglobulin-binding protein of *Staphylococcus aureus*, or a functional fragment or variant thereof. In some embodiments, an adjuvant is or comprises a domain IV of Sbi immunoglobulin-binding protein of *Staphylococcus aureus*, or a functional fragment or variant thereof. In some embodiments, an adjuvant comprises both a domain III and a domain IV of the Sbi of *Staphylococcus aureus*, or a functional fragment or a variant thereof.

Antigen: The term "antigen", as used herein, refers to an agent that elicits an immune response; and/or (ii) an agent that binds to a T cell receptor (e.g., when presented by an MHC molecule) or to an antibody. In some embodiments, an antigen elicits a humoral response (e.g., including production of antigen-specific antibodies); in some embodiments, an antigen elicits a cellular response (e.g., involving T-cells whose receptors specifically interact with the antigen). In some embodiments, an antigen comprises at least one epitope of a target protein. In some embodiments, an epitope may be a linear epitope. In some embodiments, an epitope may be a conformational epitope. In some embodiments, an antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments other than a biologic polymer [e.g., other than a nucleic acid or amino acid polymer) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is a recombinant antigen.

Antigen variant: As used herein, the term "antigen variant" refers to an antigen that shows significant structural identity with a target protein antigen but differs structurally from the target protein antigen in the presence or level of one or more chemical moieties as compared to the target protein antigen. In some embodiments, an antigen variant differs functionally from a target protein antigen. In some embodiments, an antigen variant does not differ functionally from a target protein antigen. In some embodiments, an antigen comprises an epitope of a target protein antigen. In some embodiments, an antigen variant differs from a target protein antigen as a result of one or more differences in amino acid sequence and/or one or more differences in chemical moieties (e.g., carbohydrates, lipids, etc.) covalently attached to the polypeptide backbone.

Delivery/contacting: As used interchangeably herein, the term "delivery," "delivering," or "contacting" refers to introduction of a fusion polynucleotide (e.g., as described herein) or a fusion polypeptide (e.g., as described herein) into a target cell. A target cell can be cultured in vitro or ex vivo or be present in a subject (in vivo). Methods of introducing a fusion polynucleotide (e.g., as described herein) or a fusion polypeptide (e.g., as described herein) into a target cell can vary with in vitro, ex vivo, or in vivo applications. In some embodiments, a fusion polynucleotide (e.g., as described herein) or a fusion polypeptide (e.g., as described herein) can be introduced into a target cell in a cell culture by in vitro transfection. In some embodiments, a fusion polynucleotide (e.g., as described herein) or a fusion polypeptide (e.g., as described herein) can be introduced into a target cell via delivery vehicles (e.g., nanoparticles, liposomes, and/or complexation with a cell-penetrating agent). In some embodiments, a fusion polynucleotide (e.g., as described herein) or a fusion polypeptide (e.g., as described herein) can be introduced into a target cell in a subject by administering a fusion polynucleotide (e.g., as described herein) or a fusion polypeptide (e.g., as described herein) to a subject.

Functional: As used herein, the term "functional" is used to refer to a form or fragment of an entity that exhibits a particular property and/or activity.

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a fragment comprises a polynucleotide fragment. In some embodiments, a fragment comprises a polypeptide fragment. In some embodiments, a polynucleotide fragment or a polypeptide fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polynucleotide or whole polypeptide. In some embodiments, a polynucleotide fragment or a polypeptide fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polynucleotide or whole polypeptide. The whole polypeptide or whole polynucleotide may in some embodiments be referred to as the "parent" of the polynucleotide fragment or polypeptide fragment.

Fragment antigen: A "fragment antigen" is used herein to refer to a fragment which comprises an epitope of a target protein antigen. In some embodiments, an epitope is or comprises an epitope presented by MHC Class I. In some embodiments, an epitope is or comprises an epitope presented by MHC Class II. In some embodiments, a fragment antigen is a polypeptide fragment antigen. In some embodiments, a fragment antigen is encoded by a polynucleotide encoding a fragment antigen. In some embodiments, a polypeptide fragment antigen comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 200, 250, 300 or more monomeric units (e.g., residues) as found in a target protein antigen polypeptide. In some embodiments, a polypeptide fragment antigen comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in a target protein antigen polypeptide. In some embodiments, a polypeptide fragment antigen comprises or consists of no more than about 50%, 40%, 30%, 20%, 10%, or 5% of the monomeric units (e.g., residues) found in a target protein antigen polypeptide.

Fragment antigen variant: As used herein, the term "fragment antigen variant" refers to a fragment antigen that shows significant sequence and/or structural identity with a fragment antigen but differs in sequence and/or structure from the fragment antigen in the presence or level of one or more chemical moieties as compared to the fragment antigen. In some embodiments, a fragment antigen variant differs functionally from a fragment antigen. In some embodiments, a fragment antigen variant does not differ functionally from a fragment antigen. In some embodiments, a fragment antigen variant differs from a fragment antigen as a result of one or more differences in amino acid sequence and/or one or more differences in chemical moieties (e.g., carbohydrates, lipids, etc.) covalently attached to the polypeptide backbone.

Nucleic acid/Oligonucleotide/Polynucleotide: As used herein, the terms "nucleic acid" and "polynucleotide" and "oligonucleotide" are used interchangeably, and refer to a polymer of 3 nucleotides or more. In some embodiments, a nucleic acid comprises DNA. In some embodiments, a nucleic acid comprises RNA. In some embodiments, a nucleic acid comprises messenger RNA (mRNA). In some embodiments, a nucleic acid is single stranded. In some embodiments, a nucleic acid is double stranded. In some embodiments, a nucleic acid comprises both single and double stranded portions. In some embodiments, a nucleic acid comprises a backbone that comprises one or more phosphodiester linkages. In some embodiments, a nucleic acid comprises a backbone that comprises both phosphodiester and non-phosphodiester linkages. For example, in some embodiments, a nucleic acid may comprise a backbone that comprises one or more phosphorothioate or 5'-N-phosphoramidite linkages and/or one or more peptide bonds, e.g., as in a "peptide nucleic acid". In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises on or more, or all, non-natural residues. In some embodiments, a non-natural residue comprises a nucleoside analog (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 6-O-methylguanine, 2-thiocytidine, methylated bases, intercalated bases, and combinations thereof). In some embodiments, a non-natural residue comprises one or more modified sugars (e.g., 2'-fluororibose, ribose, 2'-deoxyribose, arabinose, and hexose) as compared to those in natural residues. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, or 20,000 or more residues or nucleotides long. When a number of nucleotides is used as an indication of size, e.g., of a fusion polynucleotide, a certain number of nucleotides refers to the number of nucleotides on a single strand, e.g., of a fusion polynucleotide.

Polypeptide: The term "polypeptide", as used herein, generally has its art-recognized meaning of a polymer of at least three amino acids or more. Those of ordinary skill in the art will appreciate that the term "polypeptide" is intended to be sufficiently general as to encompass not only polypeptides having a complete sequence recited herein, but also to encompass polypeptides that represent functional, biologically active, or characteristic fragments, portions or domains (e.g., fragments, portions, or domains retaining at least one activity) of such complete polypeptides. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, polypeptides may comprise natural amino acids, non-natural amino acids, synthetic amino acids, and combinations thereof.

RNA oligonucleotide: As used herein, the term "RNA oligonucleotide" refers to an oligonucleotide of ribonucleotides. In some embodiments, an RNA oligonucleotide is single stranded. In some embodiments, an RNA oligonucleotide is double stranded. In some embodiments, an RNA oligonucleotide comprises both single and double stranded portions. In some embodiments, an RNA oligonucleotide can comprise a backbone structure as described in the definition of "*Nucleic acid/Oligonucleotide*" above. An RNA oligonucleotide can be a regulatory RNA (e.g., siRNA, microRNA, etc.), or a messenger RNA (mRNA) oligonucleotide. In some embodiments where an RNA oligonucleotide is a mRNA oligonucleotide, an RNA oligonucleotide typically comprises at its 3' end a poly(A) region. In some embodiments where an RNA oligonucleotide is a mRNA oligonucleotide, an RNA oligonucleotide typically comprises at its 5' end an art-recognized cap structure, e.g., for recognizing and attachment of a mRNA to a ribosome to initiate translation. In some embodiments, a polynucleotide (e.g., a fusion polynucleotide) comprises an RNA oligonucleotide. When a number of ribonucleotides is used as an indication of size, e.g., of a fusion polynucleotide, a certain number of nucleotides refers to the number of ribonucleotides on a single strand, e.g., of a fusion polynucleotide.

Subject: As used herein, the term "subject" refers an organism, typically a mammal (e.g., a human). In some embodiments, a subject is suffering from a disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide.

Standard techniques may be used for recombinant DNA, oligonucleotide synthesis, e.g., mRNA synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2nd ed., Cold Spring Harbor Laboratory Press, Cold Spring Harbor, N.Y. (1989)), which is incorporated herein by reference for any purpose.

DETAILED DESCRIPTION OF CERTAIN EMBODIMENTS

Traditional vaccine adjuvants, such as alum and poly-IC, typically work by activating one or more Toll like receptors (TLR) and thereby putting local tissue into an anti-viral state. In contrast, achieving high levels of antigen production with RNA vaccines, e.g., mRNA vaccines, demands minimal immunogenicity, as localized innate immune responses can dramatically reduce expression levels. This disclosure provides an RNA-native adjuvant technology, e.g., mRNA-native adjuvant technology, that can provide improvements in the strength of the immune response, without creating a countervailing effect on antigen expression. This can be accomplished, e.g., by using protein-based fusions to make the RNA-encoded antigen, e.g., mRNA-encoded antigen, more immunogenic in a way that was decoupled from the immunogenicity of the vaccine itself. In one embodiment, the fusion protein would either directly stimulate and/or drive uptake by B cells, while minimizing non-specific inflammation at the site of RNA, e.g., mRNA, expression. A large set of candidate fusion domains were screened, and it was observed that Sbi fragments described herein improved antibody titers across a range of antigen expression levels. This represents a first-in-class solution to making adjuvants that work well with RNA-based, e.g., mRNA-based, vaccines. Since viral and DNA vaccine vectors face the same immunogenicity-antigen expression optimization challenge, Sbi fragments described herein, e.g., SbiIII-IV, can be used to improve other classes of nucleic acid-based vaccines.

Without wishing to be bound by theory, it is believed that given what is known about the mechanism of action of SbiIII-IV, the fusion approach described herein has the additional benefit of extending the design space of effective antigens. Antibody production is driven by B cells that both 1) bind the antigen via their B cell receptor (BCR); and 2) become activated by a second signal. The activation signal is most commonly provided by a helper T cell, which means that effective antigens need to both bind BCRs, and contain peptides that are efficiently presented on MHC and that bind T cell receptor (TCR)s. SbiIII-IV, in contrast, binds to complement fragments that can directly license B cells, bypassing the need to generate a strong response in helper T cells. This can extend the design space of effective antigens by enabling, e.g., the use of fragments that lack good T cell epitopes. In some embodiments, one of the applications of the SbiIII-IV-based fusion architecture is to make minimal antigens containing only a portion of the naturally occurring protein. As an example, this disclosure provides compositions and uses of SbiIII-IV-based fusions comprising a portion of the SARS-CoV-2 spike protein (e.g., RBD and sub-RBD portions) as an exemplary antigen fused to an Sbi fragment (SbiIII-IV) which have enhanced antigenicity (see Example 1) and/or stimulate a productive humoral immune response (see Examples 2-4).

The present disclosure is the first to recognize that vaccination with a fragment antigen fused to an adjuvant comprising a complement C3d-binding region, can enhance the titers of the resulting antibody response and/or result in a measurable T cell response. In some embodiments, the adjuvant is or comprises a complement C3d-binding region of a Sbi protein from *Staphylococcus aureus*. In some embodiments, a fragment antigen fused to an adjuvant comprising a complement C3d-binding region serves as a synthetic immunological synapse, mimicking natural viral infection to drive a strong and appropriate immune response. In some embodiments, a fragment antigen fused to an adjuvant comprising a complement C3d-binding region allows small antigens that lack MHC-presented peptides to elicit meaningful humoral response.

The present disclosure also recognizes that vaccination with a fragment antigen or a variant antigen (instead of a full-length antigen) can be useful for developing vaccines that are less resistant to viral mutations and are broadly neutralizing. The vaccination approaches described herein can focus the immune response on conserved and/or functional regions to improve the breadth and efficacy of a vaccine. Without wishing to be bound by theory, it is believed that in some embodiments, immunofocusing can occur with use of fragment antigens that: (1) minimally comprise an epitope of a target protein antigen which can be presented on MHC I and/or MHC II; and/or (2) have a confirmation that is similar to that of the full-length or native target protein antigen.

Fragment Antigens or Variant Antigens

This disclosure provides fragment antigens or variant antigens which comprise an epitope of a target protein antigen and compositions comprising the same. In some embodiments, a fragment antigen or a variant antigen is fused to an adjuvant, e.g., a C3d binding polypeptide, for use in an immunogenic composition.

In some embodiments, a fragment antigen or a variant antigen comprises an epitope (e.g., T cell epitope) of a target protein antigen. In some embodiments, a fragment antigen or a variant antigen comprises a portion of an epitope (e.g., T cell epitope) of a target protein antigen.

In some embodiments, a fragment antigen or a variant antigen does not comprise an epitope e.g., T cell epitope) of a target protein antigen.

In some embodiments, a fragment antigen has an amino acid sequence length of at least 5%, 10%, 20%, 30%, 40%, 50%, 60%, 70%, 80%, 90% or 95% compared to the amino acid sequence length of the target protein antigen. In some embodiments, a fragment antigen has an amino acid sequence length of no more than 50% of the amino acid sequence length of the target protein antigen. In some embodiments, a fragment antigen has an amino acid sequence length of no more than 40%, 30%, 20%, 10% or 5% of the amino acid sequence length of the target protein antigen.

In some embodiments, a fragment antigen has about 10-300 amino acid residues in length. In some embodiments, a fragment antigen has at least 10 amino acid residues in length. In some embodiments, a fragment antigen has less than about 300 amino acid residues in length. In some embodiments, a fragment antigen has about 10-300, 10-250, 10-200, 10-150, 10-100, 10-90, 10-80, 10-70, 10-60, 10-50, 10-40, 10-30, 10-20, 20-300, 30-300, 40-300, 50-300, 60-300, 70-300, 80-300, 90-100, 100-300, 150-300, 200-300, 250-300, 20-250, 30-200, 40-150, 50-100, 60-90, or 70-80 amino acids residues in length. In some embodiments, a fragment antigen has about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 amino acids residues in length.

In some embodiments, an antigen variant or fragment antigen variant amino acid sequence length is identical to the amino acid sequence length of the target protein antigen.

In some embodiments, an antigen variant or fragment antigen variant comprises at least one modified amino acid compared to the target protein antigen. In some embodiments, a modified amino acid comprises N-linked glycosylation. In some embodiments, an antigen variant or fragment antigen variant comprises at least one amino acid mutation compared to the target protein antigen. In some embodiments, an antigen variant or fragment antigen variant comprises 2, 3, 4, 5, 6, 7, 8, 9, 10, 15, 20, 30, 40 or 50 amino acid mutations compared to the target protein antigen. In some embodiments, the mutation introduces a Serine, a Threonine, an Alanine, or an amino acid at a particular position which is different from the amino acid present at that position in the target protein antigen. In some embodiments, the mutation prevents formation of a disulfide bond.

In some embodiments, a fragment antigen is characterized in that when expressed in vivo, it binds to a Major Histocompatibility Complex (MHC) molecule.

In some embodiments, a fragment antigen is characterized in that when expressed in vivo, it does not bind to a MHC molecule.

In some embodiments, a MHC molecule is or comprises a MHC I molecule or a MHC II molecule.

In some embodiments, a fragment antigen is characterized in that when expressed in vivo, it folds into a three-dimensional conformation that is substantially identical to the three-dimensional conformation of the fragment antigen as it is in its native position in the target protein antigen.

In some embodiments, a fragment antigen, antigen variant or fragment antigen variant further comprises an amino acid sequence from a second target protein antigen.

Target Protein Antigens

Among other things, provided herein are fusion polypeptides comprising a fragment antigen or a variant antigen comprising an epitope of a target protein antigen. Also provided herein are fusion polynucleotides encoding fusion polypeptides comprising a fragment antigen or a variant antigen comprising an epitope of a target protein antigen.

In some embodiments, a target protein antigen is or comprises an infectious disease antigen. In some embodiments, an infectious disease antigen is or comprises a viral antigen, a bacterial antigen, a fungal antigen, or combinations thereof. In some embodiments, a viral antigen is or comprises an influenza antigen. In some embodiments, a viral antigen is or comprises a coronavirus polypeptide. In some embodiments, a coronavirus polypeptide is or comprises a SARS-CoV-2 protein, e.g., as described herein.

In some embodiments, a target protein antigen is or comprises a cancer antigen.

SARS-CoV-2 Antigens

Exemplary antigens that can be included in any of the fusion polypeptides, fusion polynucleotides, compositions, methods or uses disclosed herein include one or more SARS-CoV-2 polypeptides. In some embodiments, a target protein antigen disclosed herein is or comprises a SARS-CoV-2 antigen. In some embodiments, a SARS-CoV-2 antigen is chosen from: a Spike glycoprotein (SARS-CoV-2 S) polypeptide or antigenic fragment thereof; an Envelope protein (SARS-CoV-2 E) polypeptide or antigenic fragment thereof; a Membrane protein (SARS-CoV-2 M) polypeptide or antigenic fragment thereof; a nucleocapsid protein (SARS-CoV-2 N) polypeptide or antigenic fragment thereof; an accessory factor polypeptide or antigenic fragment thereof; or any combination thereof.

In some embodiments, an antigen, e.g., a fragment antigen or a variant antigen, comprises an epitope from a target protein antigen which is or comprises a SARS-CoV-2 polypeptide. In some embodiments, an antigen, e.g., a fragment antigen or a variant antigen, comprises an epitope from a SARS-CoV-2 Spike glycoprotein (SARS-CoV-2 S) polypeptide or a fragment thereof (e.g., RBD).

The SARS-CoV-2 S polypeptide is referenced by Gene ID: 43740568 and/or NCBI RefNC_045512.2. An amino acid sequence for SARS-CoV-2 S polypeptide is provided by SEQ ID NO: 58:

MFVFLVLLPLVSSQCVNLTTRTQLPPAYTNSFTRGVYYPDKVFR
SSVLHSTQDLFLPFFSNVTWFHAIHVSGTNGTKRFDNPVLPFNDGVYFAS
TEKSNIIRGWIFGTTLDSKTQSLLIVNNATNVVIKVCEFQFCNDPFLGVY
YHKNNKSWMESEFRVYSSANNCTFEYVSQPFLMDLEGKQGNFKNLREFVF
KNIDGYFKIYSKHTPINLVRDLPQGFSALEPLVDLPIGINITRFQTLLAL
HRSYLTPGDSSSGWTAGAAAYYVGYLQPRTFLLKYNENGTITDAVDCALD
PLSETKCTLKSFTVEKGIYQTSNFRVQPTESIVRFPNITNLCPFGEVFNA
TRFASVYAWNRKRISNCVADYSVLYNSASFSTFKCYGVSPTKLNDLCFTN
VYADSFVIRGDEVRQIAPGQTGKIADYNYKLPDDFTGCVIAWNSNNLDSK
VGGNYNYLYRLFRKSNLKPFERDISTEIYQAGSTPCNGVEGFNCYFPLQS
YGFQPTNGVGYQPYRVVVLSFELLHAPATVCGPKKSTNLVKNKCVNFNFN
GLTGTGVLTESNKKFLPFQQFGRDIADTTDAVRDPQTLEILDITPCSFGG
VSVITPGTNTSNQVAVLYQDVNCTEVPVAIHADQLTPTWRVYSTGSNVFQ
TRAGCLIGAEHVNNSYECDIPIGAGICASYQTQTNSPRRARSVASQSIIA
YTMSLGAENSVAYSNNSIAIPTNFTISVTTEILPVSMTKTSVDCTMYICG
DSTECSNLLLQYGSFCTQLNRALTGIAVEQDKNTQEVFAQVKQIYKTPPI
KDFGGFNFSQILPDPSKPSKRSFIEDLLFNKVTLADAGFIKQYGDCLGDI
AARDLICAQKFNGLTVLPPLLTDEMIAQYTSALLAGTITSGWTFGAGAAL
QIPFAMQMAYRFNGIGVTQNVLYENQKLIANQFNSAIGKIQDSLSSTASA
LGKLQDVVNQNAQALNTLVKQLSSNFGAISSVLNDILSRLDKVEAEVQID
RLITGRLQSLQTYVTQQLIRAAEIRASANLAATKMSECVLGQSKRVDFCG
KGYHLMSFPQSAPHGVVFLHVTYVPAQEKNFTTAPAICHDGKAHFPREGV
FVSNGTHWFVTQRNFYEPQIITTDNTFVSGNCDVVIGIVNNTVYDPLQPE
LDSFKEELDKYFKNHTSPDVDLGDISGINASVVNIQKEIDRLNEVAKNLN
ESLIDLQELGKYEQYIKWPWYIWLGFIAGLIAIVMVTIMLCCMTSCCSCL
KGCCSCGSCCKFDEDDSEPVLKGVKLHYT

A polynucleotide sequence for SARS-CoV-2 S polypeptide is provided by SEQ ID NO: 59:

```
  1 atgtttgttt ttcttgtttt attgccacta gtctctagtc agtgtgttaa tcttacaacc

 61 agaactcaat taccccctgc atacactaat tctttcacac gtggtgttta ttaccctgac

121 aaagttttca gatcctcagt tttacattca actcaggact tgttcttacc tttcttttcc

181 aatgttactt ggttccatgc tatacatgtc tctgggacca atggtactaa gaggtttgat

241 aaccctgtcc taccatttaa tgatggtgtt tattttgctt ccactgagaa gtctaacata

301 ataagaggct ggatttttgg tactacttta gattcgaaga cccagtccct acttattgtt
```

-continued

```
 361 aataacgcta ctaatgttgt tattaaagtc tgtgaatttc aattttgtaa tgatccattt
 421 ttgggtgttt attaccacaa aaacaacaaa agttggatgg aaagtgagtt cagagtttat
 481 tctagtgcga ataattgcac ttttgaatat gtctctcagc cttttcttat ggaccttgaa
 541 ggaaaacagg gtaatttcaa aaatcttagg gaatttgtgt ttaagaatat tgatggttat
 601 tttaaaatat attctaagca cacgcctatt aatttagtgc gtgatctccc tcagggtttt
 661 tcggctttag aaccattggt agatttgcca ataggtatta acatcactag gtttcaaact
 721 ttacttgctt tacatagaag ttatttgact cctggtgatt cttcttcagg ttggacagct
 781 ggtgctgcag cttattatgt gggttatctt caacctagga cttttctatt aaaatataat
 841 gaaaatggaa ccattacaga tgctgtagac tgtgcacttg accctctctc agaaacaaag
 901 tgtacgttga aatccttcac tgtagaaaaa ggaatctatc aaacttctaa ctttagagtc
 961 caaccaacag aatctattgt tagatttcct aatattacaa acttgtgccc ttttggtgaa
1021 gtttttaacg ccaccagatt tgcatctgtt tatgcttgga acaggaagag aatcagcaac
1081 tgtgttgctg attattctgt cctatataat tccgcatcat tttccacttt taagtgttat
1141 ggagtgtctc ctactaaatt aaatgatctc tgctttacta atgtctatgc agattcattt
1201 gtaattagag gtgatgaagt cagacaaatc gctccagggc aaactggaaa gattgctgat
1261 tataattata aattaccaga tgattttaca ggctgcgtta tagcttggaa ttctaacaat
1321 cttgattcta aggttggtgg taattataat tacctgtata gattgtttag gaagtctaat
1381 ctcaaacctt ttgagagaga tatttcaact gaaatctatc aggccggtag cacaccttgt
1441 aatggtgttg aaggttttaa ttgttacttt cctttacaat catatggttt ccaacccact
1501 aatggtgttg gttaccaacc atacagagta gtagtacttt cttttgaact tctacatgca
1561 ccagcaactg tttgtggacc taaaaagtct actaatttgg ttaaaaacaa atgtgtcaat
1621 ttcaacttca atggtttaac aggcacaggt gttcttactg agtctaacaa aaagtttctg
1681 cctttccaac aatttggcag agacattgct gacactactg atgctgtccg tgatccacag
1741 acacttgaga ttcttgacat tacaccatgt tcttttggtg gtgtcagtgt tataacacca
1801 ggaacaaata cttctaacca ggttgctgtt ctttatcagg atgttaactg cacagaagtc
1861 cctgttgcta ttcatgcaga tcaacttact cctacttggc gtgtttattc tacaggttct
1921 aatgtttttc aaacacgtgc aggctgttta ataggggctg aacatgtcaa caactcatat
1981 gagtgtgaca tacccattgg tgcaggtata tgcgctagtt atcagactca gactaattct
2041 cctcggcggg cacgtagtgt agctagtcaa tccatcattg cctacactat gtcacttggt
2101 gcagaaaatt cagttgctta ctctaataac tctattgcca tacccacaaa ttttactatt
2161 agtgttacca cagaaattct accagtgtct atgaccaaga catcagtaga ttgtacaatg
2221 tacatttgtg gtgattcaac tgaatgcagc aatcttttgt tgcaatatgg cagtttttgt
2281 acacaattaa accgtgcttt aactggaata gctgttgaac aagacaaaaa cacccaagaa
2341 gtttttgcac aagtcaaaca aatttacaaa acaccaccaa ttaaagattt tggtggtttt
2401 aatttttcac aaatattacc agatccatca aaaccaagca agaggtcatt tattgaagat
2461 ctacttttca acaaagtgac acttgcagat gctggcttca tcaaacaata tggtgattgc
2521 cttggtgata ttgctgctag agacctcatt tgtgcacaaa agtttaacgg ccttactgtt
2581 ttgccacctt tgctcacaga tgaaatgatt gctcaataca cttctgcact gttagcgggt
2641 acaatcactt ctggttggac ctttggtgca ggtgctgcat tacaaatacc atttgctatg
2701 caaatggctt ataggtttaa tggtattgga gttacacaga atgttctcta tgagaaccaa
```

-continued

```
2761 aaattgattg ccaaccaatt taatagtgct attggcaaaa ttcaagactc actttcttcc

2821 acagcaagtg cacttggaaa acttcaagat gtggtcaacc aaaatgcaca agctttaaac

2881 acgcttgtta aacaacttag ctccaatttt ggtgcaattt caagtgtttt aaatgatatc

2941 ctttcacgtc ttgacaaagt tgaggctgaa gtgcaaattg ataggttgat cacaggcaga

3001 cttcaaagtt tgcagacata tgtgactcaa caattaatta gagctgcaga aatcagagct

3061 tctgctaatc ttgctgctac taaaatgtca gagtgtgtac ttggacaatc aaaaagagtt

3121 gatttttgtg gaaagggcta tcatcttatg tccttccctc agtcagcacc tcatggtgta

3181 gtcttcttgc atgtgactta tgtccctgca caagaaaaga acttcacaac tgctcctgcc

3241 atttgtcatg atggaaaagc acactttcct cgtgaaggtg tctttgtttc aaatggcaca

3301 cactggtttg taacacaaag gaatttttat gaaccacaaa tcattactac agacaacaca

3361 tttgtgtctg gtaactgtga tgttgtaata ggaattgtca acaacacagt ttatgatcct

3421 ttgcaacctg aattagactc attcaaggag gagttagata aatattttaa gaatcataca

3481 tcaccagatg ttgatttagg tgacatctct ggcattaatg cttcagttgt aaacattcaa

3541 aaagaaattg accgcctcaa tgaggttgcc aagaatttaa atgaatctct catcgatctc

3601 caagaacttg gaaagtatga gcagtatata aaatggccat ggtacatttg gctaggtttt

3661 atagctggct tgattgccat agtaatggtg acaattatgc tttgctgtat gaccagttgc

3721 tgtagttgtc tcaagggctg ttgttcttgt ggatcctgct gcaaatttga tgaagacgac

3781 tctgagccag tgctcaaagg agtcaaatta cattacacat aa
```

In some embodiments, a target protein antigen is or comprises a SARS-CoV-2 S polypeptide. In some embodiments, a target protein antigen comprises a polypeptide having at least 80%, 85%, 90%, 91%, 92%, 93%, 94%, 95%, 96%, 97%, 98%, 99% or 100% identity to an amino acid sequence of a SARS-CoV-2 S polypeptide or a fragment thereof as described herein. In some embodiments, a target protein antigen comprises a polypeptide having at least 80%, 85%, 90%, 91%, 92%, 93%, 94%, 95%, 96%, 97%, 98%, 99% or 100% identity to the amino acid sequence of SEQ ID NO: 58.

In some embodiments, a fragment antigen comprises an epitope of a SARS-CoV-2 S polypeptide. In some embodiments, a fragment antigen comprises a polypeptide having at least 80%, 85%, 90%, 91%, 92%, 93%, 94%, 95%, 96%, 97%, 98%, 99% or 100% identity to an amino acid sequence of a SARS-CoV-2 S polypeptide or a fragment thereof as described herein. In some embodiments, a fragment antigen comprises a polypeptide having at least 80%, 85%, 90%, 91%, 92%, 93%, 94%, 95%, 96%, 97%, 98%, 99% or 100% identity to the amino acid sequence of SEQ ID NO: 58.

In some embodiments, a fragment antigen comprises an epitope of a SARS-CoV-2 S polypeptide. In some embodiments, a fragment antigen comprises a polynucleotide encoding a polypeptide having at least 80%, 85%, 90%, 91%, 92%, 93%, 94%, 95%, 96%, 97%, 98%, 99% or 100% identity to an amino acid sequence of a SARS-CoV-2 S polypeptide or a fragment thereof as described herein. In some embodiments, a fragment antigen comprises a polynucleotide having at least 80%, 85%, 90%, 91%, 92%, 93%, 94%, 95%, 96%, 97%, 98%, 99% or 100% identity to the nucleic acid sequence of SEQ ID NO: 59. Due to degeneracy in the genetic code, those of ordinary skill in the art would understand that other DNA sequences (including codon-optimized sequences) could encode these polypeptides, as well as the others disclosed herein.

Adjuvants

In some embodiments, an adjuvant disclosed herein can be used to elicit and/or modulate an immune response elicited by an antigen (e.g., fragment antigen or antigen variant) described herein. In some embodiments, an adjuvant disclosed herein comprises a complement binding polypeptide. In some embodiments, a complement binding polypeptide comprises a complement C3d binding polypeptide. An exemplary C3d binding polypeptide is an immunoglobulin-binding protein (Sbi) of *Staphylococcus aureus*.

In some embodiments of any of the fusion polypeptides, fusion nucleotides, compositions, methods or uses disclosed herein, an adjuvant disclosed herein can be used alone or in combination with an antigen disclosed herein to modulate and/or enhance an immune response. In an embodiment, an adjuvant disclosed herein can comprise a fusion polypeptide which comprises a fragment antigen or variant antigen and an adjuvant (e.g., C3d binding polypeptide). In some embodiments, also disclosed herein are fusion polynucleotides encoding fusion polypeptides comprising a fragment antigen or variant antigen and an adjuvant (e.g., C3d binding polypeptide). In some embodiments, a fusion polynucleotide comprises DNA or RNA. In some embodiments, a fusion polynucleotide comprises RNA, e.g., messenger RNA. In some embodiments, a fusion polynucleotide comprising RNA (e.g., messenger RNA) is characterized in that when administered to a subject reduces immunogenicity to an antigen comprised in the fusion polynucleotide.

*S. aureus* Sbi

As disclosed herein, *S. aureus* binder of immunoglobulin (Sbi) is an exemplary polypeptide which can bind complement C3d (as described in Clark et al. (2011) Mot Immunol. 48(4): 452-462, the entire contents of which is incorporated herein by reference). Sbi comprises two immunoglobulin binding domains (Domains I and II) and two complement C3d binding domains (Domains III and IV). Sbi domains III and IV can bind C3d (in native C3, iC3b and C3dg) and can result in fluid phase consumption of C3 via activation of the alternative pathway (see Clark et al 2011). It has also been shown that Sbi can be secreted and is involved in *S. aureus* immune evasion (Burman et al., 2008 *J. Biol. Chem;* 283: 17579-17593).

Without wishing to be bound by theory, it is believed that in some embodiments, a complement C3d-binding polypeptide from Sbi of *S. aureus* can be used as an adjuvant to enhance and/or modulate an immune response from an antigen described herein. In some embodiments, the immune response is elicited by a fragment antigen or antigen variant disclosed herein. In some embodiments, the immune response is elicited by a component of Sbi of *S. aureus*.

*S. aureus* Sbi is referenced by Gene ID: 3919725 and NCBI Ref No.: NC_007795.1. A polynucleotide sequence of Sbi is provided herein as SEQ ID NO: 56:

```
   1 atgaaaaata aatatatctc gaagttgcta gttggggcag caacaattac gttagctaca
  61 atgatttcaa atggggaagc aaaagcgagt gaaaacacgc aacaaacttc aactaagcac
 121 caaacaactc aaaacaacta cgtaacagat caacaaaaag ctttttatca agtattacat
 181 ctaaaaggta tcacagaaga acaacgtaac caatacatca aaacattacg cgaacaccca
 241 gaacgtgcac aagaagtatt ctctgaatca cttaaagaca gcaagaaccc agaccgacgt
 301 gttgcacaac aaaacgcttt ttacaatgtt cttaaaaatg ataacttaac tgaacaagaa
 361 aaaaataatt acattgcaca aattaaagaa aaccctgata gaagccaaca agtttgggta
 421 gaatcagtac aatcttctaa agctaaagaa cgtcaaaata ttgaaaatgc ggataaagca
 481 attaaagatt tccaagataa caaagcacca cacgataaat cagcagcata tgaagctaac
 541 tcaaaattac ctaaagattt acgtgataaa aacaaccgct ttgtagaaaa agtttcaatt
 601 gaaaaagcaa tcgttcgtca tgatgagcgt gtgaaatcag caaatgatgc aatctcaaaa
 661 ttaaatgaaa aagattcaat tgaaaacaga cgtttagcac aacgtgaagt taacaaagca
 721 cctatggatg taaaagagca tttacagaaa caattagacg cattagttgc tcaaaaagat
 781 gctgaaaaga aagtggcgcc aaaagttgag gctcctcaaa ttcaatcacc acaaattgaa
 841 aaacctaaag tagaatcacc aaaagttgaa gtccctcaaa ttcaatcacc aaaagttgag
 901 gttcctcaat ctaaattatt aggttactac caatcattaa aagattcatt taactatggt
 961 tacaagtatt taacagatac ttataaaagc tataaagaaa aatatgatac agcaaagtac
1021 tactataata cgtactataa atacaaaggt gcgattgatc aaacagtatt aacagtacta
1081 ggtagtggtt ctaaatctta catccaacca ttgaaagttg atgataaaaa cggctactta
1141 gctaaatcat atgcacaagt aagaaactat gtaactgagt caatcaatac tggtaaagta
1201 ttatatactt tctaccaaaa cccaacatta gtaaaaacag ctattaaagc tcaagaaact
1261 gcatcatcaa tcaaaaatac attaagtaat ttattatcat tctggaaata a
```

A polypeptide sequence of Sbi is provided herein as SEQ ID NO: 57.

```
MKNKYISKLLVGAATITLATMISNGEAKASENTQQTSTKHQTTQNNYVTD

QQKAFYQVLHLKGITEEQRNQYIKTLREHPERAQEVFSESLKDSKNPDRR

VAQQNAFYNVLKNDNLTEQEKNNYIAQIKENPDRSQQVWVESVQSSKAKE

RQNIENADKAIKDFQDNKAPHDKSAAYEANSKLPKDLRDKNNRFVEKVSI

EKAIVRHDERVKSANDAISKLNEKDSIENRRLAQREVNKAPMDVKEHLQK
```

-continued

```
QLDALVAQKDAEKKVAPKVEAPQIQSPQIEKPKVESPKVEVPQIQSPKVE

VPQSKLLGYYQSLKDSFNYGYKYLTDTYKSYKEKYDTAKYYYNTYYKYKG

AIDQTVLTVLGSGSKSYIQPLKVDDKNGYLAKSYAQVRNYVTESINTGKV

LYTFYQNPTLVKTAIKAQETASSIKNTLSNLLSFWK
```

In some embodiments, any of the fusion polypeptides, fusion nucleotides, compositions, methods or uses disclosed herein, comprises a complement C3d-binding polypeptide of Sbi of *S. aureus*. In some embodiments, a Sbi complement C3d binding polypeptide comprises one or both of domain III and domain IV of Sbi, or a functional fragment or a variant thereof.

In some embodiments, a Sbi complement C3d binding polypeptide comprises an amino acid sequence having at least 80%, 85%, 90%, 91%, 92%, 93%, 94%, 95%, 96%, 97%, or 100% identity to the amino acid sequence of SEQ ID NO: 9. In some embodiments, a Sbi complement C3d binding polypeptide comprises an amino acid sequence having at least 80%, 85%, 90%, 91%, 92%, 93%, 94%, 95%, 96%, 97%, or 100% identity to the amino acid sequence of SEQ ID NO: 10. In some embodiments, a Sbi complement C3d binding polypeptide comprises an amino acid sequence having at least 80%, 85%, 90%, 91%, 92%, 93%, 94%, 95%, 96%, 97%, 98%, 99% or 100% identity to the amino acid sequence of SEQ ID NO: 57.

In some embodiments, a Sbi complement C3d binding polypeptide is encoded by a polynucleotide which encodes an amino acid having at least 80%, 85%, 90%, 91%, 92%, 93%, 94%, 95%, 96%, 97%, or 100% identity to the amino acid sequence of SEQ ID NO: 9. In some embodiments, a Sbi complement C3d binding polypeptide is encoded by a polynucleotide which encodes an amino acid having at least 80%, 85%, 90%, 91%, 92%, 93%, 94%, 95%, 96%, 97%, or 100% identity to the amino acid sequence of SEQ ID NO: 10. In some embodiments, a Sbi complement C3d binding polypeptide is encoded by a polynucleotide which encodes an amino acid having at least 80%, 85%, 90%, 91%, 92%, 93%, 94%, 95%, 96%, 97%, or 100% identity to the amino acid sequence of SEQ ID NO: 56. Due to degeneracy in the genetic code, those of ordinary skill in the art would understand that other DNA sequences (including codon-optimized sequences) could encode these polypeptides, as well as the others disclosed herein.

Fusion Polypeptides

This disclosure provides fusion polypeptides comprising (i) a fragment antigen or antigen variant that comprises an epitope of a target protein antigen; and (ii) a complement C3d-binding polypeptide from an immunoglobulin-binding protein (Sbi) of *Staphylococcus aureus*. Exemplary fusion polypeptides disclosed herein are provided in Tables 1 and 2.

In some embodiments, the fragment antigen, antigen variant or fragment antigen variant has an amino acid sequence at least 80%, 85%, 90%, 91%, 92%, 93%, 94%, 95%, 96%, 97%, 98%, 99% or 100% identity to the amino acid sequence of SEQ ID NO: 3.

In some embodiments, the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 4.

In some embodiments, the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 5.

In some embodiments, the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 6.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 7.

In some embodiments, the fragment antigen, antigen variant or fragment antigen variant has at least 80%, 85%, 90%, or 100% identity to the amino acid sequence of SEQ ID NO: 8.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 20.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 21.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 22.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 23.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 24.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 25.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO:26.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 27.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 28.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 29.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 30.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 31.

In some embodiments, (a) and (b) are contiguous or separated by a linker. In some embodiments, the linker is a peptidyl linker. In some embodiments, the peptidyl linker comprises at least 60% glycine and/or serine. In some embodiments, the linker is chosen from a Gly-Gly-Gly-Gly-Ser (Gly4-Ser) linker (SEQ ID NO: 60), or a Histidine linker. In some embodiments, the linker is a Gly4-Ser linker (SEQ ID NO: 60). In some embodiments, the linker comprises 1, 2, 3, 4, 5, 6, 7, 8, 9, or 10 repeats of the Gly4-Ser linker (SEQ ID NO: 61). In some embodiments, the linker comprises 3 repeats of the Gly4-Ser linker (SEQ ID NO: 11). In some embodiments, the linker comprises the sequence of SEQ ID NO: 11.

In some embodiments, the polypeptide further comprises a secretion peptide. In some embodiments, the secretion peptide is about 10-30 amino acids in length. In some embodiments, the secretion peptide is about 10, 11, 12, 13, 14, 15, 16, 17, 18, 19, 20, 21, 22, 23, 24, 25, 26, 27, 28, 29 or 30 amino acids in length. In some embodiments, the secretion peptide comprises an amino acid having at least 80%, 85%, 90%, or 100% identity to the amino acid sequence of SEQ ID NO: 1. In some embodiments, the secretion peptide comprises an amino acid having at least 80%, 85%, 90%, or 100% identity to the amino acid sequence of SEQ ID NO: 2.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 12.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 13.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 14.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 15.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 16.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 17.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 18.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 19.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 32.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 33.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 34.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:35.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:36.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:37.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:38.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:39.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:40.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:41.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:42.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 43.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 44.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 45

TABLE 1

Exemplary amino acid sequences of components of polypeptide fusions disclosed herein

| SEQ ID NO | Feature | Amino acid sequence |
|---|---|---|
| 1 | Human IL-2 secretion peptide | MYRMQLLSCIALSLALVTNS |
| 2 | SARS-CoV-2 Spike residues 1-13 (secretion peptide) | MFVFLVLLPLVSS |
| 3 | SARS-CoV-2 Spike residues 331-527 (RBD domain) | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSNNLDSKVGGNYNYLYRLFRKSNL KPFERDISTEIYQAGSTPCNGVEGFNCYFPLQSY GFQPTNGVGYQPYRVVVLSFELLHAPATVCGP |
| 4 | SARS-CoV-2 Spike residues 410-527(portion of RBD domain) | IAPGQTGKIADYNYKLPDDFTGCVIAWNSNNL DSKVGGNYNYLYRLFRKSNLKPFERDISTEIYQ AGSTPCNGVEGFNCYFPLQSYGFQPTNGVGYQ PYRVVVLSFELLHAPATVCGP |
| 5 | SARS-CoV-2 Spike residues 430-527(portion of RBD domain) | TGCVIAWNSNNLDSKVGGNYNYLYRLFRKSNL KPFERDISTEIYQAGSTPCNGVEGFNCYFPLQSY GFQPTNGVGYQPYRVVVLSFELLHAPATVCGP |

TABLE 1-continued

Exemplary amino acid sequences of components of polypeptide fusions disclosed herein

| SEQ ID NO | Feature | Amino acid sequence |
|---|---|---|
| 6 | SARS-CoV-2 Spike residues 438-527 (portion of RBD domain) | SNNLDSKVGGNYNYLYRLFRKSNLKPFERDISTEIYQAGSTPCNGVEGFNCYFPLQSYGFQPTNGVGYQPYRVVVLSFELLHAPATVCGP |
| 7 | SARS-CoV-2 Spike residues 480-527 (portion of RBD domain) | CNGVEGFNCYFPLQSYGFQPTNGVGYQPYRVVVLSFELLHAPATVCGP |
| 8 | SARS-CoV-2 Spike residues 528-537 | KKSTNLVKNK |
| 9 | Domain III of Sbi from *S. aureus* strain Mu50 | IENADKAIKDFQDNKAPHDKSAAYEANSKLPKDLRDKNNRFV |
| 10 | Domain IV of Sbi from *S. aureus* strain Mu50 | EKVSIEKAIVRHDERVKSANDAISKLNEKDSIENRRLAQREVNKAPMDVKEHLQKQLD |
| 11 | Gly4 Ser linker | GGGGSGGGGSGGGGS |
| 20 | SARS-CoV-2 Spike residues 331-527 (RBD domain) - variant 1 | NITNLCPFGEVFNATRFASVYAWNRKRISNCVADYSVLYNSASFSTFKCYGVSPTKLNDLCFTNVYADSFVIRGDEVRQIAPGQTGKIADYNYSLPDDFTGCVIAWNSNNLDSKVGGNYNYLYRLFRKSNLKPFERDISTEIYQAGSTPCNGVEGFNCYFPLQSYGFQPTNGVGYQPYRVVVLSFELLHAPATVCGP |
| 21 | SARS-CoV-2 Spike residues 331-527 (RBD domain) - variant 2 | NITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSSNLDSKVGGNYNYLYRLFRKSNLKPFERDISTEIYQAGSTPCNGVEGFNCYFPLQSYGFQPTNGVGYQPYRVVVLSFELLHAPATVCGP |
| 22 | SARS-CoV-2 Spike residues 331-527 (RBD domain) - variant 3 | NITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNTDSKVGGNYNYLYRLFRKSNLKPFERDISTEIYQAGSTPCNGVEGFNCYFPLQSYGFQPTNGVGYQPYRVVVLSFELLHAPATVCGP |
| 23 | SARS-CoV-2 Spike residues 331-527 (RBD domain) - variant 4 | NITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLSSKVGGNYNYLYRLFRKSNLKPFERDISTEIYQAGSTPCNGVEGFNCYFPLQSYGFQPTNGVGYQPYRVVVLSFELLHAPATVCGP |
| 24 | SARS-CoV-2 Spike residues 331-527 (RBD domain) - variant 5 | NITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYSYLYRLFRKSNLKPFERDISTEIYQAGSTPCNGVEGFNCYFPLQSYGFQPTNGVGYQPYRVVVLSFELLHAPATVCGP |
| 25 | SARS-CoV-2 Spike residues 331-527 (RBD domain) - variant 6 | NITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYTYRLFRKSNLKPFERDISTEIYQAGSTPCNGVEGFNCYFPLQSYGFQPTNGVGYQPYRVVVLSFELLHAPATVCGP |
| 26 | SARS-CoV-2 Spike residues 331-527 (RBD domain) - variant 7 | NITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLSPFERDISTEIYQAGSTPCNGVEGFNCYFPLQSYGFQPTNGVGYQPYRVVVLSFELLHAPATVCGP |
| 27 | SARS-CoV-2 Spike residues 331-527 (RBD domain) - variant 8 | NITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLKPFERDISTEIYQAGSTPCNGTEGFNCYFPLQSYGFQPTNGVGYQPYRVVVLSFELLHAPATVCGP |

TABLE 1-continued

Exemplary amino acid sequences of components of polypeptide fusions disclosed herein

| SEQ ID NO | Feature | Amino acid sequence |
|---|---|---|
| 28 | SARS-CoV-2 Spike residues 331-527 (RBD domain) - variant 9 | NITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLKPFERDISTEIYQAGSTPCNGVEGFNCTFPLQSYGFQPTNGVGYQPYRVVVLSFELLHAPATVCGP |
| 29 | SARS-CoV-2 Spike residues 331-527 (RBD domain) - variant 10 | NITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLKPFERDISTEIYQAGSTPCNGVEGFNCYFPLQSYGFQPTNGTGYQPYRVVVLSFELLHAPATVCGP |
| 30 | SARS-CoV-2 Spike residues 331-527 (RBD domain) - variant 11 | NITNLCPFAEVFNATRFASVAAWNAKAISNCVADYSVLYNSASFSTFKCYGVAPTKLNAACFTNVYADSFVIRGAEVRQIAPGQTGKIADYNYKLPDDFTGCVIAWNSNNLDSKVGGNYNYLYRLFRKSNLKPFERDISTEIYQAGSTPCNGVEGFNCYFPLQSYGFQPTNGVGYQPYRVVVLSFELLAAPATVCGP |
| 31 | SARS-CoV-2 Spike residues 331-527 (RBD domain) - variant 12 | NITNLCAFGEVFNAARFASVYAWNRKRISNCAAAYSAAYNSASFSAFKCAGVAPTKLNDLCFTAVYADAFAIRAAAVRQAAPAQAGKIADYNYKLPDDFTGCVIAWNSNNLDSKVGGNYNYLYRLFRKSNLKPFERDISTEIYQAGSTPCNGVEGFNCYFPLQSYGFQPTNGVGYQPYRVVVLAFELLHAPATACGP |

TABLE 2

Exemplary amino acid sequences of polypeptide fusions encoded by polynucleotide sequences disclosed herein

| SEQ ID NO | Feature | Amino acid sequence |
|---|---|---|
| 12 | IL2(ss)-RBD | MYRMQLLSCIALSLALVTNSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLKPFERDISTEIYQAGSTPCNGVEGFNCYFPLQSYGFQPTNGVGYQPYRVVVLSFELLHAPATVCGPKKSTNLVKNK |
| 13 | IL2(ss)-RBD-Sbi(III-IV) | MYRMQLLSCIALSLALVTNSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLKPFERDISTEIYQAGSTPCNGVEGFNCYFPLQSYGFQPTNGVGYQPYRVVVLSFELLHAPATVCGPKKSTNLVKNKGGGGSGGGGSGGGGSIENADKAIKDFQDNKAPHDKSAAYEANSKLPKDLRDKNNRFVEKVSIEKAIVRHDERVKSANDAISKLNEKDSIENRRLAQREVNKAPMDVKEHLQKQLD |
| 14 | S(ss)-RBD-Sbi(III-IV) | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLKPFERDISTEIYQAGSTPCNGVEGFNCYFPLQSYGFQPTNGVGYQPYRVVVLSFELLHAPATVCGPGGGGSGGGGSGGGGSIENADKAIKDFQDNKAPHDKSAAYEANSKLPKDLRDKNNRFVEKVSIEKAIVRHDERVKSANDAISKLNEKDSIENRRLAQREVNKAPMDVKEHLQKQLD |
| 15 | RBDΔ1-Sbi(III-IV) | MYRMQLLSCIALSLALVTNSAAIAPGQTGKIADYNYKLPDDFTGCVIAWNSNNLDSKVGGNYNYLYRLFRKSNLKPFERDISTEIYQAGSTPCNGVEGFNCYFPLQSYGFQPTNGVGYQPYRVVVLSFELLHAPATVCGPKKSTNLVKNKGGGGSGGGGSGGGGSIENADKAIKDFQDNKAPHDKSAAYEANSKLPKDLRDKNNRF |

TABLE 2-continued

Exemplary amino acid sequences of polypeptide fusions encoded by polynucleotide sequences disclosed herein

| SEQ ID NO | Feature | Amino acid sequence |
|---|---|---|
| | | VEKVSIEKAIVRHDERVKSANDAISKLNEKDSIENRRLAQREVNKAPMDVKEHLQKQLD |
| 16 | RBDΔ2-Sbi(III-IV) | MYRMQLLSCIALSLALVTNSAATGCVIAWNSNNLDSKVGGNYNYLYRLFRKSNLKPFERDISTEIYQAGSTPCNGVEGFNCYFPLQSYGFQPTNGVGYQPYRVVVLSFELLHAPATVCGPKKSTNLVKNKGGGGSGGGGSGGGGSIENADKAIKDFQDNKAPHDKSAAYEANSKLPKDLRDKNNRFVEKVSIEKAIVRHDERVKSANDAISKLNEKDSIENRRLAQREVNKAPMDVKEHLQKQLD |
| 17 | RBDΔ3-Sbi(III-IV) | MYRMQLLSCIALSLALVTNSAASNNLDSKVGGNYNYLYRLFRKSNLKPFERDISTEIYQAGSTPCNGVEGFNCYFPLQSYGFQPTNGVGYQPYRVVVLSFELLHAPATVCGPKKSTNLVKNKGGGGSGGGGSGGGGSIENADKAIKDFQDNKAPHDKSAAYEANSKLPKDLRDKNNRFVEKVSIEKAIVRHDERVKSANDAISKLNEKDSIENRRLAQREVNKAPMDVKEHLQKQLD |
| 18 | RBDΔ4-Sbi(III-IV) | MYRMQLLSCIALSLALVTNSAACNGVEGFNCYFPLQSYGFQPTNGVGYQPYRVVVLSFELLHAPATVCGPKKSTNLVKNKGGGGSGGGGSGGGGSIENADKAIKDFQDNKAPHDKSAAYEANSKLPKDLRDKNNRFVEKVSIEKAIVRHDERVKSANDAISKLNEKDSIENRRLAQREVNKAPMDVKEHLQKQLD |
| 19 | RBDΔ5-Sbi(III-IV) | MYRMQLLSCIALSLALVTNSAATNVYADSFVIRGDEVRQIAPGQTGKIADYNYKLPDDFTGCVIAWNSNNLDSKVGGNYNYLYRLFRKSNLKPFERDISTEIYQAGSTPCNGVEGFNCYFPLQSYGFQPTNGVGYQPYRVVVLSFELKKSTNLVKNKGGGGSGGGGSGGGGSIENADKAIKDFQDNKAPHDKSAAYEANSKLPKDLRDKNNRFVEKVSIEKAIVRHDERVKSANDAISKLNEKDSIENRRLAQREVNKAPMDVKEHLQKQLD |
| 32 | S(ss)-RBD-1 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYSLPDDFTGCVIAWNSNNLDSKVGGNYNYLYRLFRKSNLKPFERDISTEIYQAGSTPCNGVEGFNCYFPLQSYGFQPTNGVGYQPYRVVVLSFELLHAPATVCGP |
| 33 | S(ss)-RBD-2 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSSNLDSKVGGNYNYLYRLFRKSNLKPFERDISTEIYQAGSTPCNGVEGFNCYFPLQSYGFQPTNGVGYQPYRVVVLSFELLHAPATVCGP |
| 34 | S(ss)-RBD-3 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNTDSKVGGNYNYLYRLFRKSNLKPFERDISTEIYQAGSTPCNGVEGFNCYFPLQSYGFQPTNGVGYQPYRVVVLSFELLHAPATVCGP |
| 35 | S(ss)-RBD-4 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLSSKVGGNYNYLYRLFRKSNLKPFERDISTEIYQAGSTPCNGVEGFNCYFPLQSYGFQPTNGVGYQPYRVVVLSFELLHAPATVCGP |
| 36 | S(ss)-RBD-5 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYSYLYRLFRKSNLKPFERDISTEIYQAGSTPCNGVEGFNCYFPLQSYGFQPTNGVGYQPYRVVVLSFELLHAPATVCGP |
| 37 | S(ss)-RBD-6 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYTYRLFRKSNLKPFERDISTEIYQAGSTPCNGVEGFNCYFPLQSYGFQPTNGVGYQPYRVVVLSFELLHAPATVCGP |

TABLE 2-continued

Exemplary amino acid sequences of polypeptide fusions encoded by polynucleotide sequences disclosed herein

| SEQ ID NO | Feature | Amino acid sequence |
|---|---|---|
| 38 | S(ss)-RBD-7 | MFVFLVLLPLVSSAANITNLCPFGEVFNATRFASVYAWNRKR<br>ISNCVADYSVLYNSASFSTFKCYGVSPTKLNDLCFTNVYADS<br>FVIRGDEVRQIAPGQTGKIADYNYKLPDDFTGCVIAWNSNNL<br>DSKVGGNYNYLYRLFRKSNLSPFERDISTEIYQAGSTPCNGV<br>EGFNCYFPLQSYGFQPTNGVGYQPYRVVVLSFELLHAPATV<br>CGP |
| 39 | S(ss)-RBD-8 | MFVFLVLLPLVSSAANITNLCPFGEVFNATRFASVYAWNRKR<br>ISNCVADYSVLYNSASFSTFKCYGVSPTKLNDLCFTNVYADS<br>FVIRGDEVRQIAPGQTGKIADYNYKLPDDFTGCVIAWNSNNL<br>DSKVGGNYNYLYRLFRKSNLKPFERDISTEIYQAGSTPCNGT<br>EGFNCYFPLQSYGFQPTNGVGYQPYRVVVLSFELLHAPATV<br>CGP |
| 40 | S(ss)-RBD-9 | MFVFLVLLPLVSSAANITNLCPFGEVFNATRFASVYAWNRKR<br>ISNCVADYSVLYNSASFSTFKCYGVSPTKLNDLCFTNVYADS<br>FVIRGDEVRQIAPGQTGKIADYNYKLPDDFTGCVIAWNSNNL<br>DSKVGGNYNYLYRLFRKSNLKPFERDISTEIYQAGSTPCNGV<br>EGFNCTFPLQSYGFQPTNGVGYQPYRVVVLSFELLHAPATVC<br>GP |
| 41 | S(ss)-RBD-10 | MFVFLVLLPLVSSAANITNLCPFGEVFNATRFASVYAWNRKR<br>ISNCVADYSVLYNSASFSTFKCYGVSPTKLNDLCFTNVYADS<br>FVIRGDEVRQIAPGQTGKIADYNYKLPDDFTGCVIAWNSNNL<br>DSKVGGNYNYLYRLFRKSNLKPFERDISTEIYQAGSTPCNGV<br>EGFNCYFPLQSYGFQPTNGTGYQPYRVVVLSFELLHAPATVC<br>GP |
| 42 | S(ss)-RBD-11 | MFVFLVLLPLVSSAANITNLCPFAEVFNATRFASVAAWNAK<br>AISNCVADYSVLYNSASFSTFKCYGVAPTKLNAACFTNVYA<br>DSFVIRGAEVRQIAPGQTGKIADYNYKLPDDFTGCVIAWNSN<br>NLDSKVGGNYNYLYRLFRKSNLKPFERDISTEIYQAGSTPCN<br>GVEGFNCYFPLQSYGFQPTNGVGYQPYRVVVLSFELLAAPA<br>TVCGP |
| 43 | S(ss)-RBD-12 | MFVFLVLLPLVSSAANITNLCAFGEVFNAARFASVYAWNRK<br>RISNCAAAYSAAYNSASFSAFKCAGVAPTKLNDLCFTAVYA<br>DAFAIRAAAVRQAAPAQAGKIADYNYKLPDDFTGCVIAWNS<br>NNLDSKVGGNYNYLYRLFRKSNLKPFERDISTEIYQAGSTPC<br>NGVEGFNCYFPLQSYGFQPTNGVGYQPYRVVVLAFELLHAP<br>ATACGP |
| 44 | S(ss)-MERS-CoV Spike RBD-SARS-CoV-2 Spike ACE binding RBD | MFVFLVLLPLVSSAAEGVECDFSPLLSGTPPQVYNFKRLVFT<br>NCNYNLTKLLSLFSVNDFTCSQISPAAIASNCYSSLIL**DSFVIR**<br>**GDEVRQIAPGQTGKIADYNYKLPDDFTGCVIAWNSNNLD**<br>**SKVGGNYNYLYRLFRKSNLKPFERDISTEIYQAGSTPCNG**<br>**VEGFNCYFPLQSYGFQPTNGVGYQPYRVVVLSFELLHAP**<br>**ATVCPK** |
| 45 | S(ss)-SARS-CoV-2 Spike ACE binding RBD-MERS-CoV Spike RBD | MFVFLVLLPLVSSAAEGVECDFSPLLSGTPPQVYNFKRLVFT<br>NCNYNLTKLLSLFSVNDFTCSQISPAAIASNCYSSLILDYFSYP<br>LSMKSDLSVSSAGPISQFNYKQSFSNPTCLILATVPHNLTTITK<br>PLKYSYFNKCSRFLSDDRTEVPQLVNANQY**TPCNGVEGFNC**<br>**YFPLQSYGFQPTNGVGYQPYRVVVLSFELLHAPATV**CPK |

Fusion Polynucleotide

Among other things, the disclosure provides fusion polynucleotides encoding fusion polypeptides comprising (i) a fragment antigen or antigen variant that comprises an epitope of a target protein antigen; and (ii) a complement C3d-binding polypeptide from an immunoglobulin-binding protein (Sbi) of *Staphylococcus aureus*. Exemplary fusion polynucleotide sequences are provided in Table 3.

In some embodiments, (a) and (b) are encoded by a nucleotide sequence and are disposed in the same nucleotide sequence or in different nucleotide sequences. In some embodiments, (a) is disposed N-terminus of (b). In some embodiments, (a) is disposed C-terminus of (b).

In some embodiments, (a) is disposed C-terminus of (b). In some embodiments, (a) and (b) are contiguous or separated by a nucleotide sequence encoding a linker. In some embodiments, the linker is a peptidyl linker. In some embodiments, the peptidyl linker comprises at least 60% glycine and/or serine. In some embodiments, the linker is chosen from a Gly-Gly-Gly-Gly-Ser (Gly4-Ser) linker, or a Histidine linker.

In some embodiments, a fusion polynucleotide further comprises a nucleotide sequence encoding a secretion peptide.

In some embodiments, a fusion polynucleotide is or comprises RNA. In some embodiments, a fusion polynucleotide is or comprises messenger RNA.

In some embodiments, a fusion polynucleotide is or comprises DNA.

In some embodiments, a fusion polynucleotide encodes a fragment antigen which is characterized in that when expressed in vivo, it binds to a Major Histocompatibility Complex (MHC) molecule. In some embodiments, a MHC molecule is or comprises a MHC I molecule or a MHC II molecule.

In some embodiments, a fusion polynucleotide encodes a fragment antigen which is characterized in that when expressed in vivo, it does not bind to a MHC molecule.

In some embodiments, a fusion polynucleotide encodes a fragment antigen which is characterized in that when expressed in vivo, it folds into a three-dimensional conformation that is substantially identical to the three-dimensional conformation of the fragment antigen as it is in its native position in the target protein antigen.

In some embodiments, a fusion polynucleotide encodes a fragment antigen, antigen variant or fragment antigen variant which further comprises an amino acid sequence from a second target protein antigen.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 46.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 47.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 48.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 49.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 50.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 51.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 52.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 53.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 54.

TABLE 3

Exemplary polynucleotide sequences disclosed herein

| SEQ ID NO | Feature | Nucleic acid sequence |
|---|---|---|
| 46 | IL2(ss)-RBD | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaaatatcacaaatctctgccctttcggggaggtcttcaacgcaacccggttcgcatca<br>gtgtacgcctggaatcgcaaacggatttctaactgtgtagccgattattctgtgctgtacaacagtg<br>ctagtttttctaccttcaaatgttatggagtatccccaaccaagcttaacgatctttgttttacaaacgt<br>ctacgcagacagctttgtcatcaggggggacgaagttcgccaaattgctccagggcagacaggt<br>aaaattgcagactataattacaaactcccagacgacttcaccggctgtgttatcgcttggaacagt<br>aacaatcttgacagcaaggtcggtggcaactataattatctctatcgacttttccgaaaatccaattt<br>gaagccctttgagagggacatttcaaccgaaatataccaggctggatcaactccttgcaatggtgt<br>cgaaggatttaactgttacttccccttgcagagttacgggtttcagccaaccaatggggtggggta<br>tcaaccataccgggtcgttgtattgagtttcgaactgttgcatgctccagcaacagtatgtggtccc<br>aaaaagagtacaaatctggtgaaaaacaaaTAATGATAGACCAGCCTCAAG<br>AACACCCGAATGGAGTCTCTAAGCTACATAATACCAACTT<br>ACACTTTACAAAATGTTGTCCCCCAAAATGTAGCCATTCG<br>TATCTGCTCCTAATAAAAAGAAAGTTTCTTCACATTCT |
| 47 | IL2(ss)-RBD-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaaatatcacaaatctctgccctttcggggaggtcttcaacgcaacccggttcgcatca<br>gtgtacgcctggaatcgcaaacggatttctaactgtgtagccgattattctgtgctgtacaacagtg<br>ctagtttttctaccttcaaatgttatggagtatccccaaccaagcttaacgatctttgttttacaaacgt<br>ctacgcagacagctttgtcatcaggggggacgaagttcgccaaattgctccagggcagacaggt<br>aaaattgcagactataattacaaactcccagacgacttcaccggctgtgttatcgcttggaacagt<br>aacaatcttgacagcaaggtcggtggcaactataattatctctatcgacttttccgaaaatccaattt<br>gaagccctttgagagggacatttcaaccgaaatataccaggctggatcaactccttgcaatggtgt<br>cgaaggatttaactgttacttccccttgcagagttacgggtttcagccaaccaatggggtggggta<br>tcaaccataccgggtcgttgtattgagtttcgaactgttgcatgctccagcaacagtatgtggtccc<br>aaaaagagtacaaatctggtgaaaaacaaaggtgggggtggaagtggtgggggaggctctgg<br>cggaggaggaagcatagagaacgcagataaggccataaaggattttcaggataacaaggccc<br>cccacgacaagtccgccgcatacgaagcaaattccaagttgccaaaggatttgcgagacaaaa<br>acaatcgctttgtagagaaagtttcaattgaaaaagcaattgtaaggcatgacgaacgggtgaag<br>agtgctaacgatgcaataagtaagctgaacgagaaagactcaattgagaaccgaaggttggctc<br>aacgcgaggtcaacaaggcaccaatggacgtgaaagagcatctgcaaaagcaacttgacTA |

TABLE 3-continued

Exemplary polynucleotide sequences disclosed herein

| SEQ ID NO | Feature | Nucleic acid sequence |
|---|---|---|
| | | ATGATAGACCAGCCTCAAGAACACCCGAATGGAGTCTCTA<br>AGCTACATAATACCAACTTACACTTTACAAAATGTTGTCC<br>CCCAAAATGTAGCCATTCGTATCTGCTCCTAATAAAAAGA<br>AAGTTTCTTCACATTCT |
| 48 | S(ss)-RBD | CTTGTTCTTTTTGCAGAAGCTCAGAATAAACGCTCAACTTT<br>GGCCACCatgttcgtatttctggtacttctccccttgttagttccgcagcaaatatcaccaatc<br>tttgccctttcggagaggtattcaatgcaactcggtttgcaagtgtgtacgcttggaatcgcaagcg<br>catcagcaattgcgtcgctgattacagtgtgctctataacagtgcatctttctccactttcaagtgtta<br>cggtgttagtccaactaagctgaacgatctttgttttaccaacgtgtacgctgattctttcgtcattcg<br>aggggatgaggtgcgacaaatagcacctgggcaaaccgggaaaatagcagactataattataa<br>gctcccagatgacttcactgggtgcgtaattgcctggaatagcaacaatcttgacagtaaagtag<br>gggaaattacaactatttgtacagattgtttcgcaaatccaatttgaagccatttgagcgcgacat<br>ctctactgagatttatcaggctggcagcactccttgtaacggtgtagaaggctttaactgttatttcc<br>cccttcaatcttatgggtttcagcccaccaatggcgtgggataccagccttatcgcgtcgttgtactt<br>agttttgaactgcttcatgctccagctacagtgtgcggccccTAATGATAGACCAGC<br>CTCAAGAACACCCGAATGGAGTCTCTAAGCTACATAATAC<br>CAACTTACACTTTACAAAATGTTGTCCCCCAAAATGTAGC<br>CATTCGTATCTGCTCCTAATAAAAAGAAAGTTTCTTCACAT<br>TCT |
| 49 | S(ss)-RBD-Sbi(III-IV) | CTTGTTCTTTTTGCAGAAGCTCAGAATAAACGCTCAACTTT<br>GGCCACCatgttcgtatttctggtacttctccccttgttagttccgcagcaaatatcaccaatc<br>tttgccctttcggagaggtattcaatgcaactcggtttgcaagtgtgtacgcttggaatcgcaagcg<br>catcagcaattgcgtcgctgattacagtgtgctctataacagtgcatctttctccactttcaagtgtta<br>cggtgttagtccaactaagctgaacgatctttgttttaccaacgtgtacgctgattctttcgtcattcg<br>aggggatgaggtgcgacaaatagcacctgggcaaaccgggaaaatagcagactataattataa<br>gctcccagatgacttcactgggtgcgtaattgcctggaatagcaacaatcttgacagtaaagtag<br>gggaaattacaactatttgtacagattgtttcgcaaatccaatttgaagccatttgagcgcgacat<br>ctctactgagatttatcaggctggcagcactccttgtaacggtgtagaaggctttaactgttatttcc<br>cccttcaatcttatgggtttcagcccaccaatggcgtgggataccagccttatcgcgtcgttgtactt<br>agttttgaactgcttcatgctccagctacagtgtgcggccccggtgggggtggaagtggtgggg<br>gaggctctggcggaggaggaagcatagagaacgcagataaggccataaaggattttcaggata<br>acaaggcccccccacgacaagtccgccgcatacgaagcaaattccaagttgccaaaggatttgc<br>gagacaaaaacaatcgctttgtagagaaagtttcaattgaaaaagcaattgtaaggcatgacgaa<br>cgggtgaagagtgctaacgatgcaataagtaagctgaacgagaaagactcaattgagaaccga<br>aggttggctcaacgcgaggtcaacaaggcaccaatggacgtgaaagagcatctgcaaaagca<br>acttgacTAATGATAGACCAGCCTCAAGAACACCCGAATGGA<br>GTCTCTAAGCTACATAATACCAACTTACACTTTACAAAAT<br>GTTGTCCCCCAAAATGTAGCCATTCGTATCTGCTCCTAATA<br>AAAAGAAAGTTTCTTCACATTCT |
| 50 | RBDΔ1-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaattgctccagggcagacaggtaaaattgcagactataattacaaactcccagacga<br>cttcaccggctgtgttatcgcttggaacagtaacaatcttgacagcaaggtcggtggcaactataa<br>ttatctctatcgacttttccgaaaatccaatttgaagccctttgagagggacatttcaaccgaaatata<br>ccaggctggatcaactccttgcaatggtgtcgaaggatttaactgttacttccccttgcagagttac<br>gggtttcagccaaccaatggggtggggtatcaaccataccgggtcgttgtattgagtttcgaactg<br>ttgcatgctccagcaacagtatgtggtcccaaaaagagtacaaatctggtgaaaaacaaaggtg<br>gggtggaagtggtgggggaggctctggcggaggaggaagcatagagaacgcagataagg<br>ccataaaggattttcaggataacaaggcccccccacgacaagtccgccgcatacgaagcaaattc<br>caagttgccaaaggatttgcgagacaaaaacaatcgctttgtagagaaagtttcaattgaaaaag<br>caattgtaaggcatgacgaacgggtgaagagtgctaacgatgcaataagtaagctgaacgaga<br>aagactcaattgagaaccgaaggttggctcaacgcgaggtcaacaaggcaccaatggacgtga<br>aagagcatctgcaaaagcaacttgacTAATGATAGACCAGCCTCAAGAA<br>CACCCGAATGGAGTCTCTAAGCTACATAATACCAACTTAC<br>ACTTTACAAAATGTTGTCCCCCAAAATGTAGCCATTCGTA<br>TCTGCTCCTAATAAAAAGAAAGTTTCTTCACATTCT |
| 51 | RBDΔ2-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaaccggctgtgttatcgcttggaacagtaacaatcttgacagcaaggtcggtggcaa<br>ctataattatctctatcgacttttccgaaaatccaatttgaagccctttgagagggacatttcaaccga<br>aatataccaggctggatcaactccttgcaatggtgtcgaaggatttaactgttacttccccttgcag<br>agttacgggtttcagccaaccaatggggtggggtatcaaccataccgggtcgttgtattgagtttc<br>gaactgttgcatgctccagcaacagtatgtggtcccaaaaagagtacaaatctggtgaaaaacaa<br>aggtgggggtggaagtggtgggggaggctctggcggaggaggaagcatagagaacgcagat<br>aaggccataaaggattttcaggataacaaggcccccccacgacaagtccgccgcatacgaagca<br>aattccaagttgccaaaggatttgcgagacaaaaacaatcgctttgtagagaaagtttcaattgaa<br>aaagcaattgtaaggcatgacgaacgggtgaagagtgctaacgatgcaataagtaagctgaac<br>gagaaagactcaattgagaaccgaaggttggctcaacgcgaggtcaacaaggcaccaatgga<br>cgtgaaagagcatctgcaaaagcaacttgacTAATGATAGACCAGCCTCAA<br>GAACACCCGAATGGAGTCTCTAAGCTACATAATACCAACT |

TABLE 3-continued

Exemplary polynucleotide sequences disclosed herein

| SEQ ID NO | Feature | Nucleic acid sequence |
|---|---|---|
| | | TACACTTTACAAAATGTTGTCCCCCAAAATGTAGCCATTC<br>GTATCTGCTCCTAATAAAAAGAAAGTTTCTTCACATTCT |
| 52 | RBDΔ3-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaagtaacaatcttgacagcaaggtcggtggcaactataattatctctatcgacttttcc<br>gaaaatccaatttgaagccctttgagagggacatttcaaccgaaatataccaggctggatcaactc<br>cttgcaatggtgtcgaaggatttaactgttacttccccttgcagagttacgggtttcagccaaccaat<br>ggggtggggtatcaaccataccgggtcgttgtattgagtttcgaactgttgcatgctccagcaaca<br>gtatgtggtcccaaaaagagtacaaatctggtgaaaaacaaaggtgggggtggaagtggtggg<br>ggaggctctggcggaggaggaagcatagagaacgcagataaggccataaaggattttcagga<br>taacaaggcccccacgacaagtccgccgcatacgaagcaaattccaagttgccaaaggatttg<br>cgagacaaaaacaatcgctttgtagagaaagtttcaattgaaaaagcaattgtaaggcatgacga<br>acgggtgaagagtgctaacgatgcaataagtaagctgaacgagaaagactcaattgagaaccg<br>aaggttggctcaacgcgaggtcaacaaggcaccaatggacgtgaaagagcatctgcaaaagc<br>aacttgacTAATGATAGACCAGCCTCAAGAACACCCGAATGGA<br>GTCTCTAAGCTACATAATACCAACTTACACTTTACAAAAT<br>GTTGTCCCCCAAAATGTAGCCATTCGTATCTGCTCCTAATA<br>AAAAGAAAGTTTCTTCACATTCT |
| 53 | RBDΔ4-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcatgcaatggtgtcgaaggatttaactgttacttccccttgcagagttacgggtttcagc<br>caaccaatggggtggggtatcaaccataccgggtcgttgtattgagtttcgaactgttgcatgctc<br>cagcaacagtatgtggtcccaaaaagagtacaaatctggtgaaaaacaaaggtgggggtggaa<br>gtggtgggggaggctctggcggaggaggaagcatagagaacgcagataaggccataaagga<br>ttttcaggataacaaggcccccacgacaagtccgccgcatacgaagcaaattccaagttgcca<br>aaggatttgcgagacaaaaacaatcgctttgtagagaaagtttcaattgaaaaagcaattgtaagg<br>catgacgaacgggtgaagagtgctaacgatgcaataagtaagctgaacgagaaagactcaatt<br>gagaaccgaaggttggctcaacgcgaggtcaacaaggcaccaatggacgtgaaagagcatct<br>gcaaaagcaacttgacTAATGATAGACCAGCCTCAAGAACACCCG<br>AATGGAGTCTCTAAGCTACATAATACCAACTTACACTTTA<br>CAAAATGTTGTCCCCCAAAATGTAGCCATTCGTATCTGCT<br>CCTAATAAAAAGAAAGTTTCTTCACATTCT |
| 54 | RBDΔ5-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaacaaacgtctacgcagacagctttgtcatcagggggacgaagttcgccaaattg<br>ctccagggcagacaggtaaaattgcagactataattacaaactcccagacgacttcaccggctgt<br>gttatcgcttggaacagtaacaatcttgacagcaaggtcggtggcaactataattatctctatcgac<br>ttttccgaaaatccaatttgaagccctttgagagggacatttcaaccgaaatataccaggctggatc<br>aactccttgcaatggtgtcgaaggatttaactgttacttccccttgcagagttacgggtttcagccaa<br>ccaatggggtggggtatcaaccataccgggtcgttgtattgagtttcgaactgggtgggggtgga<br>agtggtgggggaggctctggcggaggaggaagcatagagaacgcagataaggccataaagg<br>attttcaggataacaaggcccccacgacaagtccgccgcatacgaagcaaattccaagttgcc<br>aaaggatttgcgagacaaaaacaatcgctttgtagagaaagtttcaattgaaaaagcaattgtaag<br>gcatgacgaacgggtgaagagtgctaacgatgcaataagtaagctgaacgagaaagactcaat<br>tgagaaccgaaggttggctcaacgcgaggtcaacaaggcaccaatggacgtgaaagagcatct<br>gcaaaagcaacttgacTAATGATAGACCAGCCTCAAGAACACCCG<br>AATGGAGTCTCTAAGCTACATAATACCAACTTACACTTTA<br>CAAAATGTTGTCCCCCAAAATGTAGCCATTCGTATCTGCT<br>CCTAATAAAAAGAAAGTTTCTTCACATTCT |

mRNA Encoding Polypeptides and Formulations Thereof

Among other things, provided herein are polypeptides and polynucleotides which can be used to stimulate an immune response against an antigen and/or to enhance immunogenicity of an antigen.

In some embodiments, a polypeptide disclosed herein is encoded by a polynucleotide comprising an RNA. In some embodiments, a polynucleotide comprises a messenger RNA.s In some embodiments, a polynucleotide comprising an RNA, e.g., mRNA, is formulated in a lipid nanoparticle (LNP) formulation.

In some embodiments, the disclosure provides an LNP formulation comprising a polynucleotide comprising an RNA, e.g., mRNA, for use in an immunogenic composition.

In some embodiments, an LNP formulation comprising a polynucleotide comprising an RNA, e.g., mRNA, is administered to a subject to enhance and/or modulate an immune response. In some embodiments, the immune response is elicited by an antigen comprised in the polynucleotide.

In some embodiments, an LNP formulation comprising a polynucleotide comprising an RNA, e.g., mRNA, is characterized in that when administered to a subject, it reduces immunogenicity to an antigen, e.g., an antigen comprised in a polynucleotide or an antigen comprised in a polypeptide.

In some embodiments, an LNP formulation comprising a polynucleotide comprising an RNA, e.g., mRNA, is characterized in that when administered to a subject it focuses the immune response on a conserved and/or functional region of an epitope of a target protein antigen.

In some embodiments, an LNP formulation comprising a polynucleotide comprising an RNA, e.g., mRNA, is characterized in that when administered to a subject it improves the breadth and/or efficacy of an immune response in the subject to a target protein antigen.

In some embodiments, an LNP formulation comprising a polynucleotide comprising an RNA, e.g., mRNA, is characterized in that when administered to a subject it results in a humoral response, e.g., a broadly neutralizing humoral response, and/or a T cell mediated response.

In some embodiments, a polypeptide disclosed herein comprises a fusion polypeptide as described herein. In some embodiments, a polynucleotide disclosed herein comprises a fusion polynucleotide as described herein. In some embodiments, a fusion polypeptide is encoded by a fusion polynucleotide comprising an RNA. In some embodiments, a fusion polynucleotide comprises a messenger RNA.

In some embodiments, a fusion polynucleotide comprising an RNA, e.g., mRNA, is formulated in a lipid nanoparticle (LNP) formulation.

In some embodiments, the disclosure provides an LNP formulation comprising a fusion polynucleotide comprising an RNA, e.g., mRNA, for use in an immunogenic composition.

In some embodiments, an LNP formulation comprising a fusion polynucleotide comprising an RNA, e.g., mRNA, is administered to a subject to enhance and/or modulate an immune response. In some embodiments, the immune response is elicited by a fragment antigen comprised in a fusion polynucleotide. In some embodiments, the immune response is enhanced by an adjuvant, e.g., C3d binding polypeptide, comprised in a fusion polynucleotide.

In some embodiments, an LNP formulation comprising a fusion polynucleotide comprising an RNA, e.g., mRNA, is characterized in that when administered to a subject, it reduces immunogenicity to an antigen, e.g., an antigen comprised in a fusion polynucleotide or an antigen comprised in a fusion polypeptide.

In some embodiments, an LNP formulation comprising a fusion polynucleotide comprising an RNA, e.g., mRNA, is characterized in that when administered to a subject it focuses the immune response on a conserved and/or functional region of an epitope of a target protein antigen.

In some embodiments, an LNP formulation comprising a fusion polynucleotide comprising an RNA, e.g., mRNA, is characterized in that when administered to a subject it improves the breadth and/or efficacy of an immune response in the subject to a target protein antigen.

In some embodiments, an LNP formulation comprising a fusion polynucleotide comprising an RNA, e.g., mRNA, is characterized in that when administered to a subject it results in a humoral response, e.g., a broadly neutralizing humoral response, and/or a T cell mediated response.

Compositions

Among other things, the present disclosure provides compositions. Compositions disclosed herein, e.g., compositions comprising a polypeptide or a polynucleotide disclosed herein, can focus the immune response on conserved and/or functional regions of an antigen. In some embodiments, this immunofocusing can improve the breadth and/or efficacy of an immune response against an antigen.

In some embodiments, a composition disclosed herein is characterized in that when administered to a subject, it reduces immunogenicity to an antigen, e.g., an antigen comprised in a fusion polynucleotide or an antigen comprised in a fusion polypeptide.

In some embodiments, a composition disclosed herein is characterized in that when administered to a subject it focuses the immune response on a conserved and/or functional region of an epitope of a target protein antigen.

In some embodiments, a composition disclosed herein is characterized in that when administered to a subject it improves the breadth and/or efficacy of an immune response in the subject to a target protein antigen.

In some embodiments, a composition disclosed herein is characterized in that when administered to a subject it results in a humoral response, e.g., a broadly neutralizing humoral response, and/or a T cell mediated response.

In some embodiments, a composition comprises a polypeptide as described herein, e.g., a fusion polypeptide as described herein. In some embodiments, a composition comprises a polynucleotide, e.g., a fusion polynucleotide as described herein.

In some embodiments, a composition is or comprises a pharmaceutical composition, e.g., as described herein.

In some embodiments, a composition is or comprises an expression vector comprising a polynucleotide disclosed herein, e.g., a fusion polynucleotide disclosed herein.

In some embodiments, a composition is or comprises an immunogenic composition, e.g., as described herein.

Immunogenic Compositions

Disclosed herein are immunogenic compositions comprising (1) an antigen fragment or an antigen variant comprising an epitope of a target protein antigen; and/or (2) an adjuvant comprising a complement C3d-binding region. In some embodiments, an immunogenic composition disclosed herein can enhance the titers of the resulting antibody response and/or result in a measurable T cell response.

In some embodiments, an immunogenic composition comprises an immunoglobulin-binding protein (Sbi) of *Staphylococcus aureus* for use as an adjuvant. In some embodiments, an immunogenic composition comprising Sbi for use as an adjuvant comprises an Sbi polypeptide or a fragment thereof. In some embodiments, an immunogenic composition comprising Sbi for use as an adjuvant comprises a polynucleotide encoding an Sbi polypeptide or a fragment thereof.

In some embodiments, an immunogenic composition comprises an antigen fragment or an antigen variant comprising an epitope of a target protein antigen, and an adjuvant comprising a complement C3d-binding polypeptide.

In some embodiments, an immunogenic composition comprises a fusion polypeptide comprising an antigen fragment or an antigen variant comprising an epitope of a target protein antigen fused to a complement C3d-binding polypeptide. In some embodiments, the C3d binding polypeptide comprises an immunoglobulin-binding protein (Sbi) of *Staphylococcus aureus*. In some embodiments, the complement C3d-binding polypeptide is or comprises one or both of domain III and domain IV of the Sbi of *Staphylococcus aureus*, or a functional fragment or a variant thereof.

In some embodiments, an immunogenic composition comprises a fusion polynucleotide encoding a fusion polypeptide comprising an antigen fragment or an antigen variant comprising an epitope of a target protein antigen fused to a complement C3d-binding polypeptide. In some embodiments, the fusion polynucleotide comprises a C3d binding polypeptide comprising an immunoglobulin-binding protein (Sbi) of *Staphylococcus aureus*. In some embodiments, the complement C3d-binding polypeptide is or comprises one or both of domain III and domain IV of the Sbi of *Staphylococcus aureus*, or a functional fragment or a variant thereof.

In some embodiments, an immunogenic composition comprises an expression vector comprising a polynucleotide or a fusion polynucleotide disclosed herein.

Pharmaceutical Compositions

Pharmaceutical compositions of the present disclosure may comprise a polypeptides disclosed herein (e.g., a fusion polypeptide), a polynucleotide disclosed herein (e.g., a fusion polynucleotide), or an expression vector comprising a polynucleotide (e.g., a fusion polynucleotide). In some embodiments, a pharmaceutical composition may comprise a pharmaceutically acceptable excipient, a diluent, or a combination thereof. In some embodiments, a pharmaceutical composition may comprise buffers such as neutral buffered saline, phosphate buffered saline and the like; carbohydrates such as glucose, mannose, sucrose, or dextrans; mannitol; proteins; polypeptides or amino acids such as glycine; antioxidants; chelating agents such as EDTA or glutathione; and preservatives.

In some embodiments, a pharmaceutical composition is formulated for administration according to any of the routes of administration disclosed herein. In some embodiments, a pharmaceutical composition is formulated for intramuscular administration, intradermal administration, intravenous administration, or subcutaneous administration.

Methods of Using Compositions Disclosed Herein

The disclosure provides, among other things, methods for using a fusion polypeptide described herein, a fusion polynucleotide described herein, or a composition comprising the same to stimulate an immune response against an antigen (e.g., as a vaccine), or to enhance immunogenicity of an antigen.

Also disclosed herein, are methods of using a fusion polypeptide described herein, a fusion polynucleotide described herein, or a composition comprising the same to treat a disease or ameliorating a symptom of a disease, e.g., a disease associated with an antigen described herein.

Use of compositions disclosed herein, e.g., compositions comprising a fusion polypeptide or a fusion polynucleotide disclosed herein, can focus the immune response on conserved and/or functional regions of an antigen. In some embodiments, this immunofocusing can improve the breadth and/or efficacy of an immune response against the antigen.

In some embodiments, a method comprising administering a composition disclosed herein results in reduced immunogenicity to an antigen, e.g., an antigen comprised in a the fusion polynucleotide or an antigen comprised in a fusion polypeptide.

In some embodiments, a method comprising administering a composition disclosed herein results in focusing of an immune response on a conserved and/or functional region of an epitope of a target protein antigen.

In some embodiments, a method comprising administering a composition disclosed herein results in improved breadth and/or efficacy of an immune response in a subject to a target protein antigen.

In some embodiments, a method comprising administering a composition disclosed herein results in a humoral response, e.g., a broadly neutralizing humoral response, and/or a T cell mediated response.

This disclosure provides a method comprising administering to a subject in need thereof at least one dose of a pharmaceutical composition comprising a fusion polypeptide disclosed herein, a fusion polynucleotide disclosed herein, or an expression vector comprising a fusion polynucleotide disclosed herein. In some embodiments, the at least one dose is administered in an effective amount to induce an immune response against the fragment antigen in the subject.

Disclosed herein is a method comprising administering to a subject: a first dose of a pharmaceutical composition disclosed herein; and a second dose of a pharmaceutical composition disclosed herein. In some embodiments, a pharmaceutical composition comprises a fusion polypeptide disclosed herein, a fusion polynucleotide disclosed herein, or an expression vector comprising a fusion polynucleotide disclosed herein.

In some embodiments, a first dose and a second dose are administered by at least 3 days, 4 days, 5 days, 6 days, 7 days, 2 weeks, 3 weeks, or 4 weeks apart.

In some embodiments, a first dose and a second dose are in the same amount. In some embodiments, a first dose and a second dose are in different amounts.

This disclosure provides, a method for enhancing the immunogenicity of an antigen, comprising administering to a subject in need thereof, a fusion polypeptide disclosed herein, or a fusion polynucleotide disclosed herein, or a pharmaceutical composition disclosed herein.

This disclosure also provides a method for stimulating an immune response against an antigen, comprising administering to a subject in need thereof, a fusion polypeptide disclosed herein, or a fusion polynucleotide disclosed herein, or a pharmaceutical composition disclosed herein.

Additionally provided herein is a method of treating a disease or ameliorating a symptom of a disease comprising administering to a subject in need thereof, a fusion polypeptide disclosed herein, or a fusion polynucleotide disclosed herein, or a pharmaceutical composition disclosed herein.

In some embodiments of any of the methods disclosed herein, a subject in need thereof is a subject who is suffering from or is susceptible to a disease, disorder, or condition induced by the target protein antigen. In some embodiments, a subject is a mammalian subject. In some embodiments, a subject is a human subject.

In some embodiments of any of the methods or uses disclosed herein, a single dose of the fusion polypeptide, fusion polynucleotide or pharmaceutical composition is administered. In some embodiments of any of the methods or uses disclosed herein, a plurality of doses of the fusion polypeptide, fusion polynucleotide or pharmaceutical composition is administered.

In some embodiments of any of the methods or uses disclosed herein, the fusion polypeptide, fusion polynucleotide or pharmaceutical composition is administered at a dose of about 0.5 micrograms to 10 micrograms.

In some embodiments of any of the methods or uses disclosed herein, administration of the fusion polynucleotide, fusion polypeptide or pharmaceutical composition results in a humoral response. In some embodiments, the humoral response is an antibody response.

In some embodiments of any of the methods or uses disclosed herein, administration of the fusion polynucleotide, fusion polypeptide or pharmaceutical composition results in an increased titer of an antibody response. In some embodiments, the increase in titer is an increase of about 10 fold to about 500 fold. In some embodiments, the increased titer of the antibody response is compared to administration of an otherwise similar fusion polynucleotide that does not comprise an Sbi domain III, or a fragment or variant thereof; and Sbi domain IV, or a fragment or a variant thereof. In some embodiments, the increased titer of the antibody response is compared to administration of an otherwise similar fusion polypeptide that does not comprise an Sbi domain III, or a fragment or variant thereof; and an Sbi domain IV, or a fragment or a variant thereof. In some embodiments, the increased titer of the antibody response is compared to administration of an otherwise similar pharmaceutical composition that does not comprise a nucleotide sequence encoding Sbi domain III, or a fragment or variant thereof; and Sbi domain IV, or a fragment or a variant thereof.

In some embodiments of any of the methods or uses disclosed herein, the composition is administered via any one of the following routes of administration: intramuscular, intravenous, subcutaneous, intrathecal, intradermal, ocular, intranasal, sublingual, or oral.

Method of Screening for Fragment Antigen

Also provided herein is an in vitro method of selecting a fragment antigen by identifying a polypeptide fragment that folds into a three-dimensional conformation that is substantially identical to the three-dimensional conformation as in a target protein antigen from which the fragment is derived. In some embodiments, a screening method disclosed herein can identify an antigen or a fragment antigen which extend the design space of effective antigens. In some embodiments, a screening method disclosed herein can identify an antigen or a fragment antigen that lacks a T cell epitope, or that has a portion of a T cell epitope. In some embodiments, a screening method disclosed herein can identify a fragment antigen which contains only a portion of an epitope of a target protein antigen.

In some embodiments, the method comprises the steps of: providing a mammalian cell display system that displays a library of fragment antigen candidates on cell surface; exposing the mammalian cell display system to a composition comprising antibodies that bind to a target protein antigen from which the fragment antigen candidates are derived; detecting fragment antigen candidates that bind to the target protein antigen-binding antibodies, wherein the binding of a fragment antigen candidate that binds to at least one of the target protein antigen-binding antibodies is indicative of its likelihood to fold into a three-dimensional conformation that is substantially identical to the three-dimensional conformation as in the target protein antigen.

In some embodiments, the method further comprises a step of generating antibodies that bind to the target protein antigen. In some embodiments, the generation of the antibodies comprises (i) immunizing animals with a target protein antigen or a polynucleotide encoding the same from which the fragment antigen candidates are derived; and (ii) identifying antibodies that bind to the target protein antigen.

In some embodiments, the mammalian cell display system comprises HEK293T cells, HeLa cells, or CHO cells.

In some embodiments, the polypeptide fragment is identified based on binding affinity to the antibody in a serum binding assay or a similar assay.

Other features of the invention will become apparent in the course of the following descriptions of exemplary embodiments, which are given for illustration of the invention and are not intended to be limiting thereof.

EXEMPLIFICATION

Example 1: Enhanced Antigenicity of SARS-CoV-2 S Protein Domains with Sbi(III-IV) Fusions This Example describes development of vaccines comprising fragment antigens that focus the immune response on particular regions of an antigen, e.g., conserved and/or functionally critical regions. Immunofocusing in this manner can improve the breadth and efficacy of the vaccine. Among other things, there are two technical challenges for vaccinating with antigens smaller than a protein or a protein subdomain (e.g., a fragment antigen). First, a fragment antigen needs to contain peptides that are efficiently presented on MHC complexes. Second, a fragment antigen must have epitopes folded into the same conformation as in the full protein.

BALB/c mice were administered a 10 μg dose of IM-delivered mRNA encoding: (1) the RBD domain of SARS-CoV-2 S protein (RBD); (2) RBD fused to the transmembrane domain of S protein (RBD-TM); (3) a fusion protein of the RBD domain of SARS-CoV-2 S protein and Sbi(III-IV); or (4) a fusion protein of the RBD domain of SARS-CoV-2 S protein and Sbi(III-IV) and RBD fused to the transmembrane domain of S protein (RBD-TM). A group of unvaccinated mice served as controls. At day 21 post-vaccination, IgG titers were evaluated in the blood using an ELISA. For evaluating the T cell response, spleens from 5 mice were pooled and plated to 4 wells at 500,000 cells/well. Two wells each were stimulated by either N-terminal or C-terminal S protein peptide pools (PepMix SARS-CoV-2 Spike Glycoprotein mix).

The results demonstrated that vaccinating with a minimal antigen fused to a complement C3d-binding region of Sbi protein from *Staphylococcus aureus* (FIG. 1A) enhanced the titers of the resulting antibody response (FIG. 1B). By screening a large set of antigen presentation architectures, this strategy was extended by co-delivery of Sbi(III-IV)-fused antigen with the same antigen fused to a transmembrane domain (FIG. 1B). In addition to eliciting a humoral response, these mRNA-based vaccines also elicited a IFNγ+ IL2+ polyfunctional CD4+ response (FIG. 1C). It was also observed that fusing peptides as short as 25 residues in length to Sbi(III-IV) enabled them to elicit a meaningful antibody response (FIG. 1D). Without wishing to be bound to any particular theory, C3d can directly activate B cells through Complement Receptor 2 (CR2), and allow for induction of immune responses in the absence of CD4+ T cell signaling. Thus, this scaffold can serve as a synthetic immunological synapse, mimicking natural viral infection to drive a strong and appropriate immune response. Accordingly, in some embodiments, the fusion architecture described herein allows small antigens that lack MHC-presented peptides to elicit a meaningful humoral response.

Figures 2A, 2B:
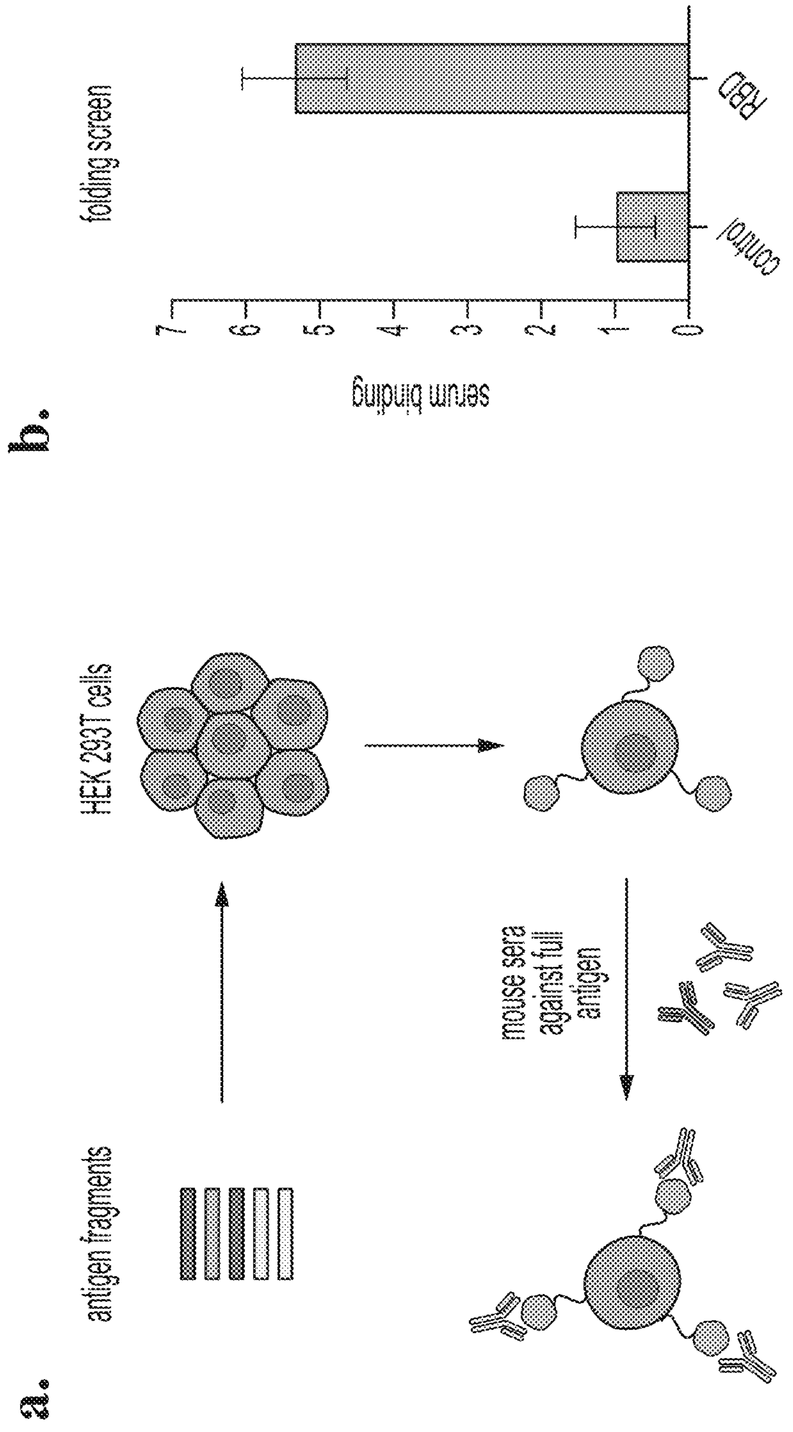
FIGS. 2A-2B depict a high-throughput protein folding screen.

To address the challenge of structure prediction, a high-throughput screen was performed for determining whether a fragment antigen folds into the same three-dimensional conformation as the full protein (FIG. 2A). This screen includes two steps. First, anti-sera against the full protein was generated by vaccinating mice with an mRNA vaccine encoding the full-length protein of interest. The polyclonal antibodies in the sera of the mice were then used as a probe against fragments presented in the context of a mammalian surface display system. As an example, a HEK293T cell expressing a library of antigen fragments can be used in this step. Fragments that bind to antibodies generated by the full protein are likely to share conformational states with the full protein. Correctly folded fragments are identified by an increase in binding to sera antibodies (FIG. 2B). This system allows for the screening of fragments in vitro with two orders of magnitude higher throughput than is practical in vivo.

Example 2: Sbi(III-IV) Fusion to the RBD Domain of SARS-CoV-2 S Protein Increases Virus Neutralization In this Example, virus neutralization activity of serum obtained from mice vaccinated with an mRNA encoding the RBD domain of SARS-CoV-2 S protein, or vaccinated with an mRNA encoding an Sbi(III-IV) fusion to the RBD domain of SARS-CoV-2 S protein was tested.

Figure 3:
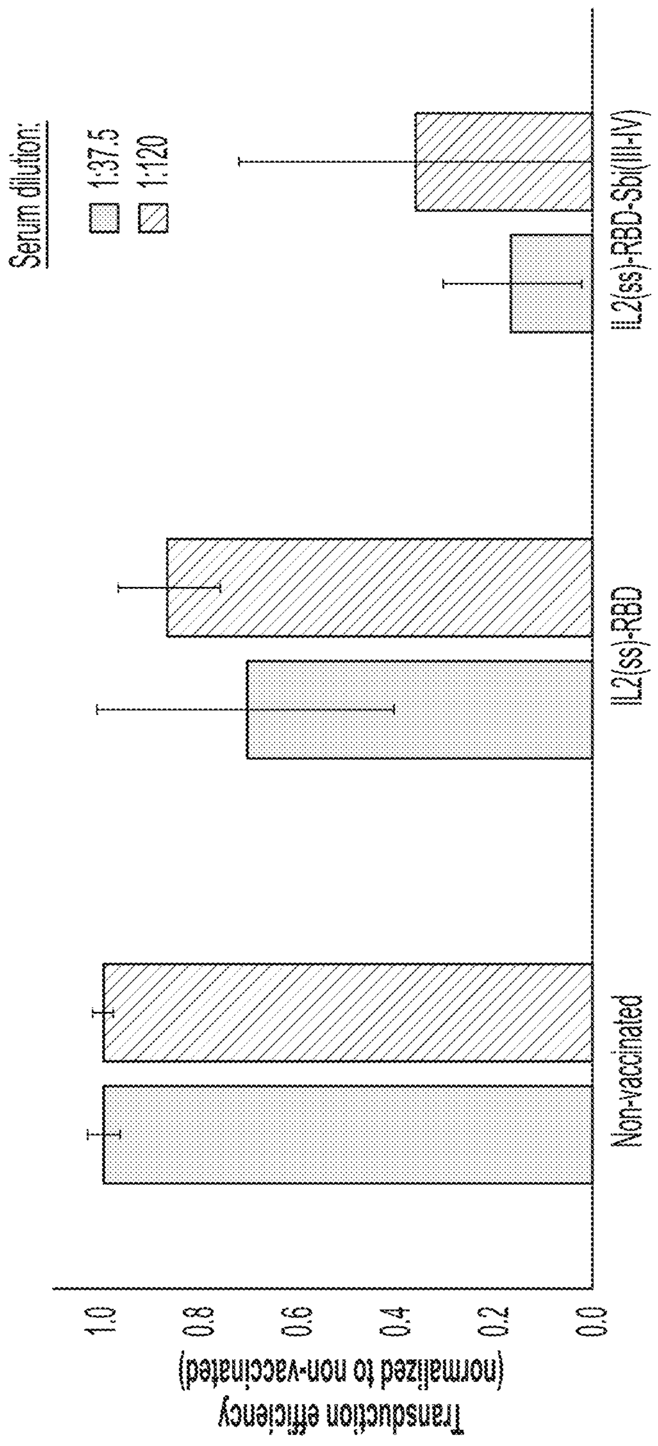
FIG. 3 depicts increased virus neutralization with an Sbi(III-IV) fusion to the RBD domain of SARS-CoV-2 S protein.

For this experiment, BABL/C mice were vaccinated as described in the "animal vaccination" section in Example 6. Specifically, BALB/C mice were injected in the right quadriceps with 50 μL mRNA-LNP formulation (10 μg mRNA dose) of the indicated mRNA constructs. At 10-21 days post-vaccination, serum from vaccinated mice was collected and incubated with target cells in the presence of SARS-CoV-2 virus. Serum from unvaccinated mice was used as a control As shown in FIG. 3, fusing Sbi(III-IV) to the RBD domain of SARS-CoV-2 S protein increases pseudotype virus neutralization compared to the RBD domain of SARS-CoV-2 S protein alone. This effect was observed at both serum dilutions. This data demonstrated that vaccination with mRNA encoding an Sbi(III-IV) fusion to the RBD domain of SARS-CoV-2 S protein results in an antibody response with SARS-CoV-2 virus neutralizing properties.

Example 3: Stimulation of B Cells by an Sbi(III-IV) Fusion to the RBD Domain of SARS-CoV-2 S Protein This Example describes the stimulation of B cells in mice administered a low dose of an mRNA encoding a Sbi(III-IV) fusion to the RBD domain of SARS-CoV-2 S protein.

For this experiment, BABL/C mice were vaccinated as described in the "animal vaccination" section in Example 6. Specifically, mice were vaccinated with a 0.5 ug, 2.5 ug or bug IM-dose of an mRNA comprising a construct having an IL2 secretion peptide and a fusion of the RBD domain of SARS-CoV-2 S protein to Sbi(III-IV), also referred to as IL2(ss)-RBD-Sbi(III-IV). At 10-21 days post-vaccination, blood and spleen were collected from the mice. For titer evaluation, blood from the animals were analyzed with an ELISA assay. For evaluation of T cell responses, an ELISPOT detecting IFNg and/or IL-2 was used.

Figure 4A:
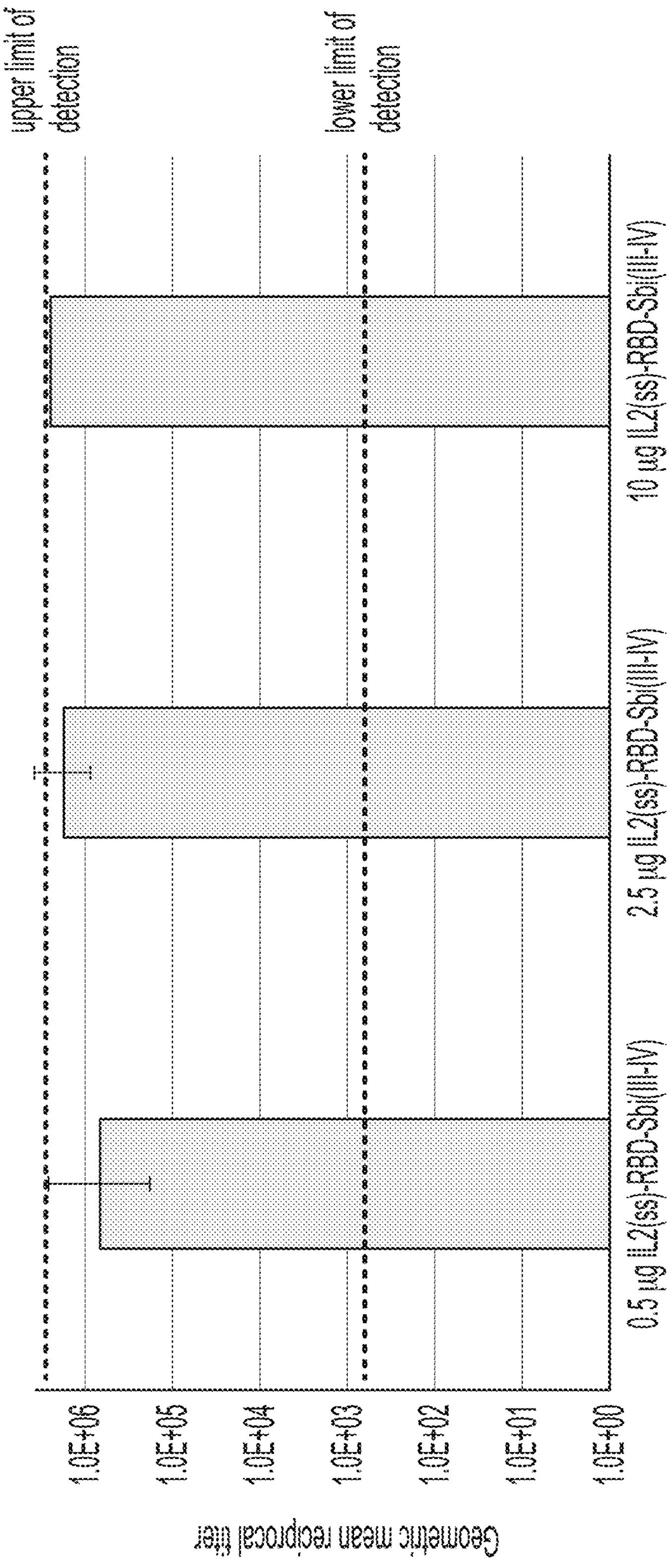
FIGS. 4A-4B depict stimulation of B cells by an Sbi(III-IV) fusion to the RBD domain of SARS-CoV-2 S protein.
Figure 4B:
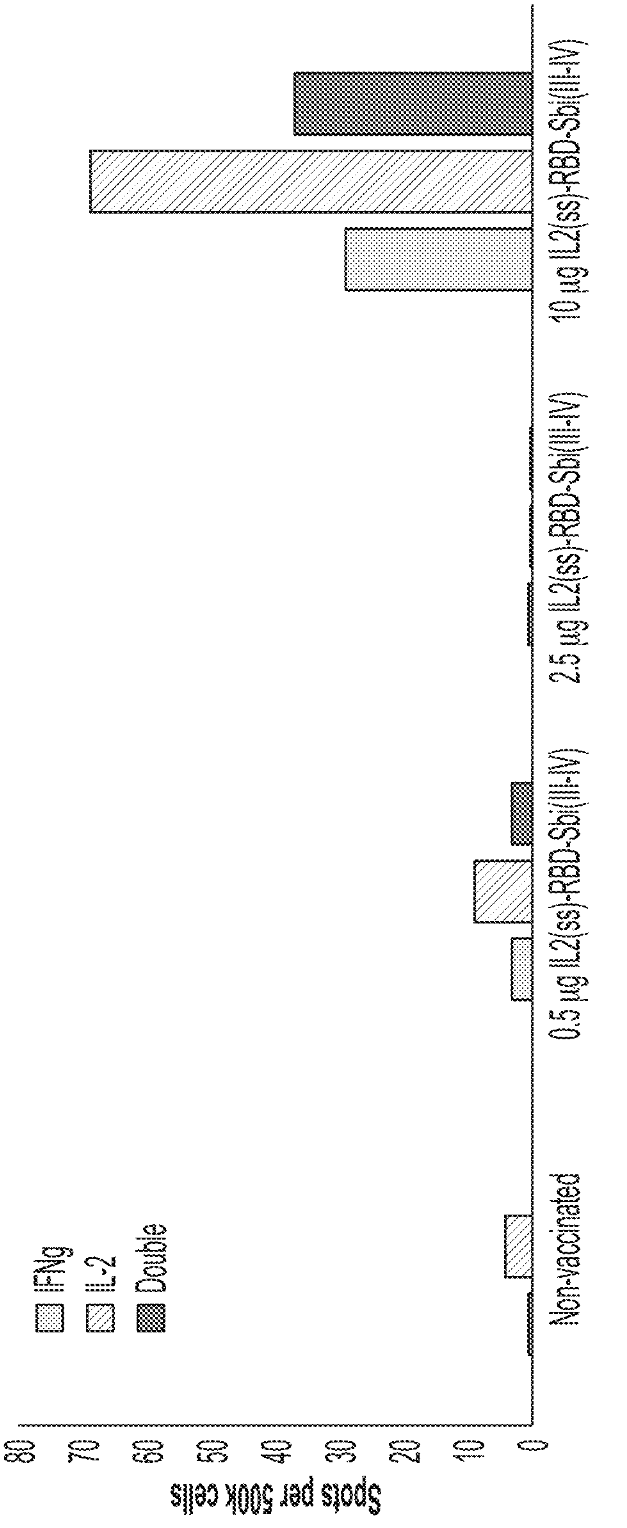

As shown in FIG. 4A, high titers were observed when RBD-Sbi(III-IV) dose was decreased from 10 μg per mouse to 0.5 μg per mouse. Reducing the dose of IL2(ss)-RBD-Sbi(III-IV) below 10 μg reduces the cellular response (FIG. 4B). This data suggested that the antibody response elicited by vaccination with IL2(ss)-RBD-Sbi(III-IV) involves bypassing T cells by directly stimulating B cells.

Example 4: Priming Followed by Boost Increases Antibody Responses Elicited by an Sbi(III-IV) Fusion to the RBD Domain of SARS-CoV-2 S Protein In this Example, the effect of a vaccination regimen comprising a priming dose followed by a booster dose was evaluated.

For this experiment, BABL/C mice were vaccinated as described in the "animal vaccination" section in Example 6. Specifically, mice in 4 groups were injected with a 50 μL mRNA-LNP formulation (10 μg mRNA priming dose) of an mRNA comprising a construct having an IL2 secretion peptide and a fusion of the RBD domain of SARS-CoV-2 S protein to Sbi(III-IV), also referred to as IL2(ss)-RBD-Sbi (III-IV). One group of mice did not receive additional administration of the vaccine (no boost group). The other three groups of mice received a booster dose of 50 μL mRNA-LNP formulation (10 μg mRNA dose) at days 3, 7 and 14 respectively. At 10-21 day post-vaccination, blood and serum was collected from the mice.

Figure 5A:
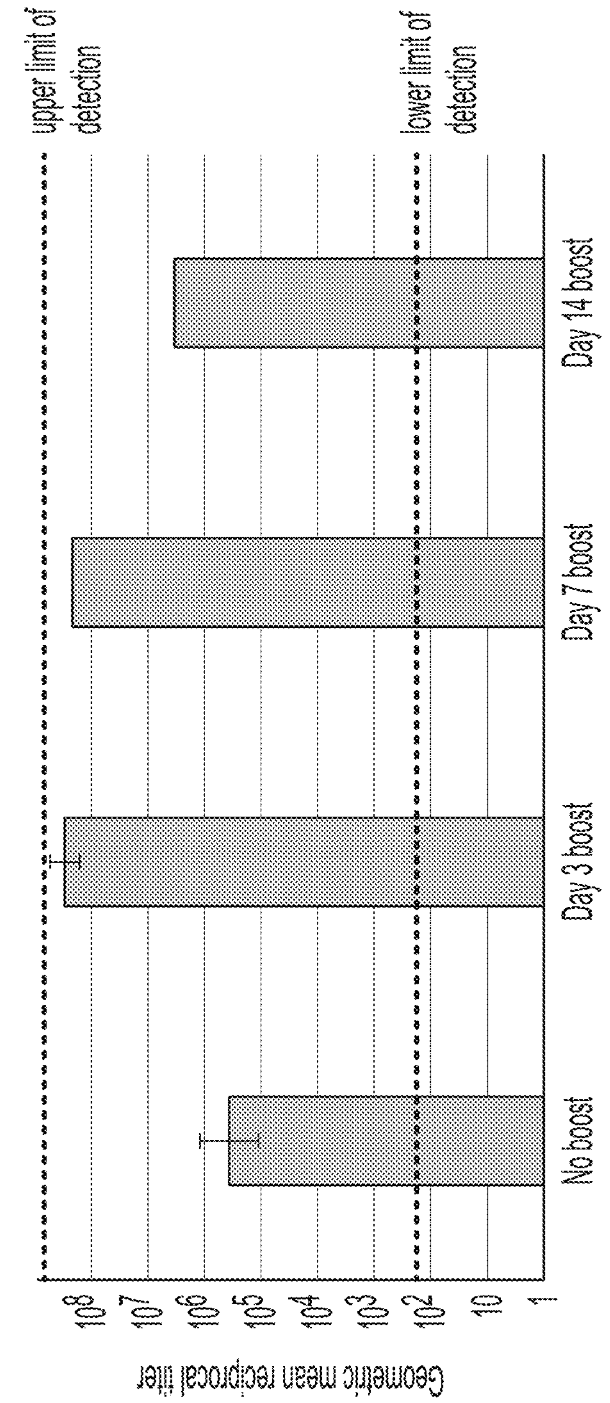
FIGS. 5A-5B depict the results of a vaccination regimen comprising a priming dose and a booster dose.
Figure 5B:
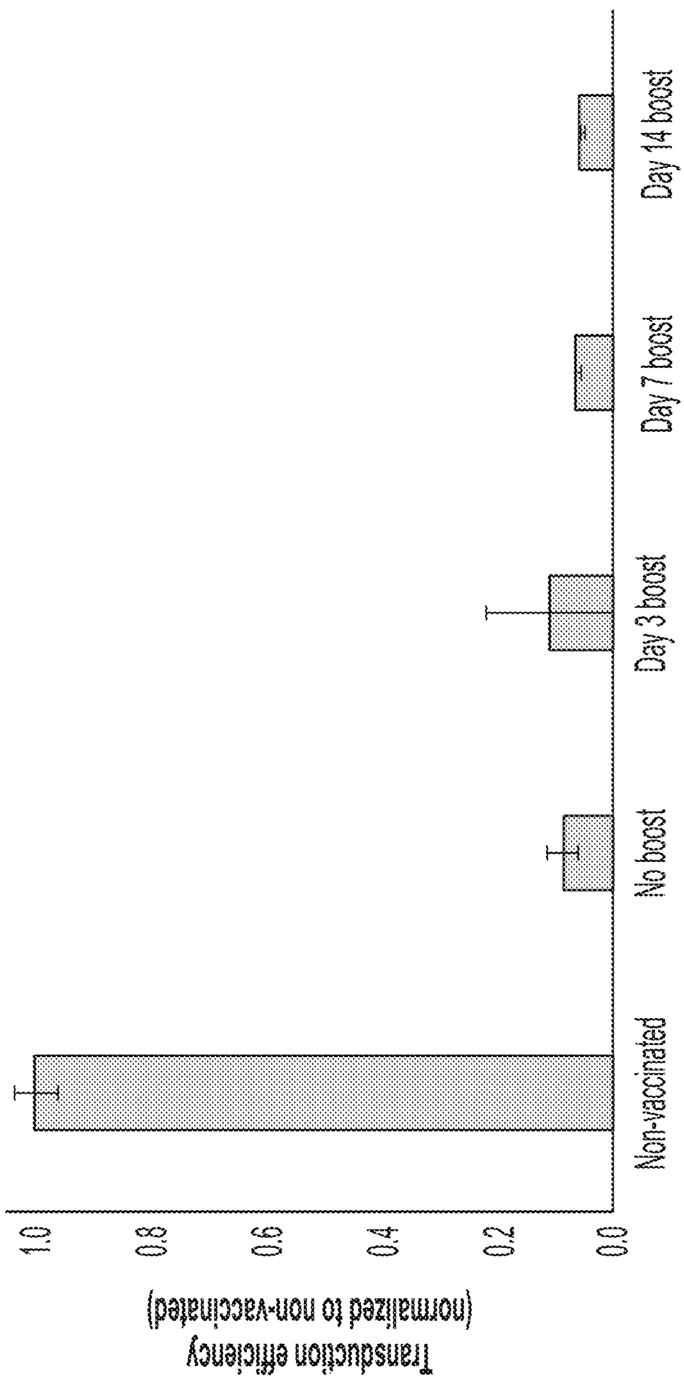

FIG. 5A shows that administration of a booster dose increased the titer generated by IL2(ss)-RBD-Sbi(III-IV) by a factor of ≥776 (when done on day 3 after the prime), by a factor of ≥588.1 (when done on day 7 after the prime), and by a factor of ≥9.2 (when done on day 14 after the prime). FIG. 5B shows that both boosted and prime-only vaccinations were able to block ACE2:RBD interaction in vitro at a 1:20 serum dilution. This data demonstrated that the antibody response elicited by vaccination with IL2(ss)-RBD-Sbi(III-IV) can be enhanced with a vaccination regimen comprising a priming dose and a booster dose.

In the next experiment, the effect of different priming doses was tested. BALB/C mice were injected with a 1 ug or 5 ug priming dose of an mRNA-LNP formulation comprising an mRNA construct having a Spike protein secretion peptide and a fusion of the RBD domain of SARS-CoV-2 S protein to Sbi(III-IV) (S(ss)-RBD-Sbi(III-IV)) or an mRNA comprising a construct having a Spike protein secretion peptide and the RBD domain of SARS-CoV-2 S protein (S(ss)-RBD). The mice received a booster dose on day 4 after priming. At 10-21 day post-vaccination, blood and serum was collected from the mice.

Figure 6A:
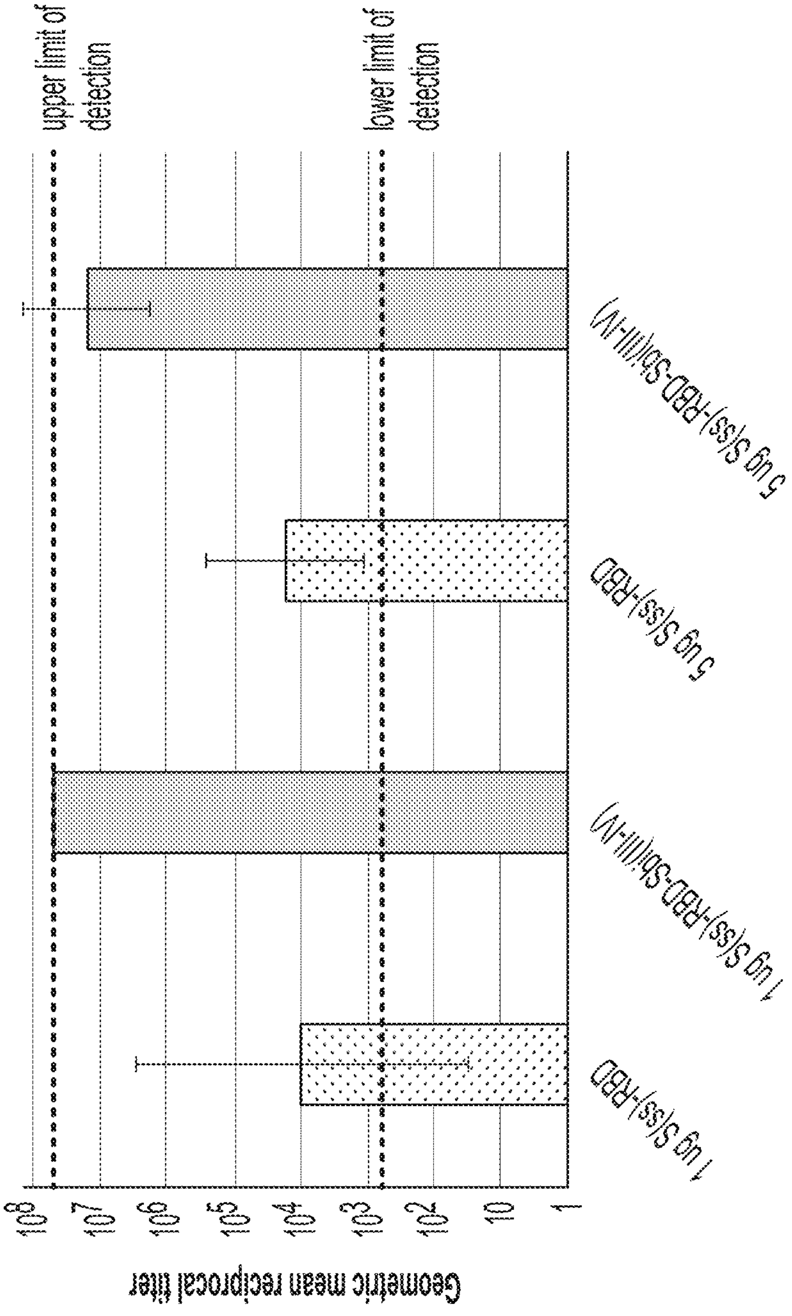
FIG. 6A is a graph showing antibody titer generated with a vaccination regimen comprising a priming dose and a booster dose.

FIG. 6A shows that priming with 1 ug or 5 ug of an mRNA comprising S(ss)-RBD-Sbi(III-IV) resulted in a similar antibody titers. This data demonstrated that a lower priming dose is sufficient to induce an antibody response.

Example 5: Development of a Broad Influenza A Subtype H1N1 Vaccine that is Resistant to HA Antigen Drift This Example describes utilizing methods provided in this disclosure to develop a broad viral (e.g., influenza A subtype H1N1 vaccine) that is resistant to HA antigen drift. This strategy is expected to be broadly applicable. This approach can be extended by building a drift- and shift-resistant vaccine containing precisely designed antigens for all eighteen influenza HA subtypes.

Figure 7A:
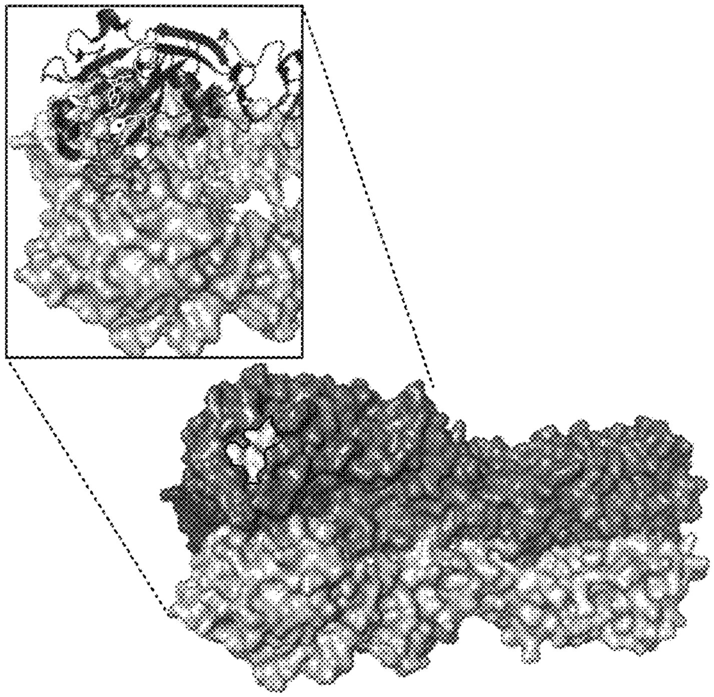

The high throughput folding screen described in Example 2 is used to identify a minimal antigen within the ribosome binding site (RBS) of the hemagglutinin HA1 head domain (FIG. 7A). The RBS is essential for receptor binding and is broadly conserved across influenza A H1N1 viruses (FIG. 7B), yet surrounding variable residues often limit the breadth of RBS-directed antibodies (Raymond et al. (2018) PNAS 115(1):168-173). The screen is used to identify a minimal foldable RBS which can focus the immune response on the conserved residues.

Example 6: Materials and Methods Used in Examples Disclosed Herein gBlock amplification: Each gBlock template was amplified with T7-AGG_fwd (gaattTAATACGACTCACTATAAGGcttgttctttttgcagaagc)(SEQ ID NO: 62) and 120 pA_rev (TTTTTTTTTTTTTTTTTTTTTTTTTTTTTT TT TT TTTTTTTTTTTTTTTTTTTTTTTTTTTT TTTTTT TT TTTTTTTTTTTTTTTTTTTTTTTTTTTTTTTTTTTTTT TTTTTTTTTTTagaatgtga agaaactttctttttattag) (SEQ ID NO: 55) using Herculase II polymerase (Agilent) with an annealing temperature of 50° C.

mRNA synthesis: The PCR products were cleaned up using a 0.8× ratio of SPRISelect beads to PCR reaction volume. 19.9 μL transcription mixes consisting of 1× HiScribe T7 High Yield buffer (NEB), 7.5 mM of each NTP, 7.5 mM CleanCap AG (TriLink Biotech), 2M betaine (ThermoSci), 20 mM MgCl2, and 0.1 μL/μL HiScribe T7 Polymerase Mix were added to 2.1 uL DNA solution consisting of 200 ng T7 template in nuclease free H2O. Transcription was carried out for 1 hr at 50° C. The transcribed RNAs were purified using the 500 μg capacity Monarch RNA Cleanup Kit, treated with DNAse I, and purified again using 500 μg-capacity Monarch columns. mRNAs were then treated with Alkaline Phosphatase (Millipore) for 10 min at 37° C. and purified using 500 μg Monarch columns. Concentrations were determined using a NanoDrop spectrophotometer.

LNP formulation: Formulations of mRNA in lipid nanoparticles (mRNA-LNPs) were prepared using the NanoAssemlr Ignite microfluidic mixer (Precision Nanosystems). GenVoy-ILM lipid mixture (Precision Nanosystems) was diluted to 12.5 mM in anhydrous ethanol and combined with an aqueous solution of mRNA (0.14 mg/mL) in PNI buffer (Precision Nanosystems), using the manufacturer-recommended formulation parameters. Formulations were immediately diluted 30:1 in phosphate-buffered saline (pH 7.4) and concentrated using Amicon centrifugation filters (MilliporeSigma UFC901008). Formulations were stored at 4° C. and used for in vivo studies within 14 days.

Animal vaccination: All animal experiments were carried out in accordance with the guidelines set forth by Charles River Accelerator Development Lab (CRADL) and were approved by the CRADL Institutional Animal Care and Use committee. Female BALB/C mice (7-9 weeks old) were purchased from Charles River Laboratories and housed at CRADL. Mice were acclimated for at least 3 days before the initiation of a study. On Day 1, mice were injected in the right quadriceps with 50 μL mRNA-LNP formulation (10 μg mRNA dose was used unless stated otherwise.) For experiments involving two vaccinations, mice were additionally injected in the left quadriceps with 50 μL mRNA-LNP formulation for booster immunizations. Mice were euthanized at day 10-21 (as indicated), at which time blood was collected via intracardiac stick and spleens were dissected and collected for processing. Serum was separated from blood in MiniCollect serum separator tubes (Greiner Bio-One 450472) by centrifugation at 4° C., 1200×g, for 10 minutes. Fresh serum was stored at 4° C. and used to evaluate immunogenicity by ELISA and neutralization assay, the remainder was aliquoted and frozen at −80° C.

Spike titer ELISA assay: The ELISA protocol was adapted from one previously established by Amanat, et al. (Nat Med 26: 1033-1036, 2020). Briefly, 96-well Immulon 4 HBX plates (Thermo Fisher Scientific) were coated with 50 μl per well of a 2 μg/ml solution of SARS-CoV-2 (2019-nCoV) Spike S1+S2 ECD-His recombinant protein (Sino Biological #40589-V08B1) in PBS at 4° C. overnight. Plates were washed three times with 300 μl of 0.1% Tween 20 in PBS (PBS-T), then were blocked for 1 h with 100 μl per well of 3% non-fat milk in PBS-T. Serial dilutions of serum and antibody controls were prepared in 1% non-fat milk in PBS-T, and 100 μl of each was added to the plates for 2 h at room temperature. The wells then were washed thrice in PBS-T as before. Wells were then incubated in 100 μl of a 1:3,000 dilution of goat anti-mouse IgG horseradish peroxidase-conjugated secondary antibody (Sigma) in 1% milk PBS-T room temperature for 1 hour. Plates were again washed thrice in PBS-T. 100 μl SIGMAFAST OPD (Sigma-Aldrich) solution was added to each well for 10 min at room temperature for 10 min. Reactions were stopped by addition of 50 μl per well of 3 M hydrochloric acid. Optical density was measured at 490 nm using a GloMax Discover (Promega) plate reader. End-point titers were determined by taking the last dilution before the signal dropped below 1 standard deviation above the average of the signal from the untreated control serum at the same dilution. The last dilution was taken as the titer if the signal never dropped below this threshold. If no signal above the threshold was detected, the value in the dilution series before the least-dilute sample tested was used. A chimeric monoclonal antibody reactive to the RBD of both SARS-CoV-1 and SARS-CoV-2, and a SARS-CoV-1 reactive mouse monoclonal antibody were used as positive and negative controls, respectively.

Pseudotype neutralization assay: Human ACE2-overexpressing HEK cells (Integral Molecular) used for viral transduction experiments were maintained in high glucose GlutaMAX-containing DMEM (ThermoFisher Scientific 10564) supplemented with 1 μg/mL puromycin, 10% heat-inactivated fetal bovine serum and 100 U/mL penicillin/streptomycin. 4 μl (for 1:37.5 dilution) or 1 μl (for 1:500 dilution) of each serum was mixed with 35 μl spike-pseudotyped GFP-encoding reporter viral particles built using a second-generation lentiviral system (Integral Molecular, lot CG-113A) in puromycin-free culture media to a total volume of 100 μl. Virus and serum were incubated in a 96-wel cell culture plate at 37° C. for 1.5 h. 20,000 freshly harvested HEK cells were then added in 50 μL puromycin-free culture media, and transduction was allowed to proceed for 3 days. The Cytation 5 Cell Imaging Multi-Mode Reader and Gen5 software (BioTek) were used to quantify the number of GFP-positive cells. Images were taken of each well using a 4× PL ACH objective in the GFP (469, 525) channel with the LED set to 10.0, an integration time of 100 msec, and gain set to 11.0. Images were taken at a fixed focal height 345 μm below the plate. 6 images were taken per well with automatic overlap to allow the software to stitch them together. Image preprocessing was applied using a dark background and background flattening with a rolling ball diameter of 60 μm. For cellular analysis a primary mask was applied to the processed images with a dark background and a GFP threshold of 2000. Minimum and maximum object sizes were set to 10 μm and 1000 μm, respectively. Split touching objects, fill holes in mask, include edge objects, and analyze entire image were set to ON. Using these parameters, the software calculated a cell count to give the number of GFP-positive cells per well.

ACE2:RBD inhibition assay: The ability of vaccinated sera to inhibit ACE2:RBD binding was measured essentially as described in Nie, et al. (Nat Biotech 15: 3699-3715, 2020), using the SARS-CoV-2 Surrogate Virus Neutralization Test kit (GenScript).

Equivalents

Those skilled in the art will recognize, or be able to ascertain using no more than routine experimentation, many equivalents to the specific embodiments of the invention described herein. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Further, it should also be understood that any embodiment or aspect of the invention can be explicitly excluded from the claims, regardless of whether the specific exclusion is recited in the specification. The scope of the present invention is not intended to be limited to the above Description, but rather is as set forth in the claims that follow.

EXEMPLARY EMBODIMENTS

Embodiment 1. A fusion polypeptide comprising:

(i) a fragment antigen that comprises an epitope of a target protein antigen; and (ii) a complement C3d-binding polypeptide from an immunoglobulin-binding protein (Sbi) of *Staphylococcus aureus*.

Embodiment 2. The fusion polypeptide of embodiment 1, wherein the complement C3d-binding polypeptide is or comprises one or both of domain III and domain IV of the Sbi of *Staphylococcus aureus*, or a functional fragment or a variant thereof.

Embodiment 3. The fusion polypeptide of embodiment 1 or 2, wherein the fragment antigen has an amino acid sequence length of at least 5%, 10%, 20%, 30%, 40%, 50%, 60%, 70%, 80%, 90% or 95% compared to the amino acid sequence length of the target protein antigen.

Embodiment 4. The fusion polypeptide of embodiment 1 or 2, wherein the fragment antigen has an amino acid sequence length of no more than 50% of the amino acid sequence length of the target protein antigen.

Embodiment 5. The fusion polypeptide of embodiment 4, wherein the fragment antigen has an amino acid sequence length of no more than 40%, 30%, 20%, 10% or 5% of the amino acid sequence length of the target protein antigen.

Embodiment 6. The fusion polypeptide of any one of embodiments 1-5, wherein the fragment antigen has about 10-300 amino acid residues in length.

Embodiment 7. The fusion polypeptide of embodiment 6, wherein the fragment antigen has at least 10 amino acid residues in length.

Embodiment 8. The fusion polypeptide of embodiment 6, wherein the fragment antigen has less than about 300 amino acid residues in length.

Embodiment 9. The fusion polypeptide of any one of embodiments 1-5, wherein the fragment antigen has about 10-300, 10-250, 10-200, 10-150, 10-100, 10-90, 10-80, 10-70, 10-60, 10-50, 10-40, 10-30, 10-20, 20-300, 30-300, 40-300, 50-300, 60-300, 70-300, 80-300, 90-100, 100-300, 150-300, 200-300, 250-300, 20-250, 30-200, 40-150, 50-100, 60-90, or 70-80 amino acids residues in length.

Embodiment 10. The fusion polypeptide of any one of embodiments 1-5, wherein the fragment antigen has about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 amino acids residues in length.

Embodiment 11. A fusion polypeptide comprising:

(i) an antigen variant or a fragment antigen variant that comprises an epitope of a target protein antigen; and (ii) a complement C3d-binding polypeptide from an immunoglobulin-binding protein (Sbi) of *Staphylococcus aureus*.

Embodiment 12. The fusion polypeptide of embodiment 11, wherein the complement C3d-binding polypeptide is or comprises one or both of domain III and domain IV of the Sbi of *Staphylococcus aureus*, or a functional fragment or a variant thereof.

Embodiment 13. The fusion polypeptide of embodiment 11 or 12, wherein the antigen variant or fragment antigen variant amino acid sequence length is identical to the amino acid sequence length of the target protein antigen.

Embodiment 14. The fusion polypeptide of any one of embodiments 11-13, wherein the antigen variant or fragment antigen variant comprises at least one modified amino acid compared to the target protein antigen.

Embodiment 15. The fusion polypeptide of embodiment 14, wherein the modified amino acid comprises N-linked glycosylation.

Embodiment 16. The fusion polypeptide of any one of embodiments 11-15, wherein the antigen variant or fragment antigen variant comprises at least one amino acid mutation compared to the target protein antigen.

Embodiment 17. The fusion polypeptide of embodiment 16, wherein the antigen variant or fragment antigen variant comprises 2, 3, 4, 5, 6, 7, 8, 9, 10, 15, 20, 30, 40 or 50 amino acid mutations compared to the target protein antigen.

Embodiment 18. The fusion polypeptide of embodiment 16 or 17, wherein the mutation introduces a Serine, a Threonine, an Alanine, or an amino acid at a particular position which is different from the amino acid present at that position in the target protein antigen.

Embodiment 19. The fusion polypeptide of any one of embodiments 16-18, wherein the mutation prevents formation of a disulfide bond.

Embodiment 20. The fusion polypeptide of any one of the preceding embodiments, wherein the fragment antigen is characterized in that when expressed in vivo, it binds to a Major Histocompatibility Complex (MHC) molecule.

Embodiment 21. The fusion polypeptide of any one of embodiments 1-19, wherein the fragment antigen is characterized in that when expressed in vivo, it does not bind to a MHC molecule.

Embodiment 22. The fusion polypeptide of embodiment 20 or 21, wherein the MHC molecule is or comprises a MHC I molecule or a MHC II molecule.

Embodiment 23. The fusion polypeptide of any one of the preceding embodiments, wherein the fragment antigen is characterized in that when expressed in vivo, it folds into a three-dimensional conformation that is substantially identical to the three-dimensional conformation of the fragment antigen as it is in its native position in the target protein antigen.

Embodiment 24. The fusion polypeptide of any one of the preceding embodiments, wherein the fragment antigen, antigen variant or fragment antigen variant further comprises an amino acid sequence from a second target protein antigen.

Embodiment 25. The fusion polypeptide of any one of the preceding embodiments, wherein the target protein antigen is or comprises an infectious disease antigen.

Embodiment 26. The fusion polypeptide of embodiment 25, wherein the infectious disease antigen is or comprises a viral antigen, a bacterial antigen, a fungal antigen, or combinations thereof.

Embodiment 27. The fusion polypeptide of embodiment 26, wherein the target protein antigen is or comprises a cancer antigen.

Embodiment 28. The fusion polypeptide of embodiment 27, wherein the antigen is or comprises a viral antigen.

Embodiment 29. The fusion polypeptide of embodiment 26, wherein the viral antigen is or comprises an influenza antigen.

Embodiment 30. The fusion polypeptide of embodiment 29, wherein the viral antigen is or comprises a coronavirus polypeptide.

Embodiment 31. The fusion polypeptide of embodiment 30, wherein the coronavirus polypeptide is or comprises a SARS-CoV-2 protein.

Embodiment 32. The fusion polypeptide of embodiment 31, wherein the SARS-CoV-2 protein is or comprises a Spike protein (SARS-CoV-2 S) or fragment thereof; an Envelope protein (SARS-CoV-2 E) or fragment thereof; a Membrane protein (SARS-CoV-2 M) or fragment thereof; a nucleocapsid protein (SARS-CoV-2 N) or fragment thereof; an accessory factor polypeptide or fragment thereof; or any combination thereof.

Embodiment 33. The fusion polypeptide of embodiment 31 or 32, wherein the SARS-CoV-2 protein comprises a Spike protein or a fragment thereof (e.g., RBD).

Embodiment 34. The fusion polypeptide of any one of embodiments 1-33, wherein the fragment antigen, antigen variant or fragment antigen variant has an amino acid sequence at least 80%, 85%, 90%, 91%, 92%, 93%, 94%, 95%, 96%, 97%, 98%, 99% or 100% identity to the amino acid sequence of SEQ ID NO: 3.

Embodiment 35. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 4.

Embodiment 36. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 5.

Embodiment 37. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 6.

Embodiment 38. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 7.

Embodiment 39. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 20.

Embodiment 40. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 21.

Embodiment 41. The fusion polypeptide of any one of embodiments 1-3, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 22.

Embodiment 42. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 23.

Embodiment 43. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 24.

Embodiment 44. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 25.

Embodiment 45. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO:26.

Embodiment 46. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 27.

Embodiment 47. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 28.

Embodiment 48. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 29.

Embodiment 49. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 30.

Embodiment 50. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 31.

Embodiment 51. The fusion polypeptide of any one of embodiments 1-33, wherein the fragment antigen, antigen variant or fragment antigen variant has at least 80%, 85%, 90%, or 100% identity to the amino acid sequence of SEQ ID NO: 8.

Embodiment 52. The fusion polypeptide of any one of the preceding embodiments, wherein the complement C3d-binding polypeptide comprises an Sbi domain III having at least 80%, 85%, 90%, 91%, 92%, 93%, 94%, 95%, 96%, 97%, or 100% identity to the amino acid sequence of SEQ ID NO: 9.

Embodiment 53. The fusion polypeptide of any one of the preceding embodiments, wherein the complement C3d-binding polypeptide comprises an Sbi domain IV having at least 80%, 85%, 90%, 91%, 92%, 93%, 94%, 95%, 96%, 97%, or 100% identity to the amino acid sequence of SEQ ID NO: 10.

Embodiment 54. The fusion polypeptide of any one of the preceding embodiments, wherein the Sbi domain III and the Sbi domain IV are contiguous.

Embodiment 55. The fusion polypeptide of any one of embodiments 2-54, wherein the Sbi domain III and the Sbi domain IV are separated by a linker.

Embodiment 56. The fusion polypeptide of any one of the preceding embodiments, wherein (a) and (b) are encoded by a nucleotide sequence and are disposed in the same nucleotide sequence or in different nucleotide sequences.

Embodiment 57. The fusion polypeptide of any one of the preceding embodiments, wherein (a) is disposed N-terminus of (b).

Embodiment 58. The fusion polypeptide of any one of embodiments 1-56, wherein (a) is disposed C-terminus of (b).

Embodiment 59. The fusion polypeptide of any one of the preceding embodiments, wherein (a) and (b) are contiguous or separated by a linker.

Embodiment 60. The fusion polypeptide of embodiment 59, wherein the linker is a peptidyl linker.

Embodiment 61. The fusion polypeptide of embodiment 60, wherein the peptidyl linker comprises at least 60% glycine and/or serine.

Embodiment 62. The fusion polypeptide of embodiment 60, wherein the linker is chosen from a Gly-Gly-Gly-Gly-Ser (Gly4-Ser) linker, or a Histidine linker.

Embodiment 63. The fusion polypeptide of embodiment 62, wherein the linker is a Gly4-Ser linker.

Embodiment 64. The fusion polypeptide of embodiment 63, wherein the linker comprises 1, 2, 3, 4, 5, 6, 7, 8, 9, or 10 repeats of the Gly4-Ser linker.

Embodiment 65. The fusion polypeptide of embodiment 64, wherein the linker comprises 3 repeats of the Gly4-Ser linker.

Embodiment 66. The fusion polypeptide of any one of embodiments 62-65, wherein the linker comprises the sequence of SEQ ID NO: 11.

Embodiment 67. The fusion polypeptide of any one of embodiments 1-66, wherein the polypeptide further comprises a secretion peptide.

Embodiment 68. The fusion polypeptide of embodiment 67, wherein the secretion peptide is about 10-30 amino acids in length.

Embodiment 69. The fusion polypeptide of embodiment 67 or 68, wherein the secretion peptide is about 10, 11, 12, 13, 14, 15, 16, 17, 18, 19, 20, 21, 22, 23, 24, 25, 26, 27, 28, 29 or 30 amino acids in length.

Embodiment 70. The fusion polypeptide of any one of embodiments 67-69, wherein the secretion peptide comprises an amino acid having at least 80%, 85%, 90%, or 100% identity to the amino acid sequence of SEQ ID NO: 1.

Embodiment 71. The fusion polypeptide of any one of embodiments 67-69, wherein the secretion peptide comprises an amino acid having at least 80%, 85%, 90%, or 100% identity to the amino acid sequence of SEQ ID NO: 2.

Embodiment 72. The fusion polypeptide of any one of the preceding embodiments, wherein the polypeptide has at least 80%, 85%, 90%, 91%, 92%, 93%, 94%, 95%, 96%, 97%, 98%, 99% or 100% identity to the amino acid sequence of SEQ ID NO: 12.

Embodiment 73. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 13.

Embodiment 74. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 14.

Embodiment 75. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 15.

Embodiment 76. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 16.

Embodiment 77. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 17.

Embodiment 78. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 18.

Embodiment 79. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 19.

Embodiment 80. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 32.

Embodiment 81. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 33.

Embodiment 82. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 34.

Embodiment 83. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:35.

Embodiment 84. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:36.

Embodiment 85. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:37.

Embodiment 86. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:38.

Embodiment 87. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:39.

Embodiment 88. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:40.

Embodiment 89. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:41.

Embodiment 90. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:42.

Embodiment 91. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 43.

Embodiment 92. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 44.

Embodiment 93. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:45.

Embodiment 94. The fusion polypeptide of any one of the preceding embodiments, wherein the polypeptide is encoded by a polynucleotide which is or comprises RNA.

Embodiment 95. The fusion polypeptide of embodiment 94, wherein the polynucleotide is or comprises messenger RNA.

Embodiment 96. The fusion polypeptide of any one of the preceding embodiments, wherein the polypeptide is encoded by a polynucleotide which is or comprises DNA.

Embodiment 97. A fusion polynucleotide encoding the fusion polypeptide of any one of embodiments 1-96.

Embodiment 98. A fusion polynucleotide comprising a nucleotide sequence encoding:

(i) a fragment antigen that comprises an epitope of a target protein antigen; and (ii) a complement C3d-binding polypeptide from an immunoglobulin-binding protein (Sbi) of *Staphylococcus aureus*.

Embodiment 99. A fusion polynucleotide comprising a nucleotide sequence encoding:

(i) an antigen variant or a fragment antigen variant that comprises an epitope of a target protein antigen; and (ii) a complement C3d-binding polypeptide from an immunoglobulin-binding protein (Sbi) of *Staphylococcus aureus*.

Embodiment 100. The fusion polynucleotide of embodiment 98 or 99, wherein the polynucleotide is or comprises RNA.

Embodiment 101. The fusion polynucleotide of embodiment 100, wherein the polynucleotide is or comprises messenger RNA.

Embodiment 102. The fusion polynucleotide of any one of embodiments 98-101, wherein the polynucleotide is or comprises DNA.

Embodiment 103. The fusion polynucleotide of embodiment 98, wherein the complement C3d-binding polypeptide is or comprises one or both of domain III and domain IV of the Sbi of *Staphylococcus aureus*, or a functional fragment or a variant thereof.

Embodiment 104. The fusion polynucleotide of embodiment 98 or 99, wherein the polynucleotide encodes a fragment antigen that has an amino acid sequence length of at least 5%, 10%, 20%, 30%, 40%, 50%, 60%, 70%, 80%, 90% or 95% compared to the amino acid sequence length of the target protein antigen.

Embodiment 105. The fusion polynucleotide of embodiment 98 or 99, wherein the polynucleotide encodes a fragment antigen that has an amino acid sequence length of no more than 50% of the amino acid sequence length of the target protein antigen.

Embodiment 106. The fusion polynucleotide of embodiment 105, wherein the polynucleotide encodes a fragment antigen has an amino acid sequence length of no more than 40%, 30%, 20%, 10% or 5% of the amino acid sequence length of the target protein antigen.

Embodiment 107. The fusion polynucleotide of embodiment 99, wherein the polynucleotide encodes an antigen variant or fragment antigen variant having an amino acid sequence length that is identical to the amino acid sequence length of the target protein antigen.

Embodiment 108. The fusion polynucleotide of embodiment 99 or 107, wherein the polynucleotide encodes an antigen variant or fragment antigen variant which comprises at least one modified amino acid compared to the target protein antigen.

Embodiment 109. The fusion polynucleotide of any one of embodiments 98-108, wherein the polynucleotide encodes a fragment antigen which is characterized in that when expressed in vivo, it binds to a Major Histocompatibility Complex (MHC) molecule.

Embodiment 110. The fusion polynucleotide of any one of embodiments 98-109, wherein the polynucleotide encodes a fragment antigen which is characterized in that when expressed in vivo, it does not bind to a MHC molecule.

Embodiment 111. The fusion polynucleotide of embodiment 109 or 110, wherein the MHC molecule is or comprises a MHC I molecule or a MHC II molecule.

Embodiment 112. The fusion polynucleotide of any one of embodiments 98-111, wherein the polynucleotide encodes a fragment antigen which is characterized in that when expressed in vivo, it folds into a three-dimensional conformation that is substantially identical to the three-dimensional conformation of the fragment antigen as it is in its native position in the target protein antigen.

Embodiment 113. The fusion polynucleotide of any one of embodiments 98-112, wherein the polynucleotide encodes a fragment antigen, antigen variant or fragment antigen variant which further comprises an amino acid sequence from a second target protein antigen.

Embodiment 114. The fusion polynucleotide of any one of the preceding embodiments, wherein the target protein antigen is or comprises an infectious disease antigen.

Embodiment 115. The fusion polynucleotide of embodiment 114, wherein the infectious disease antigen is or comprises a viral antigen, a bacterial antigen, a fungal antigen, or combinations thereof.

Embodiment 116. The fusion polynucleotide of embodiment of any one of embodiments 98-113, wherein the target protein antigen is or comprises a cancer antigen.

Embodiment 117. The fusion polynucleotide of embodiment 114, wherein the antigen is or comprises a viral antigen.

Embodiment 118. The fusion polynucleotide of embodiment 114, wherein the viral antigen is or comprises an influenza antigen.

Embodiment 119. The fusion polynucleotide of embodiment 114, wherein the viral antigen is or comprises a coronavirus polypeptide.

Embodiment 120. The fusion polynucleotide of embodiment 119, wherein the coronavirus polypeptide is or comprises a SARS-CoV-2 protein.

Embodiment 121. The fusion polynucleotide of embodiment 120, wherein the SARS-CoV-2 protein is or comprises a Spike protein (SARS-CoV-2 S) or fragment thereof; an Envelope protein (SARS-CoV-2 E) or fragment thereof; a Membrane protein (SARS-CoV-2 M) or fragment thereof; a nucleocapsid protein (SARS-CoV-2 N) or fragment thereof; an accessory factor polypeptide or fragment thereof; or any combination thereof.

Embodiment 122. The fusion polynucleotide of embodiment 120 or 121, wherein the SARS-CoV-2 protein comprises a Spike protein or a fragment thereof (e.g., RBD).

Embodiment 123. The fusion polynucleotide of any one of embodiments 98-122, wherein (a) is disposed C-terminus of (b).

Embodiment 124. The fusion polynucleotide of any one of embodiments 98-123, wherein (a) and (b) are contiguous or separated by a nucleotide sequence encoding a linker.

Embodiment 125. The fusion polynucleotide of embodiment 124, wherein the linker is a peptidyl linker.

Embodiment 126. The fusion polynucleotide of embodiment 125, wherein the peptidyl linker comprises at least 60% glycine and/or serine.

Embodiment 127. The fusion polynucleotide of embodiment 126, wherein the linker is chosen from a Gly-Gly-Gly-Gly-Ser (Gly4-Ser) linker, or a Histidine linker.

Embodiment 128. The fusion polynucleotide of any one of embodiments 98-127, wherein the polynucleotide further comprises a nucleotide sequence encoding a secretion peptide.

Embodiment 129. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 46.

Embodiment 130. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 47.

Embodiment 131. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 48.

Embodiment 132. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 49.

Embodiment 133. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 50.

Embodiment 134. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 51.

Embodiment 135. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 52.

Embodiment 136. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 53.

Embodiment 137. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 54.

Embodiment 138. An expression vector comprising the fusion polynucleotide of any one of embodiments 97-137.

Embodiment 139. The expression vector of embodiment 138, wherein the expression vector comprises a viral vector.

Embodiment 140. The expression vector of embodiment 138 or 139, wherein the viral vector comprises a retrovirus vector, an adenovirus vector, an adeno-associated virus vector or a lentivirus vector or an RNA vector.

Embodiment 141. A composition for delivering the fusion polypeptide of any one of embodiments 1-96.

Embodiment 142. A composition for delivering the fusion polynucleotide of any one of embodiments 97-137.

Embodiment 143. A pharmaceutical composition that delivers the fusion polypeptide of any one of embodiments 1-96, the fusion polynucleotide of any one of embodiments 97-137, or the expression vector of any one of embodiments 138-140.

Embodiment 144. The pharmaceutical composition of embodiment 143, further comprising a pharmaceutically acceptable excipient, a diluent, or a combination thereof.

Embodiment 145. A method of making comprising:

recombinantly joining a first nucleotide sequence that encodes a fragment antigen comprising an epitope of a target protein antigen, and a second nucleotide sequence that encodes a complement C3d-binding polypeptide from a immunoglobulin-binding protein (Sbi) of *Staphylococcus aureus* to form a polynucleotide comprising the first nucleotide sequence and the second nucleotide sequence.

Embodiment 146. The method of embodiment 145, further comprising expressing the polynucleotide in a cell to produce a fusion polypeptide encoded by the polynucleotide.

Embodiment 147. A cell comprising the fusion polypeptide of any one of embodiments 1-96, the fusion polynucleotide of any one of embodiments 97-137, or the expression vector of any one of embodiments 138-140.

Embodiment 148. The cell of embodiment 147, wherein the cell is contacted with the fusion polynucleotide, fusion polypeptide or expression vector.

Embodiment 149. The cell of embodiment 147 or 148, wherein the contacting occurs in vivo, in vitro or ex vivo.

Embodiment 150. A kit comprising the fusion polypeptide of any one of embodiments 1-96, the fusion polynucleotide of any one of embodiments 97-137, the expression vector of any one of embodiments 138-140, or the pharmaceutical composition of embodiment 143 or 144, and instructions for use.

Embodiment 151. The kit of embodiment 150, further comprising: a polynucleotide comprising a nucleotide sequence that encodes a target protein antigen; or a target protein antigen encoded by the polynucleotide.

Embodiment 152. A method comprising administering to a subject in need thereof at least one dose of the pharmaceutical composition of embodiment 143 or 144.

Embodiment 153. The method of embodiment 152, wherein the at least one dose is administered in an effective amount to induce an immune response against the fragment antigen in the subject.

Embodiment 154. The method of embodiment 153, wherein the immune response comprises generation of a neutralizing antibody titer against the fragment antigen.

Embodiment 155. The method of embodiment 154, wherein the neutralizing antibody titer is increased by at least 50%, as compared to a neutralizing antibody titer induced by a fragment antigen in the absence of the complement C3d-binding polypeptide from an immunoglobulin-binding protein (Sbi) of *Staphylococcus aureus*.

Embodiment 156. The method of embodiment 154 or 155, wherein the generation of a neutralizing antibody titer has been established in a mouse model using a dose of at least 0.1 μg.

Embodiment 157. The method of any one of embodiments 152 to 156, wherein the at least one dose is administered in an effective amount to stimulate B cells while reducing induction of T cell response.

Embodiment 158. A method comprising administering to a subject:

a) a first dose of the pharmaceutical composition of embodiment 143 or 144; and b) a second dose of the pharmaceutical composition of embodiment 143 or 144.

Embodiment 159. The method of embodiment 158, wherein the first dose and the second dose are administered by at least 3 days, 4 days, 5 days, 6 days, 7 days, 2 weeks, 3 weeks, or 4 weeks apart.

Embodiment 160. The method of embodiment 158 or 159, wherein the first dose and the second dose are in the same amount.

Embodiment 161. The method of embodiment 158 or 159, wherein the first dose and the second dose are in different amounts.

Embodiment 162. A method comprising:

administering to a subject in need thereof a dose of the pharmaceutical composition of embodiment 143 or 144, such that the subject receives:

a first dose of a pharmaceutical composition that delivers a polynucleotide comprising a nucleotide sequence that encodes a target protein antigen or a target protein antigen encoded by the polynucleotide; and a second dose of the pharmaceutical composition of embodiment 143 or 144.

Embodiment 163. The method of embodiment 162, wherein:

(a) the polynucleotide comprising a nucleotide sequence that encodes a target protein antigen further comprises a nucleotide sequence encoding a complement C3d-binding polypeptide from an immunoglobulin-binding protein (Sbi) of *Staphylococcus aureus*; or (b) the target protein antigen encoded by the polynucleotide further comprises a complement C3d-binding polypeptide from an immunoglobulin-binding protein (Sbi) of *Staphylococcus aureus*.

Embodiment 164. The method of embodiment 162 or 163, further comprising, prior to the administering step, administering to the subject the first dose of the pharmaceutical composition that delivers a polynucleotide comprising a nucleotide sequence that encodes a target protein antigen or a target protein antigen encoded by the polynucleotide.

Embodiment 165. A method comprising:

administering to a subject in need thereof a dose of the pharmaceutical composition of embodiment 143 or 144, such that the subject receives:

a first dose of the pharmaceutical composition of embodiment 143 or 144, and a second dose of a pharmaceutical composition that delivers a polynucleotide comprising a nucleotide sequence that encodes a target protein antigen or a target protein antigen encoded by the polynucleotide.

Embodiment 166. The method of embodiment 165, wherein:

(a) the polynucleotide comprising a nucleotide sequence that encodes a target protein antigen further comprises a nucleotide sequence encoding a complement C3d-binding polypeptide from an immunoglobulin-binding protein (Sbi) of *Staphylococcus aureus*; or (b) the target protein antigen encoded by the polynucleotide further comprises a complement C3d-binding polypeptide from an immunoglobulin-binding protein (Sbi) of *Staphylococcus aureus*.

Embodiment 167. A method comprising:

administering to a subject in need thereof a dose of the pharmaceutical composition of embodiment 143 or 144, such that the subject receives:

a first dose of a pharmaceutical composition that delivers a polynucleotide comprising a nucleotide sequence that encodes a fusion polypeptide comprising (i) a target protein antigen and (ii) a complement C3d-binding polypeptide from an immunoglobulin-binding protein (Sbi) of *Staphylococcus aureus*; or a fusion polypeptide encoded by the polynucleotide; and a second dose of the pharmaceutical composition of embodiment 143 or 144.

Embodiment 168. The method of embodiment 167, further comprising, prior to the administering step, administering to the subject the first dose of the pharmaceutical composition that delivers a polynucleotide comprising a nucleotide sequence that encodes a fusion polypeptide comprising (i) a target protein antigen and (ii) a complement C3d-binding polypeptide from an immunoglobulin-binding protein (Sbi) of *Staphylococcus aureus*; or a fusion polypeptide encoded by the polynucleotide.

Embodiment 169. The method of any one of embodiments 162-167, wherein the first dose and the second dose are administered by at least 3 days, 4 days, 5 days, 6 days, 7 days, 2 weeks, 3 weeks, or 4 weeks apart.

Embodiment 170. The method of any one of embodiments 152-159, wherein the subject in need thereof is a subject who is suffering from or is susceptible to a disease, disorder, or condition induced by the target protein antigen.

Embodiment 171. The method of any one of embodiments 152-170, wherein the subject is a mammalian subject.

Embodiment 172. The method of embodiment 171, wherein the subject is a human subject.

Embodiment 173. The method of any one of embodiments 152-172, wherein the administration can be performed by intramuscular administration, intradermal administration, intravenous administration, subcutaneous administration, or combinations thereof.

Embodiment 174. A composition comprising the fusion polypeptide of any one of embodiments 1-96, or the fusion polynucleotide of any one of embodiments 97-137, or the pharmaceutical composition of embodiment 143 or 144, for use in enhancing the immunogenicity of an antigen.

Embodiment 175. A composition comprising the fusion polypeptide of any one of embodiments 1-96, or the fusion polynucleotide of any one of embodiments 97-137, or the pharmaceutical composition of embodiment 143 or 144, for use in stimulating an immune response against an antigen.

Embodiment 176. A composition comprising the fusion polypeptide of any one of embodiments 1-96, or the fusion polynucleotide of any one of embodiments 97-137, or the pharmaceutical composition of embodiment 143 or 144, for use in method of treating a disease or ameliorating a symptom of a disease.

Embodiment 177. A method for enhancing the immunogenicity of an antigen, comprising administering to a subject in need thereof, the fusion polypeptide of any one of embodiments 1-96, or the fusion polynucleotide of any one of embodiments 97-137, or the pharmaceutical composition of embodiment 143 or 144.

Embodiment 178. A method for stimulating an immune response against an antigen, comprising administering to a subject in need thereof, the fusion polypeptide of any one of embodiments 1-96, or the fusion polynucleotide of any one of embodiments 97-137, or the pharmaceutical composition of embodiment 143 or 144.

Embodiment 179. A method of treating a disease or ameliorating a symptom of a disease comprising administering to a subject in need thereof, the fusion polypeptide of any one of embodiments 1-96, or the fusion polynucleotide of any one of embodiments 97-137, or the pharmaceutical composition of embodiment 143 or 144.

Embodiment 180. Use of a composition comprising the fusion polypeptide of any one of embodiments 1-96, or the fusion polynucleotide of any one of embodiments 97-137, or the pharmaceutical composition of embodiment 143 or 144, in the preparation of a medicament for enhancing the immunogenicity of a fragment antigen.

Embodiment 181. Use of a composition comprising the fusion polypeptide of any one of embodiments 1-96, or the fusion polynucleotide of any one of embodiments 97-137, or the pharmaceutical composition of embodiment 143 or 144, in the preparation of a medicament for stimulating an immune response against a antigen.

Embodiment 182. Use of a composition the fusion polypeptide of any one of embodiments 1-96, or the fusion polynucleotide of any one of embodiments 97-137, or the pharmaceutical composition of embodiment 143 or 144, in the preparation of a medicament for treating a disease or ameliorating a symptom of a disease.

Embodiment 183. Use of a composition comprising the fusion polypeptide of any one of embodiments 1-96, or the fusion polynucleotide of any one of embodiments 97-137, or the pharmaceutical composition of embodiment 143 or 144, for enhancing the immunogenicity of a fragment antigen.

Embodiment 184. Use of a composition comprising the fusion polypeptide of any one of embodiments 1-96, or the fusion polynucleotide of any one of embodiments 97-137, or the pharmaceutical composition of embodiment 143 or 144, for stimulating an immune response against a antigen.

Embodiment 185. Use of a composition the fusion polypeptide of any one of embodiments 1-96, or the fusion polynucleotide of any one of embodiments 97-137, or the pharmaceutical composition of embodiment 143 or 144, for treating a disease or ameliorating a symptom of a disease.

Embodiment 186. The composition for use of any one of embodiments 174-176, the method of any one of embodiments 177-179, or the use of any one of embodiments 180-186, wherein the subject is a mammal.

Embodiment 187. The composition for use, method or use of embodiment 186, wherein the subject is a human.

Embodiment 188. The composition for use of any one of embodiments 174-176, the method of any one of embodiments 177-179, or the use of any one of embodiments 180-186, wherein a single dose of the fusion polypeptide, fusion polynucleotide or pharmaceutical composition is administered.

Embodiment 189. The composition for use of any one of embodiments 174-176, the method of any one of embodiments 177-179, or the use of any one of embodiments 180-186, wherein a plurality of doses of the fusion polypeptide, fusion polynucleotide or pharmaceutical composition is administered.

Embodiment 190. The composition for use of any one of embodiments 174-176, the method of any one of embodiments 177-179, or the use of any one of embodiments 180-186, wherein the fusion polypeptide, fusion polynucleotide or pharmaceutical composition is administered at a dose of about 0.5 micrograms to 10 micrograms.

Embodiment 191. The composition for use of any one of embodiments 174-176, the method of any one of embodiments 177-179, or the use of any one of embodiments 180-186, wherein administration of the fusion polynucleotide, fusion polypeptide or pharmaceutical composition results in a humoral response.

Embodiment 192. The composition for use, method or use of embodiment 190, wherein the humoral response is an antibody response.

Embodiment 193. The composition for use of any one of embodiments 174-176, the method of any one of embodiments 177-179, or the use of any one of embodiments 180-186, wherein administration of the fusion polynucleotide, fusion polypeptide or pharmaceutical composition results in an increased titer of an antibody response.

Embodiment 194. The composition for use, method or use of embodiment 193, wherein the increase in titer is an increase of about 10 fold to about 500 fold.

Embodiment 195. The composition for use, method or use of embodiment 193 or 194, wherein the increased titer of the antibody response is compared to administration of an otherwise similar fusion polynucleotide that does not comprise an Sbi domain III, or a fragment or variant thereof; and Sbi domain IV, or a fragment or a variant thereof.

Embodiment 196. The composition for use, method or use of embodiment 193 or 194, wherein the increased titer of the antibody response is compared to administration of an otherwise similar fusion polypeptide that does not comprise an Sbi domain III, or a fragment or variant thereof; and an Sbi domain IV, or a fragment or a variant thereof.

Embodiment 197. The composition for use, method or use of embodiment 193 or 194, wherein the increased titer of the antibody response is compared to administration of an otherwise similar pharmaceutical composition that does not comprise a nucleotide sequence encoding Sbi domain III, or a fragment or variant thereof; and Sbi domain IV, or a fragment or a variant thereof.

Embodiment 198. The composition for use of any one of embodiments 174-176, the method of any one of embodiments 177-179, or the use of any one of embodiments 180-186, wherein the composition is administered via any one of the following routes of administration: intramuscular, intravenous, subcutaneous, intrathecal, intradermal, ocular, intranasal, sublingual, or oral.

Embodiment 199. An in vitro method of selecting a fragment antigen by identifying a polypeptide fragment that folds into a three-dimensional conformation that is substantially identical to the three-dimensional conformation as in a target protein antigen from which the fragment is derived.

Embodiment 200. The method of embodiment 199, wherein the method comprises the steps of:

providing a mammalian cell display system that displays a library of fragment antigen candidates on cell surface;

exposing the mammalian cell display system to a composition comprising antibodies that bind to a target protein antigen from which the fragment antigen candidates are derived;

detecting fragment antigen candidates that bind to the target protein antigen-binding antibodies, wherein the binding of a fragment antigen candidate that binds to at least one of the target protein antigen-binding antibodies is indicative of its likelihood to fold into a three-dimensional conformation that is substantially identical to the three-dimensional conformation as in the target protein antigen.

Embodiment 201. The method of embodiment 198 or 199, wherein the method further comprises a step of generating antibodies that bind to the target protein antigen.

Embodiment 202. The method of embodiment 201, wherein the generation of the antibodies comprises (i) immunizing animals with a target protein antigen or a polynucleotide encoding the same from which the fragment antigen candidates are derived; and (ii) identifying antibodies that bind to the target protein antigen.

Embodiment 203. The method of any one of embodiments 200-202, wherein the mammalian cell display system comprises HEK293T cells, HeLa cells, or CHO cells.

Embodiment 204. The method of any one of embodiments 200-203, wherein the polypeptide fragment is identified based on binding affinity to the antibody in a serum binding assay or a similar assay.

Embodiment 205. A recombinant polynucleotide comprising a nucleotide sequence encoding an immunoglobulin-binding protein (Sbi) of *Staphylococcus aureus*, or a fragment thereof.

Embodiment 206. The polynucleotide of embodiment 205, wherein the polynucleotide comprises a sequence encoding a complement C3d-binding polypeptide from Sbi.

Embodiment 207. The polynucleotide of embodiment 206, wherein the complement C3d-binding polypeptide is or comprises one or both of domain III and domain IV of the Sbi of *Staphylococcus aureus*, or a functional fragment or a variant thereof.

Embodiment 208. The polynucleotide of any one of embodiments 205-207, wherein the polynucleotide is or comprises RNA.

Embodiment 209. The polynucleotide of any one of embodiments 205-207, wherein the polynucleotide is or comprises messenger RNA.

Embodiment 210. The polynucleotide of any one of embodiments 205-207, wherein the polynucleotide is or comprises DNA.

Embodiment 211. The polynucleotide of any one of embodiments 205-210, wherein the polynucleotide encodes a polypeptide which has at least 80%, 85%, 90%, 91%, 92%, 93%, 94%, 95%, 96%, 97%, 98%, 99% or 100% identity to the nucleotide sequence of SEQ ID NO: 9.

Embodiment 212. The polynucleotide of any one of embodiments 205-210, wherein the polynucleotide encodes a polypeptide which has at least 80%, 85%, 90%, 91%, 92%, 93%, 94%, 95%, 96%, 97%, 98%, 99% or 100% identity to the nucleotide sequence of SEQ ID NO: 10.

Embodiment 213. An isolated polypeptide comprising an immunoglobulin-binding protein (Sbi) of *Staphylococcus aureus*.

Embodiment 214. The polypeptide of embodiment 213, comprising a complement C3d-binding polypeptide from Sbi.

Embodiment 215. The polypeptide of embodiment 214, wherein the complement C3d-binding polypeptide is or comprises one or both of domain III and domain IV of the Sbi of *Staphylococcus aureus*, or a functional fragment or a variant thereof.

Embodiment 216. The polypeptide of embodiment 214 or 215, wherein the polypeptide has at least 80%, 85%, 90%, 91%, 92%, 93%, 94%, 95%, 96%, 97%, or 100% identity to the amino acid sequence of SEQ ID NO: 9.

Embodiment 217. The polypeptide of embodiment 214 or 215, wherein the polypeptide has at least 80%, 85%, 90%, 91%, 92%, 93%, 94%, 95%, 96%, 97%, or 100% identity to the amino acid sequence of SEQ ID NO: 10.

Embodiment 218. An expression vector comprising the polynucleotide of any one of embodiments 205-212.

Embodiment 219. A composition for delivering the polypeptide of any one of embodiments 213-217.

Embodiment 220. A composition for delivering the polynucleotide of any one of embodiments 205-212.

Embodiment 221. A pharmaceutical composition that delivers the polynucleotide of any one of embodiments 205-212, the polypeptide of any one of embodiments 213-217, or the expression vector of embodiment 218.

Embodiment 222. The pharmaceutical composition of embodiment 221, further comprising a pharmaceutically acceptable excipient, a diluent, or a combination thereof.

Embodiment 223. A method comprising administering to a subject in need thereof at least one dose of the pharmaceutical composition of embodiment 221 or 222.

Embodiment 224. A method for enhancing the immunogenicity of an antigen, comprising administering to a subject in need thereof, the polynucleotide of any one of embodiments 205-212, the polypeptide of any one of embodiments 213-217, or the pharmaceutical composition of embodiment 221 or 222.

Embodiment 225. A method for stimulating an immune response against an antigen, comprising administering to a subject in need thereof, the polynucleotide of any one of embodiments 205-212, the polypeptide of any one of embodiments 213-217, or the pharmaceutical composition of embodiment 221 or 222.

Embodiment 226. Use of an immunoglobulin-binding protein (Sbi) of *Staphylococcus aureus* as an adjuvant in an immunogenic composition.

Embodiment 227. An immunoglobulin-binding protein (Sbi) of *Staphylococcus aureus* for use as an adjuvant in an immunogenic composition.

What is claimed is:

1. A fusion polynucleotide comprising a nucleotide sequence encoding:

(i) a fragment antigen, an antigen variant, or a fragment antigen variant, that comprises an epitope of a target protein antigen, wherein the target protein antigen is or comprises:

(a) an infectious antigen chosen from a viral antigen or a fungal antigen or combinations thereof; or (b) a cancer antigen; and (ii) a complement C3d-binding polypeptide from an immunoglobulin-binding protein (Sbi) of *Staphylococcus aureus,* wherein the fusion polynucleotide is RNA.

2. The fusion polynucleotide of claim 1, wherein the complement C3d-binding polypeptide is or comprises domain III and domain IV of the Sbi of *Staphylococcus aureus*, or a functional fragment or a variant thereof.

3. The fusion polynucleotide of claim 1, wherein the viral antigen is or comprises an influenza antigen or a coronavirus polypeptide.

4. The fusion polynucleotide of claim 3, wherein the coronavirus polypeptide is or comprises a SARS-CoV 2 protein chosen from: a Spike protein (SARS-CoV-2 S) or fragment thereof; an Envelope protein (SARS-CoV-2 E) or fragment thereof; a Membrane protein (SARS-CoV-2 M) or fragment thereof; a nucleocapsid protein (SARS-CoV-2 N) or fragment thereof; an accessory factor polypeptide or fragment thereof; or any combination thereof.

5. The fusion polynucleotide of claim 1, wherein Mani) and (ii) are contiguous.

6. The fusion polynucleotide of claim 1, wherein the polynucleotide further comprises a nucleotide sequence encoding a secretion peptide.

7. A fusion polynucleotide comprising a nucleotide sequence encoding:

(i) a fragment antigen, an antigen variant, or a fragment antigen variant, that comprises an epitope of a target protein antigen, wherein the target protein antigen is or comprises:

(a) an infectious antigen chosen from a viral antigen or a fungal antigen or combinations thereof; or (b) a cancer antigen; and (ii) a complement C3d-binding polypeptide from an immunoglobulin-binding protein (Sbi) of *Staphylococcus aureus,* wherein the polynucleotide has at least 80% identity to the nucleotide sequence of any one of SEQ ID NOs: 46, 47, 48, 49, 50, 51, 52, 53, or 54.

8. An expression vector comprising the fusion polynucleotide of claim 1.

9. The fusion polynucleotide of claim 1, wherein the polynucleotide encodes an antigen variant or fragment antigen variant which comprises at least one modified amino acid compared to the target protein antigen.

10. The fusion polynucleotide of claim 1, wherein the polynucleotide encodes a fragment antigen which is characterized in that when expressed in vivo, it binds to a Major Histocompatibility Complex (MHC) molecule.

11. The fusion polynucleotide of claim 10, wherein the MHC molecule is or comprises a MHC I molecule.

12. The fusion polynucleotide of claim 1, wherein the fragment antigen is characterized in that when expressed in vivo, it folds into a three-dimensional conformation that is substantially identical to the three-dimensional conformation of the fragment antigen as it is in its native position in the target protein antigen.

13. The fusion polynucleotide of claim 1, wherein the fragment antigen encoded by the polynucleotide has an amino acid sequence length of:

(i) at least 5%, 10%, 20%, 30%, 40%, 50%, 60%, 70%, 80%, 90% or 95% compared to the amino acid sequence length of the target protein antigen;

(ii) no more than 50% of the amino acid sequence length of the target protein antigen;

(iii) about 10-300 amino acid residues; or (iv) a combination thereof.

14. The fusion polynucleotide of claim 1, wherein (i) is positioned N-terminus of (ii).

15. The fusion polynucleotide of claim 7, wherein the polynucleotide is or comprises RNA.

16. A pharmaceutical composition comprising the fusion polynucleotide of claim 1.

17. A cell comprising the fusion polynucleotide of claim 1.

18. The fusion polynucleotide of claim 4, wherein the SARS-CoV-2 protein comprises a RBD domain or a portion thereof.

19. The fusion polynucleotide of claim 18, wherein the SARS-CoV-2 protein encoded by the fusion polynucleotide has at least 80% identity to the sequence of any one of SEQ ID NOs: 3, 4, 5, 6, 7, 20, 21, 22, 23, 24, 25, 26, 27, 28, 29, 30 or 31.

20. The fusion polynucleotide of claim 1, wherein the complement C3d-binding polypeptide encoded by the fusion polynucleotide has at least 80% identity to the sequence of SEQ ID NO: 9 or SEQ ID NO: 10.

21. The fusion polynucleotide of claim 1, wherein the fragment antigen, antigen variant or fragment antigen variant further comprises an amino acid sequence from a second target protein antigen.

22. The fusion polynucleotide of claim 1, wherein (i) is positioned C-terminus of (ii).

23. The fusion polynucleotide of claim 1, wherein (i) and (ii) are separated by a nucleotide sequence encoding a linker.

24. The fusion polynucleotide of claim 10, wherein the MHC molecule is or comprises a MHC II molecule.

25. The fusion polynucleotide of claim 1, wherein the polynucleotide has at least 80% identity to the nucleotide sequence of any one of SEQ ID NOs: 46, 47, 48, 49, 50, 51, 52, 53, or 54.

26. The fusion polynucleotide of claim 1, wherein the complement C3d-binding polypeptide is or comprises domain III of the Sbi of *Staphylococcus aureus*, or a functional fragment or a variant thereof.

27. The fusion polynucleotide of claim 1, wherein the complement C3d-binding polypeptide is or comprises domain IV of the Sbi of *Staphylococcus aureus*, or a functional fragment or a variant thereof.

* * * * *

UNITED STATES PATENT AND TRADEMARK OFFICE

CERTIFICATE OF CORRECTION

PATENT NO. : 11,771,758 B2
APPLICATION NO. : 17/685717
DATED : October 3, 2023
INVENTOR(S) : Kyle Backman et al.

It is certified that error appears in the above-identified patent and that said Letters Patent is hereby corrected as shown below:

On the Title Page

At item (71), please delete "Walnut, CA (US)" and insert --Boston, MA (US)--.

In the Claims

At Column 159, Claim number 5, Line number 9, please delete "Mani)" and insert --(i)--.

Signed and Sealed this
Fifth Day of March, 2024

Katherine Kelly Vidal

Katherine Kelly Vidal
*Director of the United States Patent and Trademark Office*

SEQUENCE LISTING

```
<160> NUMBER OF SEQ ID NOS: 74

<210> SEQ ID NO 1
<211> LENGTH: 20
<212> TYPE: PRT
<213> ORGANISM: Homo sapiens

<400> SEQUENCE: 1

Met Tyr Arg Met Gln Leu Leu Ser Cys Ile Ala Leu Ser Leu Ala Leu
```

```
1               5                   10                  15

Val Thr Asn Ser
            20


<210> SEQ ID NO 2
<211> LENGTH: 13
<212> TYPE: PRT
<213> ORGANISM: Severe acute respiratory syndrome coronavirus 2

<400> SEQUENCE: 2

Met Phe Val Phe Leu Val Leu Leu Pro Leu Val Ser Ser
1               5                   10


<210> SEQ ID NO 3
<211> LENGTH: 197
<212> TYPE: PRT
<213> ORGANISM: Severe acute respiratory syndrome coronavirus 2

<400> SEQUENCE: 3

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro
        195


<210> SEQ ID NO 4
<211> LENGTH: 118
<212> TYPE: PRT
<213> ORGANISM: Severe acute respiratory syndrome coronavirus 2

<400> SEQUENCE: 4

Ile Ala Pro Gly Gln Thr Gly Lys Ile Ala Asp Tyr Asn Tyr Lys Leu
1               5                   10                  15

Pro Asp Asp Phe Thr Gly Cys Val Ile Ala Trp Asn Ser Asn Asn Leu
            20                  25                  30

Asp Ser Lys Val Gly Gly Asn Tyr Asn Tyr Leu Tyr Arg Leu Phe Arg
        35                  40                  45
```

```
Lys Ser Asn Leu Lys Pro Phe Glu Arg Asp Ile Ser Thr Glu Ile Tyr
    50                  55                  60

Gln Ala Gly Ser Thr Pro Cys Asn Gly Val Glu Gly Phe Asn Cys Tyr
65                  70                  75                  80

Phe Pro Leu Gln Ser Tyr Gly Phe Gln Pro Thr Asn Gly Val Gly Tyr
                85                  90                  95

Gln Pro Tyr Arg Val Val Val Leu Ser Phe Glu Leu Leu His Ala Pro
            100                 105                 110

Ala Thr Val Cys Gly Pro
        115


<210> SEQ ID NO 5
<211> LENGTH: 98
<212> TYPE: PRT
<213> ORGANISM: Severe acute respiratory syndrome coronavirus 2

<400> SEQUENCE: 5

Thr Gly Cys Val Ile Ala Trp Asn Ser Asn Asn Leu Asp Ser Lys Val
1               5                   10                  15

Gly Gly Asn Tyr Asn Tyr Leu Tyr Arg Leu Phe Arg Lys Ser Asn Leu
            20                  25                  30

Lys Pro Phe Glu Arg Asp Ile Ser Thr Glu Ile Tyr Gln Ala Gly Ser
        35                  40                  45

Thr Pro Cys Asn Gly Val Glu Gly Phe Asn Cys Tyr Phe Pro Leu Gln
    50                  55                  60

Ser Tyr Gly Phe Gln Pro Thr Asn Gly Val Gly Tyr Gln Pro Tyr Arg
65                  70                  75                  80

Val Val Val Leu Ser Phe Glu Leu Leu His Ala Pro Ala Thr Val Cys
                85                  90                  95

Gly Pro


<210> SEQ ID NO 6
<211> LENGTH: 90
<212> TYPE: PRT
<213> ORGANISM: Severe acute respiratory syndrome coronavirus 2

<400> SEQUENCE: 6

Ser Asn Asn Leu Asp Ser Lys Val Gly Gly Asn Tyr Asn Tyr Leu Tyr
1               5                   10                  15

Arg Leu Phe Arg Lys Ser Asn Leu Lys Pro Phe Glu Arg Asp Ile Ser
            20                  25                  30

Thr Glu Ile Tyr Gln Ala Gly Ser Thr Pro Cys Asn Gly Val Glu Gly
        35                  40                  45

Phe Asn Cys Tyr Phe Pro Leu Gln Ser Tyr Gly Phe Gln Pro Thr Asn
    50                  55                  60

Gly Val Gly Tyr Gln Pro Tyr Arg Val Val Val Leu Ser Phe Glu Leu
65                  70                  75                  80

Leu His Ala Pro Ala Thr Val Cys Gly Pro
                85                  90


<210> SEQ ID NO 7
<211> LENGTH: 48
<212> TYPE: PRT
<213> ORGANISM: Severe acute respiratory syndrome coronavirus 2

<400> SEQUENCE: 7

Cys Asn Gly Val Glu Gly Phe Asn Cys Tyr Phe Pro Leu Gln Ser Tyr
```

-continued

```
1               5                   10                  15

Gly Phe Gln Pro Thr Asn Gly Val Gly Tyr Gln Pro Tyr Arg Val Val
            20                  25                  30

Val Leu Ser Phe Glu Leu Leu His Ala Pro Ala Thr Val Cys Gly Pro
        35                  40                  45


<210> SEQ ID NO 8
<211> LENGTH: 10
<212> TYPE: PRT
<213> ORGANISM: Severe acute respiratory syndrome coronavirus 2

<400> SEQUENCE: 8

Lys Lys Ser Thr Asn Leu Val Lys Asn Lys
1               5                   10


<210> SEQ ID NO 9
<211> LENGTH: 42
<212> TYPE: PRT
<213> ORGANISM: Staphylococcus aureus

<400> SEQUENCE: 9

Ile Glu Asn Ala Asp Lys Ala Ile Lys Asp Phe Gln Asp Asn Lys Ala
1               5                   10                  15

Pro His Asp Lys Ser Ala Ala Tyr Glu Ala Asn Ser Lys Leu Pro Lys
            20                  25                  30

Asp Leu Arg Asp Lys Asn Asn Arg Phe Val
        35                  40


<210> SEQ ID NO 10
<211> LENGTH: 58
<212> TYPE: PRT
<213> ORGANISM: Staphylococcus aureus

<400> SEQUENCE: 10

Glu Lys Val Ser Ile Glu Lys Ala Ile Val Arg His Asp Glu Arg Val
1               5                   10                  15

Lys Ser Ala Asn Asp Ala Ile Ser Lys Leu Asn Glu Lys Asp Ser Ile
            20                  25                  30

Glu Asn Arg Arg Leu Ala Gln Arg Glu Val Asn Lys Ala Pro Met Asp
        35                  40                  45

Val Lys Glu His Leu Gln Lys Gln Leu Asp
    50                  55


<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly Ser Gly Gly Gly Gly Ser
1               5                   10                  15


<210> SEQ ID NO 12
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 12

Met Tyr Arg Met Gln Leu Leu Ser Cys Ile Ala Leu Ser Leu Ala Leu
1               5                   10                  15

Val Thr Asn Ser Ala Ala Asn Ile Thr Asn Leu Cys Pro Phe Gly Glu
            20                  25                  30

Val Phe Asn Ala Thr Arg Phe Ala Ser Val Tyr Ala Trp Asn Arg Lys
        35                  40                  45

Arg Ile Ser Asn Cys Val Ala Asp Tyr Ser Val Leu Tyr Asn Ser Ala
    50                  55                  60

Ser Phe Ser Thr Phe Lys Cys Tyr Gly Val Ser Pro Thr Lys Leu Asn
65                  70                  75                  80

Asp Leu Cys Phe Thr Asn Val Tyr Ala Asp Ser Phe Val Ile Arg Gly
                85                  90                  95

Asp Glu Val Arg Gln Ile Ala Pro Gly Gln Thr Gly Lys Ile Ala Asp
            100                 105                 110

Tyr Asn Tyr Lys Leu Pro Asp Asp Phe Thr Gly Cys Val Ile Ala Trp
        115                 120                 125

Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu
                165                 170                 175

Gly Phe Asn Cys Tyr Phe Pro Leu Gln Ser Tyr Gly Phe Gln Pro Thr
            180                 185                 190

Asn Gly Val Gly Tyr Gln Pro Tyr Arg Val Val Val Leu Ser Phe Glu
        195                 200                 205

Leu Leu His Ala Pro Ala Thr Val Cys Gly Pro Lys Lys Ser Thr Asn
    210                 215                 220

Leu Val Lys Asn Lys
225

<210> SEQ ID NO 13
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Tyr Arg Met Gln Leu Leu Ser Cys Ile Ala Leu Ser Leu Ala Leu
1               5                   10                  15

Val Thr Asn Ser Ala Ala Asn Ile Thr Asn Leu Cys Pro Phe Gly Glu
            20                  25                  30

Val Phe Asn Ala Thr Arg Phe Ala Ser Val Tyr Ala Trp Asn Arg Lys
        35                  40                  45

Arg Ile Ser Asn Cys Val Ala Asp Tyr Ser Val Leu Tyr Asn Ser Ala
    50                  55                  60

Ser Phe Ser Thr Phe Lys Cys Tyr Gly Val Ser Pro Thr Lys Leu Asn
65                  70                  75                  80

Asp Leu Cys Phe Thr Asn Val Tyr Ala Asp Ser Phe Val Ile Arg Gly
                85                  90                  95

Asp Glu Val Arg Gln Ile Ala Pro Gly Gln Thr Gly Lys Ile Ala Asp
            100                 105                 110

```
Tyr Asn Tyr Lys Leu Pro Asp Asp Phe Thr Gly Cys Val Ile Ala Trp
        115                 120                 125

Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu
                165                 170                 175

Gly Phe Asn Cys Tyr Phe Pro Leu Gln Ser Tyr Gly Phe Gln Pro Thr
            180                 185                 190

Asn Gly Val Gly Tyr Gln Pro Tyr Arg Val Val Val Leu Ser Phe Glu
        195                 200                 205

Leu Leu His Ala Pro Ala Thr Val Cys Gly Pro Lys Lys Ser Thr Asn
    210                 215                 220

Leu Val Lys Asn Lys Gly Gly Gly Gly Ser Gly Gly Gly Gly Ser Gly
225                 230                 235                 240

Gly Gly Gly Ser Ile Glu Asn Ala Asp Lys Ala Ile Lys Asp Phe Gln
                245                 250                 255

Asp Asn Lys Ala Pro His Asp Lys Ser Ala Ala Tyr Glu Ala Asn Ser
            260                 265                 270

Lys Leu Pro Lys Asp Leu Arg Asp Lys Asn Asn Arg Phe Val Glu Lys
        275                 280                 285

Val Ser Ile Glu Lys Ala Ile Val Arg His Asp Glu Arg Val Lys Ser
    290                 295                 300

Ala Asn Asp Ala Ile Ser Lys Leu Asn Glu Lys Asp Ser Ile Glu Asn
305                 310                 315                 320

Arg Arg Leu Ala Gln Arg Glu Val Asn Lys Ala Pro Met Asp Val Lys
                325                 330                 335

Glu His Leu Gln Lys Gln Leu Asp
            340
```

<210> SEQ ID NO 14
<211> LENGTH: 327
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Met Phe Val Phe Leu Val Leu Leu Pro Leu Val Ser Ser Ala Ala Asn
1               5                   10                  15

Ile Thr Asn Leu Cys Pro Phe Gly Glu Val Phe Asn Ala Thr Arg Phe
            20                  25                  30

Ala Ser Val Tyr Ala Trp Asn Arg Lys Arg Ile Ser Asn Cys Val Ala
        35                  40                  45

Asp Tyr Ser Val Leu Tyr Asn Ser Ala Ser Phe Ser Thr Phe Lys Cys
    50                  55                  60

Tyr Gly Val Ser Pro Thr Lys Leu Asn Asp Leu Cys Phe Thr Asn Val
65                  70                  75                  80

Tyr Ala Asp Ser Phe Val Ile Arg Gly Asp Glu Val Arg Gln Ile Ala
                85                  90                  95

Pro Gly Gln Thr Gly Lys Ile Ala Asp Tyr Asn Tyr Lys Leu Pro Asp
            100                 105                 110

Asp Phe Thr Gly Cys Val Ile Ala Trp Asn Ser Asn Asn Leu Asp Ser
        115                 120                 125
```

```
Lys Val Gly Gly Asn Tyr Asn Tyr Leu Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
                165                 170                 175

Leu Gln Ser Tyr Gly Phe Gln Pro Thr Asn Gly Val Gly Tyr Gln Pro
            180                 185                 190

Tyr Arg Val Val Val Leu Ser Phe Glu Leu Leu His Ala Pro Ala Thr
        195                 200                 205

Val Cys Gly Pro Gly Gly Gly Gly Ser Gly Gly Gly Gly Ser Gly Gly
    210                 215                 220

Gly Gly Ser Ile Glu Asn Ala Asp Lys Ala Ile Lys Asp Phe Gln Asp
225                 230                 235                 240

Asn Lys Ala Pro His Asp Lys Ser Ala Ala Tyr Glu Ala Asn Ser Lys
                245                 250                 255

Leu Pro Lys Asp Leu Arg Asp Lys Asn Asn Arg Phe Val Glu Lys Val
            260                 265                 270

Ser Ile Glu Lys Ala Ile Val Arg His Asp Glu Arg Val Lys Ser Ala
        275                 280                 285

Asn Asp Ala Ile Ser Lys Leu Asn Glu Lys Asp Ser Ile Glu Asn Arg
    290                 295                 300

Arg Leu Ala Gln Arg Glu Val Asn Lys Ala Pro Met Asp Val Lys Glu
305                 310                 315                 320

His Leu Gln Lys Gln Leu Asp
                325


<210> SEQ ID NO 15
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Tyr Arg Met Gln Leu Leu Ser Cys Ile Ala Leu Ser Leu Ala Leu
1               5                   10                  15

Val Thr Asn Ser Ala Ala Ile Ala Pro Gly Gln Thr Gly Lys Ile Ala
            20                  25                  30

Asp Tyr Asn Tyr Lys Leu Pro Asp Asp Phe Thr Gly Cys Val Ile Ala
        35                  40                  45

Trp Asn Ser Asn Asn Leu Asp Ser Lys Val Gly Gly Asn Tyr Asn Tyr
    50                  55                  60

Leu Tyr Arg Leu Phe Arg Lys Ser Asn Leu Lys Pro Phe Glu Arg Asp
65                  70                  75                  80

Ile Ser Thr Glu Ile Tyr Gln Ala Gly Ser Thr Pro Cys Asn Gly Val
                85                  90                  95

Glu Gly Phe Asn Cys Tyr Phe Pro Leu Gln Ser Tyr Gly Phe Gln Pro
            100                 105                 110

Thr Asn Gly Val Gly Tyr Gln Pro Tyr Arg Val Val Val Leu Ser Phe
        115                 120                 125

Glu Leu Leu His Ala Pro Ala Thr Val Cys Gly Pro Lys Lys Ser Thr
    130                 135                 140

Asn Leu Val Lys Asn Lys Gly Gly Gly Gly Ser Gly Gly Gly Gly Ser
```

```
145                 150                 155                 160

Gly Gly Gly Gly Ser Ile Glu Asn Ala Asp Lys Ala Ile Lys Asp Phe
                165                 170                 175

Gln Asp Asn Lys Ala Pro His Asp Lys Ser Ala Ala Tyr Glu Ala Asn
            180                 185                 190

Ser Lys Leu Pro Lys Asp Leu Arg Asp Lys Asn Asn Arg Phe Val Glu
        195                 200                 205

Lys Val Ser Ile Glu Lys Ala Ile Val Arg His Asp Glu Arg Val Lys
    210                 215                 220

Ser Ala Asn Asp Ala Ile Ser Lys Leu Asn Glu Lys Asp Ser Ile Glu
225                 230                 235                 240

Asn Arg Arg Leu Ala Gln Arg Glu Val Asn Lys Ala Pro Met Asp Val
                245                 250                 255

Lys Glu His Leu Gln Lys Gln Leu Asp
            260                 265


<210> SEQ ID NO 16
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Tyr Arg Met Gln Leu Leu Ser Cys Ile Ala Leu Ser Leu Ala Leu
1               5                   10                  15

Val Thr Asn Ser Ala Ala Thr Gly Cys Val Ile Ala Trp Asn Ser Asn
            20                  25                  30

Asn Leu Asp Ser Lys Val Gly Gly Asn Tyr Asn Tyr Leu Tyr Arg Leu
        35                  40                  45

Phe Arg Lys Ser Asn Leu Lys Pro Phe Glu Arg Asp Ile Ser Thr Glu
    50                  55                  60

Ile Tyr Gln Ala Gly Ser Thr Pro Cys Asn Gly Val Glu Gly Phe Asn
65                  70                  75                  80

Cys Tyr Phe Pro Leu Gln Ser Tyr Gly Phe Gln Pro Thr Asn Gly Val
                85                  90                  95

Gly Tyr Gln Pro Tyr Arg Val Val Val Leu Ser Phe Glu Leu Leu His
            100                 105                 110

Ala Pro Ala Thr Val Cys Gly Pro Lys Lys Ser Thr Asn Leu Val Lys
        115                 120                 125

Asn Lys Gly Gly Gly Gly Ser Gly Gly Gly Gly Ser Gly Gly Gly Gly
    130                 135                 140

Ser Ile Glu Asn Ala Asp Lys Ala Ile Lys Asp Phe Gln Asp Asn Lys
145                 150                 155                 160

Ala Pro His Asp Lys Ser Ala Ala Tyr Glu Ala Asn Ser Lys Leu Pro
                165                 170                 175

Lys Asp Leu Arg Asp Lys Asn Asn Arg Phe Val Glu Lys Val Ser Ile
            180                 185                 190

Glu Lys Ala Ile Val Arg His Asp Glu Arg Val Lys Ser Ala Asn Asp
        195                 200                 205

Ala Ile Ser Lys Leu Asn Glu Lys Asp Ser Ile Glu Asn Arg Arg Leu
    210                 215                 220

Ala Gln Arg Glu Val Asn Lys Ala Pro Met Asp Val Lys Glu His Leu
225                 230                 235                 240
```

Gln Lys Gln Leu Asp
245

<210> SEQ ID NO 17
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Met Tyr Arg Met Gln Leu Leu Ser Cys Ile Ala Leu Ser Leu Ala Leu
1 5 10 15

Val Thr Asn Ser Ala Ala Ser Asn Asn Leu Asp Ser Lys Val Gly Gly
20 25 30

Asn Tyr Asn Tyr Leu Tyr Arg Leu Phe Arg Lys Ser Asn Leu Lys Pro
35 40 45

Phe Glu Arg Asp Ile Ser Thr Glu Ile Tyr Gln Ala Gly Ser Thr Pro
50 55 60

Cys Asn Gly Val Glu Gly Phe Asn Cys Tyr Phe Pro Leu Gln Ser Tyr
65 70 75 80

Gly Phe Gln Pro Thr Asn Gly Val Gly Tyr Gln Pro Tyr Arg Val Val
85 90 95

Val Leu Ser Phe Glu Leu Leu His Ala Pro Ala Thr Val Cys Gly Pro
100 105 110

Lys Lys Ser Thr Asn Leu Val Lys Asn Lys Gly Gly Gly Gly Ser Gly
115 120 125

Gly Gly Gly Ser Gly Gly Gly Gly Ser Ile Glu Asn Ala Asp Lys Ala
130 135 140

Ile Lys Asp Phe Gln Asp Asn Lys Ala Pro His Asp Lys Ser Ala Ala
145 150 155 160

Tyr Glu Ala Asn Ser Lys Leu Pro Lys Asp Leu Arg Asp Lys Asn Asn
165 170 175

Arg Phe Val Glu Lys Val Ser Ile Glu Lys Ala Ile Val Arg His Asp
180 185 190

Glu Arg Val Lys Ser Ala Asn Asp Ala Ile Ser Lys Leu Asn Glu Lys
195 200 205

Asp Ser Ile Glu Asn Arg Arg Leu Ala Gln Arg Glu Val Asn Lys Ala
210 215 220

Pro Met Asp Val Lys Glu His Leu Gln Lys Gln Leu Asp
225 230 235

<210> SEQ ID NO 18
<211> LENGTH: 195
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Met Tyr Arg Met Gln Leu Leu Ser Cys Ile Ala Leu Ser Leu Ala Leu
1 5 10 15

Val Thr Asn Ser Ala Ala Cys Asn Gly Val Glu Gly Phe Asn Cys Tyr
20 25 30

Phe Pro Leu Gln Ser Tyr Gly Phe Gln Pro Thr Asn Gly Val Gly Tyr
35 40 45

-continued

```
Gln Pro Tyr Arg Val Val Val Leu Ser Phe Glu Leu Leu His Ala Pro
    50                  55                  60

Ala Thr Val Cys Gly Pro Lys Lys Ser Thr Asn Leu Val Lys Asn Lys
65                  70                  75                  80

Gly Gly Gly Gly Ser Gly Gly Gly Gly Ser Gly Gly Gly Gly Ser Ile
                85                  90                  95

Glu Asn Ala Asp Lys Ala Ile Lys Asp Phe Gln Asp Asn Lys Ala Pro
            100                 105                 110

His Asp Lys Ser Ala Ala Tyr Glu Ala Asn Ser Lys Leu Pro Lys Asp
        115                 120                 125

Leu Arg Asp Lys Asn Asn Arg Phe Val Glu Lys Val Ser Ile Glu Lys
    130                 135                 140

Ala Ile Val Arg His Asp Glu Arg Val Lys Ser Ala Asn Asp Ala Ile
145                 150                 155                 160

Ser Lys Leu Asn Glu Lys Asp Ser Ile Glu Asn Arg Arg Leu Ala Gln
                165                 170                 175

Arg Glu Val Asn Lys Ala Pro Met Asp Val Lys Glu His Leu Gln Lys
            180                 185                 190

Gln Leu Asp
        195


<210> SEQ ID NO 19
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Tyr Arg Met Gln Leu Leu Ser Cys Ile Ala Leu Ser Leu Ala Leu
1               5                   10                  15

Val Thr Asn Ser Ala Ala Thr Asn Val Tyr Ala Asp Ser Phe Val Ile
            20                  25                  30

Arg Gly Asp Glu Val Arg Gln Ile Ala Pro Gly Gln Thr Gly Lys Ile
        35                  40                  45

Ala Asp Tyr Asn Tyr Lys Leu Pro Asp Asp Phe Thr Gly Cys Val Ile
    50                  55                  60

Ala Trp Asn Ser Asn Asn Leu Asp Ser Lys Val Gly Gly Asn Tyr Asn
65                  70                  75                  80

Tyr Leu Tyr Arg Leu Phe Arg Lys Ser Asn Leu Lys Pro Phe Glu Arg
                85                  90                  95

Asp Ile Ser Thr Glu Ile Tyr Gln Ala Gly Ser Thr Pro Cys Asn Gly
            100                 105                 110

Val Glu Gly Phe Asn Cys Tyr Phe Pro Leu Gln Ser Tyr Gly Phe Gln
        115                 120                 125

Pro Thr Asn Gly Val Gly Tyr Gln Pro Tyr Arg Val Val Val Leu Ser
    130                 135                 140

Phe Glu Leu Lys Lys Ser Thr Asn Leu Val Lys Asn Lys Gly Gly Gly
145                 150                 155                 160

Gly Ser Gly Gly Gly Gly Ser Gly Gly Gly Gly Ser Ile Glu Asn Ala
                165                 170                 175

Asp Lys Ala Ile Lys Asp Phe Gln Asp Asn Lys Ala Pro His Asp Lys
            180                 185                 190

Ser Ala Ala Tyr Glu Ala Asn Ser Lys Leu Pro Lys Asp Leu Arg Asp
        195                 200                 205
```

Lys Asn Asn Arg Phe Val Glu Lys Val Ser Ile Glu Lys Ala Ile Val
    210                 215                 220

Arg His Asp Glu Arg Val Lys Ser Ala Asn Asp Ala Ile Ser Lys Leu
225                 230                 235                 240

Asn Glu Lys Asp Ser Ile Glu Asn Arg Arg Leu Ala Gln Arg Glu Val
                245                 250                 255

Asn Lys Ala Pro Met Asp Val Lys Glu His Leu Gln Lys Gln Leu Asp
            260                 265                 270

<210> SEQ ID NO 20
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Ser Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro
        195

<210> SEQ ID NO 21
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
35 40 45

Cys Tyr Gly Val Ser Pro Thr Lys Leu Asn Asp Leu Cys Phe Thr Asn
50 55 60

Val Tyr Ala Asp Ser Phe Val Ile Arg Gly Asp Glu Val Arg Gln Ile
65 70 75 80

Ala Pro Gly Gln Thr Gly Lys Ile Ala Asp Tyr Asn Tyr Lys Leu Pro
85 90 95

Asp Asp Phe Thr Gly Cys Val Ile Ala Trp Asn Ser Ser Asn Leu Asp
100 105 110

Ser Lys Val Gly Gly Asn Tyr Asn Tyr Leu Tyr Arg Leu Phe Arg Lys
115 120 125

Ser Asn Leu Lys Pro Phe Glu Arg Asp Ile Ser Thr Glu Ile Tyr Gln
130 135 140

Ala Gly Ser Thr Pro Cys Asn Gly Val Glu Gly Phe Asn Cys Tyr Phe
145 150 155 160

Pro Leu Gln Ser Tyr Gly Phe Gln Pro Thr Asn Gly Val Gly Tyr Gln
165 170 175

Pro Tyr Arg Val Val Val Leu Ser Phe Glu Leu Leu His Ala Pro Ala
180 185 190

Thr Val Cys Gly Pro
195

<210> SEQ ID NO 22
<211> LENGTH: 197
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

Asn Ile Thr Asn Leu Cys Pro Phe Gly Glu Val Phe Asn Ala Thr Arg
1 5 10 15

Phe Ala Ser Val Tyr Ala Trp Asn Arg Lys Arg Ile Ser Asn Cys Val
20 25 30

Ala Asp Tyr Ser Val Leu Tyr Asn Ser Ala Ser Phe Ser Thr Phe Lys
35 40 45

Cys Tyr Gly Val Ser Pro Thr Lys Leu Asn Asp Leu Cys Phe Thr Asn
50 55 60

Val Tyr Ala Asp Ser Phe Val Ile Arg Gly Asp Glu Val Arg Gln Ile
65 70 75 80

Ala Pro Gly Gln Thr Gly Lys Ile Ala Asp Tyr Asn Tyr Lys Leu Pro
85 90 95

Asp Asp Phe Thr Gly Cys Val Ile Ala Trp Asn Ser Asn Asn Thr Asp
100 105 110

Ser Lys Val Gly Gly Asn Tyr Asn Tyr Leu Tyr Arg Leu Phe Arg Lys
115 120 125

Ser Asn Leu Lys Pro Phe Glu Arg Asp Ile Ser Thr Glu Ile Tyr Gln
130 135 140

Ala Gly Ser Thr Pro Cys Asn Gly Val Glu Gly Phe Asn Cys Tyr Phe
145 150 155 160

Pro Leu Gln Ser Tyr Gly Phe Gln Pro Thr Asn Gly Val Gly Tyr Gln
165 170 175

Pro Tyr Arg Val Val Val Leu Ser Phe Glu Leu Leu His Ala Pro Ala

```
            180                 185                 190

Thr Val Cys Gly Pro
        195


<210> SEQ ID NO 23
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Ser
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro
        195


<210> SEQ ID NO 24
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
```

```
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Ser Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro
        195


<210> SEQ ID NO 25
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Thr Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro
        195


<210> SEQ ID NO 26
<211> LENGTH: 197
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Ser Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro
        195


<210> SEQ ID NO 27
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110
```

```
Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Thr Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro
        195


<210> SEQ ID NO 28
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Thr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro
        195


<210> SEQ ID NO 29
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

-continued

Asn Ile Thr Asn Leu Cys Pro Phe Gly Glu Val Phe Asn Ala Thr Arg
1 5 10 15

Phe Ala Ser Val Tyr Ala Trp Asn Arg Lys Arg Ile Ser Asn Cys Val
20 25 30

Ala Asp Tyr Ser Val Leu Tyr Asn Ser Ala Ser Phe Ser Thr Phe Lys
35 40 45

Cys Tyr Gly Val Ser Pro Thr Lys Leu Asn Asp Leu Cys Phe Thr Asn
50 55 60

Val Tyr Ala Asp Ser Phe Val Ile Arg Gly Asp Glu Val Arg Gln Ile
65 70 75 80

Ala Pro Gly Gln Thr Gly Lys Ile Ala Asp Tyr Asn Tyr Lys Leu Pro
85 90 95

Asp Asp Phe Thr Gly Cys Val Ile Ala Trp Asn Ser Asn Asn Leu Asp
100 105 110

Ser Lys Val Gly Gly Asn Tyr Asn Tyr Leu Tyr Arg Leu Phe Arg Lys
115 120 125

Ser Asn Leu Lys Pro Phe Glu Arg Asp Ile Ser Thr Glu Ile Tyr Gln
130 135 140

Ala Gly Ser Thr Pro Cys Asn Gly Val Glu Gly Phe Asn Cys Tyr Phe
145 150 155 160

Pro Leu Gln Ser Tyr Gly Phe Gln Pro Thr Asn Gly Thr Gly Tyr Gln
165 170 175

Pro Tyr Arg Val Val Val Leu Ser Phe Glu Leu Leu His Ala Pro Ala
180 185 190

Thr Val Cys Gly Pro
195

<210> SEQ ID NO 30
<211> LENGTH: 197
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Asn Ile Thr Asn Leu Cys Pro Phe Ala Glu Val Phe Asn Ala Thr Arg
1 5 10 15

Phe Ala Ser Val Ala Ala Trp Asn Ala Lys Ala Ile Ser Asn Cys Val
20 25 30

Ala Asp Tyr Ser Val Leu Tyr Asn Ser Ala Ser Phe Ser Thr Phe Lys
35 40 45

Cys Tyr Gly Val Ala Pro Thr Lys Leu Asn Ala Ala Cys Phe Thr Asn
50 55 60

Val Tyr Ala Asp Ser Phe Val Ile Arg Gly Ala Glu Val Arg Gln Ile
65 70 75 80

Ala Pro Gly Gln Thr Gly Lys Ile Ala Asp Tyr Asn Tyr Lys Leu Pro
85 90 95

Asp Asp Phe Thr Gly Cys Val Ile Ala Trp Asn Ser Asn Asn Leu Asp
100 105 110

Ser Lys Val Gly Gly Asn Tyr Asn Tyr Leu Tyr Arg Leu Phe Arg Lys
115 120 125

Ser Asn Leu Lys Pro Phe Glu Arg Asp Ile Ser Thr Glu Ile Tyr Gln
130 135 140

Ala Gly Ser Thr Pro Cys Asn Gly Val Glu Gly Phe Asn Cys Tyr Phe
145 150 155 160

Pro Leu Gln Ser Tyr Gly Phe Gln Pro Thr Asn Gly Val Gly Tyr Gln
165 170 175

Pro Tyr Arg Val Val Val Leu Ser Phe Glu Leu Leu Ala Ala Pro Ala
180 185 190

Thr Val Cys Gly Pro
195

<210> SEQ ID NO 31
<211> LENGTH: 197
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

Asn Ile Thr Asn Leu Cys Ala Phe Gly Glu Val Phe Asn Ala Ala Arg
1 5 10 15

Phe Ala Ser Val Tyr Ala Trp Asn Arg Lys Arg Ile Ser Asn Cys Ala
20 25 30

Ala Ala Tyr Ser Ala Ala Tyr Asn Ser Ala Ser Phe Ser Ala Phe Lys
35 40 45

Cys Ala Gly Val Ala Pro Thr Lys Leu Asn Asp Leu Cys Phe Thr Ala
50 55 60

Val Tyr Ala Asp Ala Phe Ala Ile Arg Ala Ala Ala Val Arg Gln Ala
65 70 75 80

Ala Pro Ala Gln Ala Gly Lys Ile Ala Asp Tyr Asn Tyr Lys Leu Pro
85 90 95

Asp Asp Phe Thr Gly Cys Val Ile Ala Trp Asn Ser Asn Asn Leu Asp
100 105 110

Ser Lys Val Gly Gly Asn Tyr Asn Tyr Leu Tyr Arg Leu Phe Arg Lys
115 120 125

Ser Asn Leu Lys Pro Phe Glu Arg Asp Ile Ser Thr Glu Ile Tyr Gln
130 135 140

Ala Gly Ser Thr Pro Cys Asn Gly Val Glu Gly Phe Asn Cys Tyr Phe
145 150 155 160

Pro Leu Gln Ser Tyr Gly Phe Gln Pro Thr Asn Gly Val Gly Tyr Gln
165 170 175

Pro Tyr Arg Val Val Val Leu Ala Phe Glu Leu Leu His Ala Pro Ala
180 185 190

Thr Ala Cys Gly Pro
195

<210> SEQ ID NO 32
<211> LENGTH: 212
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 32

Met Phe Val Phe Leu Val Leu Leu Pro Leu Val Ser Ser Ala Ala Asn
1 5 10 15

Ile Thr Asn Leu Cys Pro Phe Gly Glu Val Phe Asn Ala Thr Arg Phe
20 25 30

Ala Ser Val Tyr Ala Trp Asn Arg Lys Arg Ile Ser Asn Cys Val Ala
35 40 45

```
Asp Tyr Ser Val Leu Tyr Asn Ser Ala Ser Phe Ser Thr Phe Lys Cys
    50                  55                  60

Tyr Gly Val Ser Pro Thr Lys Leu Asn Asp Leu Cys Phe Thr Asn Val
65                  70                  75                  80

Tyr Ala Asp Ser Phe Val Ile Arg Gly Asp Glu Val Arg Gln Ile Ala
                85                  90                  95

Pro Gly Gln Thr Gly Lys Ile Ala Asp Tyr Asn Tyr Ser Leu Pro Asp
            100                 105                 110

Asp Phe Thr Gly Cys Val Ile Ala Trp Asn Ser Asn Asn Leu Asp Ser
        115                 120                 125

Lys Val Gly Gly Asn Tyr Asn Tyr Leu Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
                165                 170                 175

Leu Gln Ser Tyr Gly Phe Gln Pro Thr Asn Gly Val Gly Tyr Gln Pro
            180                 185                 190

Tyr Arg Val Val Val Leu Ser Phe Glu Leu Leu His Ala Pro Ala Thr
        195                 200                 205

Val Cys Gly Pro
    210
```

<210> SEQ ID NO 33
<211> LENGTH: 212
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Met Phe Val Phe Leu Val Leu Leu Pro Leu Val Ser Ser Ala Ala Asn
1               5                   10                  15

Ile Thr Asn Leu Cys Pro Phe Gly Glu Val Phe Asn Ala Thr Arg Phe
            20                  25                  30

Ala Ser Val Tyr Ala Trp Asn Arg Lys Arg Ile Ser Asn Cys Val Ala
        35                  40                  45

Asp Tyr Ser Val Leu Tyr Asn Ser Ala Ser Phe Ser Thr Phe Lys Cys
    50                  55                  60

Tyr Gly Val Ser Pro Thr Lys Leu Asn Asp Leu Cys Phe Thr Asn Val
65                  70                  75                  80

Tyr Ala Asp Ser Phe Val Ile Arg Gly Asp Glu Val Arg Gln Ile Ala
                85                  90                  95

Pro Gly Gln Thr Gly Lys Ile Ala Asp Tyr Asn Tyr Lys Leu Pro Asp
            100                 105                 110

Asp Phe Thr Gly Cys Val Ile Ala Trp Asn Ser Ser Asn Leu Asp Ser
        115                 120                 125

Lys Val Gly Gly Asn Tyr Asn Tyr Leu Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
                165                 170                 175

Leu Gln Ser Tyr Gly Phe Gln Pro Thr Asn Gly Val Gly Tyr Gln Pro
```

```
            180                 185                 190

Tyr Arg Val Val Val Leu Ser Phe Glu Leu Leu His Ala Pro Ala Thr
        195                 200                 205

Val Cys Gly Pro
    210


<210> SEQ ID NO 34
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Phe Val Phe Leu Val Leu Leu Pro Leu Val Ser Ser Ala Ala Asn
1               5                   10                  15

Ile Thr Asn Leu Cys Pro Phe Gly Glu Val Phe Asn Ala Thr Arg Phe
            20                  25                  30

Ala Ser Val Tyr Ala Trp Asn Arg Lys Arg Ile Ser Asn Cys Val Ala
        35                  40                  45

Asp Tyr Ser Val Leu Tyr Asn Ser Ala Ser Phe Ser Thr Phe Lys Cys
    50                  55                  60

Tyr Gly Val Ser Pro Thr Lys Leu Asn Asp Leu Cys Phe Thr Asn Val
65                  70                  75                  80

Tyr Ala Asp Ser Phe Val Ile Arg Gly Asp Glu Val Arg Gln Ile Ala
                85                  90                  95

Pro Gly Gln Thr Gly Lys Ile Ala Asp Tyr Asn Tyr Lys Leu Pro Asp
            100                 105                 110

Asp Phe Thr Gly Cys Val Ile Ala Trp Asn Ser Asn Asn Thr Asp Ser
        115                 120                 125

Lys Val Gly Gly Asn Tyr Asn Tyr Leu Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
                165                 170                 175

Leu Gln Ser Tyr Gly Phe Gln Pro Thr Asn Gly Val Gly Tyr Gln Pro
            180                 185                 190

Tyr Arg Val Val Val Leu Ser Phe Glu Leu Leu His Ala Pro Ala Thr
        195                 200                 205

Val Cys Gly Pro
    210


<210> SEQ ID NO 35
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Phe Val Phe Leu Val Leu Leu Pro Leu Val Ser Ser Ala Ala Asn
1               5                   10                  15

Ile Thr Asn Leu Cys Pro Phe Gly Glu Val Phe Asn Ala Thr Arg Phe
            20                  25                  30

Ala Ser Val Tyr Ala Trp Asn Arg Lys Arg Ile Ser Asn Cys Val Ala
```

-continued

```
        35                  40                  45

Asp Tyr Ser Val Leu Tyr Asn Ser Ala Ser Phe Ser Thr Phe Lys Cys
    50                  55                  60

Tyr Gly Val Ser Pro Thr Lys Leu Asn Asp Leu Cys Phe Thr Asn Val
65                  70                  75                  80

Tyr Ala Asp Ser Phe Val Ile Arg Gly Asp Glu Val Arg Gln Ile Ala
                85                  90                  95

Pro Gly Gln Thr Gly Lys Ile Ala Asp Tyr Asn Tyr Lys Leu Pro Asp
            100                 105                 110

Asp Phe Thr Gly Cys Val Ile Ala Trp Asn Ser Asn Asn Leu Ser Ser
        115                 120                 125

Lys Val Gly Gly Asn Tyr Asn Tyr Leu Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
                165                 170                 175

Leu Gln Ser Tyr Gly Phe Gln Pro Thr Asn Gly Val Gly Tyr Gln Pro
            180                 185                 190

Tyr Arg Val Val Val Leu Ser Phe Glu Leu Leu His Ala Pro Ala Thr
        195                 200                 205

Val Cys Gly Pro
    210


<210> SEQ ID NO 36
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Phe Val Phe Leu Val Leu Leu Pro Leu Val Ser Ser Ala Ala Asn
1               5                   10                  15

Ile Thr Asn Leu Cys Pro Phe Gly Glu Val Phe Asn Ala Thr Arg Phe
            20                  25                  30

Ala Ser Val Tyr Ala Trp Asn Arg Lys Arg Ile Ser Asn Cys Val Ala
        35                  40                  45

Asp Tyr Ser Val Leu Tyr Asn Ser Ala Ser Phe Ser Thr Phe Lys Cys
    50                  55                  60

Tyr Gly Val Ser Pro Thr Lys Leu Asn Asp Leu Cys Phe Thr Asn Val
65                  70                  75                  80

Tyr Ala Asp Ser Phe Val Ile Arg Gly Asp Glu Val Arg Gln Ile Ala
                85                  90                  95

Pro Gly Gln Thr Gly Lys Ile Ala Asp Tyr Asn Tyr Lys Leu Pro Asp
            100                 105                 110

Asp Phe Thr Gly Cys Val Ile Ala Trp Asn Ser Asn Asn Leu Asp Ser
        115                 120                 125

Lys Val Gly Gly Asn Tyr Ser Tyr Leu Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
                165                 170                 175
```

```
Leu Gln Ser Tyr Gly Phe Gln Pro Thr Asn Gly Val Gly Tyr Gln Pro
            180                 185                 190

Tyr Arg Val Val Val Leu Ser Phe Glu Leu Leu His Ala Pro Ala Thr
        195                 200                 205

Val Cys Gly Pro
    210


<210> SEQ ID NO 37
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Phe Val Phe Leu Val Leu Leu Pro Leu Val Ser Ser Ala Ala Asn
1               5                   10                  15

Ile Thr Asn Leu Cys Pro Phe Gly Glu Val Phe Asn Ala Thr Arg Phe
            20                  25                  30

Ala Ser Val Tyr Ala Trp Asn Arg Lys Arg Ile Ser Asn Cys Val Ala
        35                  40                  45

Asp Tyr Ser Val Leu Tyr Asn Ser Ala Ser Phe Ser Thr Phe Lys Cys
    50                  55                  60

Tyr Gly Val Ser Pro Thr Lys Leu Asn Asp Leu Cys Phe Thr Asn Val
65                  70                  75                  80

Tyr Ala Asp Ser Phe Val Ile Arg Gly Asp Glu Val Arg Gln Ile Ala
                85                  90                  95

Pro Gly Gln Thr Gly Lys Ile Ala Asp Tyr Asn Tyr Lys Leu Pro Asp
            100                 105                 110

Asp Phe Thr Gly Cys Val Ile Ala Trp Asn Ser Asn Asn Leu Asp Ser
        115                 120                 125

Lys Val Gly Gly Asn Tyr Asn Tyr Thr Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
                165                 170                 175

Leu Gln Ser Tyr Gly Phe Gln Pro Thr Asn Gly Val Gly Tyr Gln Pro
            180                 185                 190

Tyr Arg Val Val Val Leu Ser Phe Glu Leu Leu His Ala Pro Ala Thr
        195                 200                 205

Val Cys Gly Pro
    210


<210> SEQ ID NO 38
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Phe Val Phe Leu Val Leu Leu Pro Leu Val Ser Ser Ala Ala Asn
1               5                   10                  15

Ile Thr Asn Leu Cys Pro Phe Gly Glu Val Phe Asn Ala Thr Arg Phe
            20                  25                  30
```

```
Ala Ser Val Tyr Ala Trp Asn Arg Lys Arg Ile Ser Asn Cys Val Ala
        35                  40                  45

Asp Tyr Ser Val Leu Tyr Asn Ser Ala Ser Phe Ser Thr Phe Lys Cys
    50                  55                  60

Tyr Gly Val Ser Pro Thr Lys Leu Asn Asp Leu Cys Phe Thr Asn Val
65                  70                  75                  80

Tyr Ala Asp Ser Phe Val Ile Arg Gly Asp Glu Val Arg Gln Ile Ala
                85                  90                  95

Pro Gly Gln Thr Gly Lys Ile Ala Asp Tyr Asn Tyr Lys Leu Pro Asp
            100                 105                 110

Asp Phe Thr Gly Cys Val Ile Ala Trp Asn Ser Asn Asn Leu Asp Ser
        115                 120                 125

Lys Val Gly Gly Asn Tyr Asn Tyr Leu Tyr Arg Leu Phe Arg Lys Ser
    130                 135                 140

Asn Leu Ser Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
                165                 170                 175

Leu Gln Ser Tyr Gly Phe Gln Pro Thr Asn Gly Val Gly Tyr Gln Pro
            180                 185                 190

Tyr Arg Val Val Val Leu Ser Phe Glu Leu Leu His Ala Pro Ala Thr
        195                 200                 205

Val Cys Gly Pro
    210


<210> SEQ ID NO 39
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Phe Val Phe Leu Val Leu Leu Pro Leu Val Ser Ser Ala Ala Asn
1               5                   10                  15

Ile Thr Asn Leu Cys Pro Phe Gly Glu Val Phe Asn Ala Thr Arg Phe
            20                  25                  30

Ala Ser Val Tyr Ala Trp Asn Arg Lys Arg Ile Ser Asn Cys Val Ala
        35                  40                  45

Asp Tyr Ser Val Leu Tyr Asn Ser Ala Ser Phe Ser Thr Phe Lys Cys
    50                  55                  60

Tyr Gly Val Ser Pro Thr Lys Leu Asn Asp Leu Cys Phe Thr Asn Val
65                  70                  75                  80

Tyr Ala Asp Ser Phe Val Ile Arg Gly Asp Glu Val Arg Gln Ile Ala
                85                  90                  95

Pro Gly Gln Thr Gly Lys Ile Ala Asp Tyr Asn Tyr Lys Leu Pro Asp
            100                 105                 110

Asp Phe Thr Gly Cys Val Ile Ala Trp Asn Ser Asn Asn Leu Asp Ser
        115                 120                 125

Lys Val Gly Gly Asn Tyr Asn Tyr Leu Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Thr Glu Gly Phe Asn Cys Tyr Phe Pro
                165                 170                 175
```

Leu Gln Ser Tyr Gly Phe Gln Pro Thr Asn Gly Val Gly Tyr Gln Pro
180 185 190

Tyr Arg Val Val Val Leu Ser Phe Glu Leu Leu His Ala Pro Ala Thr
195 200 205

Val Cys Gly Pro
210

<210> SEQ ID NO 40
<211> LENGTH: 212
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Met Phe Val Phe Leu Val Leu Leu Pro Leu Val Ser Ser Ala Ala Asn
1 5 10 15

Ile Thr Asn Leu Cys Pro Phe Gly Glu Val Phe Asn Ala Thr Arg Phe
20 25 30

Ala Ser Val Tyr Ala Trp Asn Arg Lys Arg Ile Ser Asn Cys Val Ala
35 40 45

Asp Tyr Ser Val Leu Tyr Asn Ser Ala Ser Phe Ser Thr Phe Lys Cys
50 55 60

Tyr Gly Val Ser Pro Thr Lys Leu Asn Asp Leu Cys Phe Thr Asn Val
65 70 75 80

Tyr Ala Asp Ser Phe Val Ile Arg Gly Asp Glu Val Arg Gln Ile Ala
85 90 95

Pro Gly Gln Thr Gly Lys Ile Ala Asp Tyr Asn Tyr Lys Leu Pro Asp
100 105 110

Asp Phe Thr Gly Cys Val Ile Ala Trp Asn Ser Asn Asn Leu Asp Ser
115 120 125

Lys Val Gly Gly Asn Tyr Asn Tyr Leu Tyr Arg Leu Phe Arg Lys Ser
130 135 140

Asn Leu Lys Pro Phe Glu Arg Asp Ile Ser Thr Glu Ile Tyr Gln Ala
145 150 155 160

Gly Ser Thr Pro Cys Asn Gly Val Glu Gly Phe Asn Cys Thr Phe Pro
165 170 175

Leu Gln Ser Tyr Gly Phe Gln Pro Thr Asn Gly Val Gly Tyr Gln Pro
180 185 190

Tyr Arg Val Val Val Leu Ser Phe Glu Leu Leu His Ala Pro Ala Thr
195 200 205

Val Cys Gly Pro
210

<210> SEQ ID NO 41
<211> LENGTH: 212
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Met Phe Val Phe Leu Val Leu Leu Pro Leu Val Ser Ser Ala Ala Asn
1 5 10 15

Ile Thr Asn Leu Cys Pro Phe Gly Glu Val Phe Asn Ala Thr Arg Phe
20 25 30

```
Ala Ser Val Tyr Ala Trp Asn Arg Lys Arg Ile Ser Asn Cys Val Ala
        35                  40                  45

Asp Tyr Ser Val Leu Tyr Asn Ser Ala Ser Phe Ser Thr Phe Lys Cys
    50                  55                  60

Tyr Gly Val Ser Pro Thr Lys Leu Asn Asp Leu Cys Phe Thr Asn Val
65                  70                  75                  80

Tyr Ala Asp Ser Phe Val Ile Arg Gly Asp Glu Val Arg Gln Ile Ala
                85                  90                  95

Pro Gly Gln Thr Gly Lys Ile Ala Asp Tyr Asn Tyr Lys Leu Pro Asp
            100                 105                 110

Asp Phe Thr Gly Cys Val Ile Ala Trp Asn Ser Asn Asn Leu Asp Ser
        115                 120                 125

Lys Val Gly Gly Asn Tyr Asn Tyr Leu Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
                165                 170                 175

Leu Gln Ser Tyr Gly Phe Gln Pro Thr Asn Gly Thr Gly Tyr Gln Pro
            180                 185                 190

Tyr Arg Val Val Val Leu Ser Phe Glu Leu Leu His Ala Pro Ala Thr
        195                 200                 205

Val Cys Gly Pro
    210


<210> SEQ ID NO 42
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Phe Val Phe Leu Val Leu Leu Pro Leu Val Ser Ser Ala Ala Asn
1               5                   10                  15

Ile Thr Asn Leu Cys Pro Phe Ala Glu Val Phe Asn Ala Thr Arg Phe
            20                  25                  30

Ala Ser Val Ala Ala Trp Asn Ala Lys Ala Ile Ser Asn Cys Val Ala
        35                  40                  45

Asp Tyr Ser Val Leu Tyr Asn Ser Ala Ser Phe Ser Thr Phe Lys Cys
    50                  55                  60

Tyr Gly Val Ala Pro Thr Lys Leu Asn Ala Ala Cys Phe Thr Asn Val
65                  70                  75                  80

Tyr Ala Asp Ser Phe Val Ile Arg Gly Ala Glu Val Arg Gln Ile Ala
                85                  90                  95

Pro Gly Gln Thr Gly Lys Ile Ala Asp Tyr Asn Tyr Lys Leu Pro Asp
            100                 105                 110

Asp Phe Thr Gly Cys Val Ile Ala Trp Asn Ser Asn Asn Leu Asp Ser
        115                 120                 125

Lys Val Gly Gly Asn Tyr Asn Tyr Leu Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
```

```
                165                 170                 175

Leu Gln Ser Tyr Gly Phe Gln Pro Thr Asn Gly Val Gly Tyr Gln Pro
            180                 185                 190

Tyr Arg Val Val Val Leu Ser Phe Glu Leu Leu Ala Ala Pro Ala Thr
        195                 200                 205

Val Cys Gly Pro
    210


<210> SEQ ID NO 43
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Phe Val Phe Leu Val Leu Leu Pro Leu Val Ser Ser Ala Ala Asn
1               5                   10                  15

Ile Thr Asn Leu Cys Ala Phe Gly Glu Val Phe Asn Ala Ala Arg Phe
            20                  25                  30

Ala Ser Val Tyr Ala Trp Asn Arg Lys Arg Ile Ser Asn Cys Ala Ala
        35                  40                  45

Ala Tyr Ser Ala Ala Tyr Asn Ser Ala Ser Phe Ser Ala Phe Lys Cys
    50                  55                  60

Ala Gly Val Ala Pro Thr Lys Leu Asn Asp Leu Cys Phe Thr Ala Val
65                  70                  75                  80

Tyr Ala Asp Ala Phe Ala Ile Arg Ala Ala Ala Val Arg Gln Ala Ala
                85                  90                  95

Pro Ala Gln Ala Gly Lys Ile Ala Asp Tyr Asn Tyr Lys Leu Pro Asp
            100                 105                 110

Asp Phe Thr Gly Cys Val Ile Ala Trp Asn Ser Asn Asn Leu Asp Ser
        115                 120                 125

Lys Val Gly Gly Asn Tyr Asn Tyr Leu Tyr Arg Leu Phe Arg Lys Ser
    130                 135                 140

Asn Leu Lys Pro Phe Glu Arg Asp Ile Ser Thr Glu Ile Tyr Gln Ala
145                 150                 155                 160

Gly Ser Thr Pro Cys Asn Gly Val Glu Gly Phe Asn Cys Tyr Phe Pro
                165                 170                 175

Leu Gln Ser Tyr Gly Phe Gln Pro Thr Asn Gly Val Gly Tyr Gln Pro
            180                 185                 190

Tyr Arg Val Val Val Leu Ala Phe Glu Leu Leu His Ala Pro Ala Thr
        195                 200                 205

Ala Cys Gly Pro
    210


<210> SEQ ID NO 44
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Phe Val Phe Leu Val Leu Leu Pro Leu Val Ser Ser Ala Ala Glu
1               5                   10                  15

Gly Val Glu Cys Asp Phe Ser Pro Leu Leu Ser Gly Thr Pro Pro Gln
```

```
            20                  25                  30

Val Tyr Asn Phe Lys Arg Leu Val Phe Thr Asn Cys Asn Tyr Asn Leu
        35                  40                  45

Thr Lys Leu Leu Ser Leu Phe Ser Val Asn Asp Phe Thr Cys Ser Gln
    50                  55                  60

Ile Ser Pro Ala Ala Ile Ala Ser Asn Cys Tyr Ser Ser Leu Ile Leu
65                  70                  75                  80

Asp Ser Phe Val Ile Arg Gly Asp Glu Val Arg Gln Ile Ala Pro Gly
                85                  90                  95

Gln Thr Gly Lys Ile Ala Asp Tyr Asn Tyr Lys Leu Pro Asp Asp Phe
            100                 105                 110

Thr Gly Cys Val Ile Ala Trp Asn Ser Asn Asn Leu Asp Ser Lys Val
        115                 120                 125

Gly Gly Asn Tyr Asn Tyr Leu Tyr Arg Leu Phe Arg Lys Ser Asn Leu
    130                 135                 140

Lys Pro Phe Glu Arg Asp Ile Ser Thr Glu Ile Tyr Gln Ala Gly Ser
145                 150                 155                 160

Thr Pro Cys Asn Gly Val Glu Gly Phe Asn Cys Tyr Phe Pro Leu Gln
                165                 170                 175

Ser Tyr Gly Phe Gln Pro Thr Asn Gly Val Gly Tyr Gln Pro Tyr Arg
            180                 185                 190

Val Val Val Leu Ser Phe Glu Leu Leu His Ala Pro Ala Thr Val Cys
        195                 200                 205

Pro Lys
    210


<210> SEQ ID NO 45
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Phe Val Phe Leu Val Leu Leu Pro Leu Val Ser Ser Ala Ala Glu
1               5                   10                  15

Gly Val Glu Cys Asp Phe Ser Pro Leu Leu Ser Gly Thr Pro Pro Gln
            20                  25                  30

Val Tyr Asn Phe Lys Arg Leu Val Phe Thr Asn Cys Asn Tyr Asn Leu
        35                  40                  45

Thr Lys Leu Leu Ser Leu Phe Ser Val Asn Asp Phe Thr Cys Ser Gln
    50                  55                  60

Ile Ser Pro Ala Ala Ile Ala Ser Asn Cys Tyr Ser Ser Leu Ile Leu
65                  70                  75                  80

Asp Tyr Phe Ser Tyr Pro Leu Ser Met Lys Ser Asp Leu Ser Val Ser
                85                  90                  95

Ser Ala Gly Pro Ile Ser Gln Phe Asn Tyr Lys Gln Ser Phe Ser Asn
            100                 105                 110

Pro Thr Cys Leu Ile Leu Ala Thr Val Pro His Asn Leu Thr Thr Ile
        115                 120                 125

Thr Lys Pro Leu Lys Tyr Ser Tyr Ile Asn Lys Cys Ser Arg Phe Leu
    130                 135                 140

Ser Asp Asp Arg Thr Glu Val Pro Gln Leu Val Asn Ala Asn Gln Tyr
145                 150                 155                 160
```

-continued

```
Thr Pro Cys Asn Gly Val Glu Gly Phe Asn Cys Tyr Phe Pro Leu Gln
                165                 170                 175

Ser Tyr Gly Phe Gln Pro Thr Asn Gly Val Gly Tyr Gln Pro Tyr Arg
            180                 185                 190

Val Val Val Leu Ser Phe Glu Leu Leu His Ala Pro Ala Thr Val Cys
        195                 200                 205

Pro Lys
    210


<210> SEQ ID NO 46
<211> LENGTH: 874
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

cttgttcttt ttgcagaagc tcagaataaa cgctcaactt tggccaccat gtatcgcatg      60

cagttgctgt cctgtattgc cctgtctctc gcattggtca ctaactctgc cgcaaatatc     120

acaaatctct gccctttcgg ggaggtcttc aacgcaaccc ggttcgcatc agtgtacgcc     180

tggaatcgca aacggatttc taactgtgta gccgattatt ctgtgctgta caacagtgct     240

agtttttcta ccttcaaatg ttatggagta tccccaacca agcttaacga tctttgtttt     300

acaaacgtct acgcagacag ctttgtcatc agggggggacg aagttcgcca aattgctcca     360

gggcagacag gtaaaattgc agactataat tacaaactcc cagacgactt caccggctgt     420

gttatcgctt ggaacagtaa caatcttgac agcaaggtcg gtggcaacta taattatctc     480

tatcgacttt tccgaaaatc caatttgaag ccctttgaga gggacatttc aaccgaaata     540

taccaggctg gatcaactcc ttgcaatggt gtcgaaggat ttaactgtta cttccccttg     600

cagagttacg ggtttcagcc aaccaatggg gtggggtatc aaccataccg ggtcgttgta     660

ttgagtttcg aactgttgca tgctccagca acagtatgtg gtcccaaaaa gagtacaaat     720

ctggtgaaaa acaaataatg atagaccagc ctcaagaaca cccgaatgga gtctctaagc     780

tacataatac caacttacac tttacaaaat gttgtccccc aaaatgtagc cattcgtatc     840

tgctcctaat aaaaagaaag tttcttcaca ttct                                 874


<210> SEQ ID NO 47
<211> LENGTH: 1219
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

cttgttcttt ttgcagaagc tcagaataaa cgctcaactt tggccaccat gtatcgcatg      60

cagttgctgt cctgtattgc cctgtctctc gcattggtca ctaactctgc cgcaaatatc     120

acaaatctct gccctttcgg ggaggtcttc aacgcaaccc ggttcgcatc agtgtacgcc     180

tggaatcgca aacggatttc taactgtgta gccgattatt ctgtgctgta caacagtgct     240

agtttttcta ccttcaaatg ttatggagta tccccaacca agcttaacga tctttgtttt     300

acaaacgtct acgcagacag ctttgtcatc agggggggacg aagttcgcca aattgctcca     360

gggcagacag gtaaaattgc agactataat tacaaactcc cagacgactt caccggctgt     420

gttatcgctt ggaacagtaa caatcttgac agcaaggtcg gtggcaacta taattatctc     480
```

tatcgacttt tccgaaaatc caatttgaag ccctttgaga gggacatttc aaccgaaata 540
taccaggctg gatcaactcc ttgcaatggt gtcgaaggat ttaactgtta cttccccttg 600
cagagttacg ggtttcagcc aaccaatggg gtggggtatc aaccataccg ggtcgttgta 660
ttgagtttcg aactgttgca tgctccagca acagtatgtg gtcccaaaaa gagtacaaat 720
ctggtgaaaa acaaaggtgg gggtggaagt ggtgggggag gctctggcgg aggaggaagc 780
atagagaacg cagataaggc cataaaggat tttcaggata acaaggcccc ccacgacaag 840
tccgccgcat acgaagcaaa ttccaagttg ccaaaggatt tgcgagacaa aaacaatcgc 900
tttgtagaga aagtttcaat tgaaaaagca attgtaaggc atgacgaacg ggtgaagagt 960
gctaacgatg caataagtaa gctgaacgag aaagactcaa ttgagaaccg aaggttggct 1020
caacgcgagg tcaacaaggc accaatggac gtgaaagagc atctgcaaaa gcaacttgac 1080
taatgataga ccagcctcaa gaacacccga atggagtctc taagctacat aataccaact 1140
tacactttac aaaatgttgt cccccaaaat gtagccattc gtatctgctc ctaataaaaa 1200
gaaagtttct tcacattct 1219

<210> SEQ ID NO 48
<211> LENGTH: 823
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 48
cttgttcttt ttgcagaagc tcagaataaa cgctcaactt tggccaccat gttcgtattt 60
ctggtacttc tccccttgt tagttccgca gcaaatatca ccaatctttg ccctttcgga 120
gaggtattca atgcaactcg gtttgcaagt gtgtacgctt ggaatcgcaa gcgcatcagc 180
aattgcgtcg ctgattacag tgtgctctat aacagtgcat ctttctccac tttcaagtgt 240
tacggtgtta gtccaactaa gctgaacgat ctttgtttta ccaacgtgta cgctgattct 300
ttcgtcattc gaggggatga ggtgcgacaa atagcacctg ggcaaaccgg gaaaatagca 360
gactataatt ataagctccc agatgacttc actgggtgcg taattgcctg gaatagcaac 420
aatcttgaca gtaaagtagg gggaaattac aactatttgt acagattgtt tcgcaaatcc 480
aatttgaagc catttgagcg cgacatctct actgagattt atcaggctgg cagcactcct 540
tgtaacggtg tagaaggctt taactgttat ttccccttc aatcttatgg gtttcagccc 600
accaatggcg tgggatacca gccttatcgc gtcgttgtac ttagttttga actgcttcat 660
gctccagcta cagtgtgcgg cccctaatga tagaccagcc tcaagaacac ccgaatggag 720
tctctaagct acataatacc aacttacact ttacaaaatg ttgtccccca aaatgtagcc 780
attcgtatct gctcctaata aaaagaaagt ttcttcacat tct 823

<210> SEQ ID NO 49
<211> LENGTH: 1168
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49
cttgttcttt ttgcagaagc tcagaataaa cgctcaactt tggccaccat gttcgtattt 60
ctggtacttc tccccccttgt tagttccgca gcaaatatca ccaatctttg ccctttcgga 120
gaggtattca atgcaactcg gtttgcaagt gtgtacgctt ggaatcgcaa gcgcatcagc 180
aattgcgtcg ctgattacag tgtgctctat aacagtgcat ctttctccac tttcaagtgt 240
tacggtgtta gtccaactaa gctgaacgat ctttgtttta ccaacgtgta cgctgattct 300
ttcgtcattc gaggggatga ggtgcgacaa atagcacctg ggcaaaccgg gaaaatagca 360
gactataatt ataagctccc agatgacttc actgggtgcg taattgcctg gaatagcaac 420
aatcttgaca gtaaagtagg gggaaattac aactatttgt acagattgtt tcgcaaatcc 480
aatttgaagc catttgagcg cgacatctct actgagattt atcaggctgg cagcactcct 540
tgtaacggtg tagaaggctt taactgttat ttcccccttc aatcttatgg gtttcagccc 600
accaatggcg tgggatacca gccttatcgc gtcgttgtac ttagttttga actgcttcat 660
gctccagcta cagtgtgcgg ccccggtggg ggtggaagtg gtgggggagg ctctggcgga 720
ggaggaagca tagagaacgc agataaggcc ataaaggatt ttcaggataa caaggccccc 780
cacgacaagt ccgccgcata cgaagcaaat tccaagttgc caaaggattt gcgagacaaa 840
aacaatcgct ttgtagagaa agtttcaatt gaaaaagcaa ttgtaaggca tgacgaacgg 900
gtgaagagtg ctaacgatgc aataagtaag ctgaacgaga aagactcaat tgagaaccga 960
aggttggctc aacgcgaggt caacaaggca ccaatggacg tgaaagagca tctgcaaaag 1020
caacttgact aatgatagac cagcctcaag aacacccgaa tggagtctct aagctacata 1080
ataccaactt acactttaca aaatgttgtc ccccaaaatg tagccattcg tatctgctcc 1140
taataaaaag aaagtttctt cacattct 1168

<210> SEQ ID NO 50
<211> LENGTH: 982
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50
cttgttcttt ttgcagaagc tcagaataaa cgctcaactt tggccaccat gtatcgcatg 60
cagttgctgt cctgtattgc cctgtctctc gcattggtca ctaactctgc cgcaattgct 120
ccagggcaga caggtaaaat tgcagactat aattacaaac tcccagacga cttcaccggc 180
tgtgttatcg cttggaacag taacaatctt gacagcaagg tcggtggcaa ctataattat 240
ctctatcgac ttttccgaaa atccaatttg aagccctttg agagggacat ttcaaccgaa 300
atataccagg ctggatcaac tccttgcaat ggtgtcgaag gatttaactg ttacttcccc 360
ttgcagagtt acgggtttca gccaaccaat ggggtggggt atcaaccata ccgggtcgtt 420
gtattgagtt tcgaactgtt gcatgctcca gcaacagtat gtggtcccaa aaagagtaca 480
aatctggtga aaaacaaagg tgggggtgga agtggtgggg gaggctctgg cggaggagga 540
agcatagaga acgcagataa ggccataaag gattttcagg ataacaaggc cccccacgac 600
aagtccgccg catacgaagc aaattccaag ttgccaaagg atttgcgaga caaaaacaat 660
cgctttgtag agaaagtttc aattgaaaaa gcaattgtaa ggcatgacga acgggtgaag 720
agtgctaacg atgcaataag taagctgaac gagaaagact caattgagaa ccgaaggttg 780
gctcaacgcg aggtcaacaa ggcaccaatg gacgtgaaag agcatctgca aaagcaactt 840
gactaatgat agaccagcct caagaacacc cgaatggagt ctctaagcta cataatacca 900

-continued

```
acttacactt tacaaaatgt tgtcccccaa aatgtagcca ttcgtatctg ctcctaataa    960

aaagaaagtt tcttcacatt ct                                              982


<210> SEQ ID NO 51
<211> LENGTH: 922
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

cttgttcttt ttgcagaagc tcagaataaa cgctcaactt tggccaccat gtatcgcatg     60

cagttgctgt cctgtattgc cctgtctctc gcattggtca ctaactctgc cgcaaccggc    120

tgtgttatcg cttggaacag taacaatctt gacagcaagg tcggtggcaa ctataattat    180

ctctatcgac ttttccgaaa atccaatttg aagccctttg agagggacat ttcaaccgaa    240

atataccagg ctggatcaac tccttgcaat ggtgtcgaag gatttaactg ttacttcccc    300

ttgcagagtt acgggtttca gccaaccaat ggggtggggt atcaaccata ccgggtcgtt    360

gtattgagtt tcgaactgtt gcatgctcca gcaacagtat gtggtcccaa aaagagtaca    420

aatctggtga aaaacaaagg tgggggtgga agtggtgggg gaggctctgg cggaggagga    480

agcatagaga acgcagataa ggccataaag gattttcagg ataacaaggc cccccacgac    540

aagtccgccg catacgaagc aaattccaag ttgccaaagg atttgcgaga caaaaacaat    600

cgctttgtag agaaagtttc aattgaaaaa gcaattgtaa ggcatgacga acgggtgaag    660

agtgctaacg atgcaataag taagctgaac gagaaagact caattgagaa ccgaaggttg    720

gctcaacgcg aggtcaacaa ggcaccaatg gacgtgaaag agcatctgca aaagcaactt    780

gactaatgat agaccagcct caagaacacc cgaatggagt ctctaagcta cataatacca    840

acttacactt tacaaaatgt tgtcccccaa aatgtagcca ttcgtatctg ctcctaataa    900

aaagaaagtt tcttcacatt ct                                              922


<210> SEQ ID NO 52
<211> LENGTH: 898
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

cttgttcttt ttgcagaagc tcagaataaa cgctcaactt tggccaccat gtatcgcatg     60

cagttgctgt cctgtattgc cctgtctctc gcattggtca ctaactctgc cgcaagtaac    120

aatcttgaca gcaaggtcgg tggcaactat aattatctct atcgactttt ccgaaaatcc    180

aatttgaagc cctttgagag ggacatttca accgaaatat accaggctgg atcaactcct    240

tgcaatggtg tcgaaggatt taactgttac ttccccttgc agagttacgg gtttcagcca    300

accaatgggg tggggtatca accataccgg gtcgttgtat tgagtttcga actgttgcat    360

gctccagcaa cagtatgtgg tcccaaaaag agtacaaatc tggtgaaaaa caaaggtggg    420

ggtggaagtg gtgggggagg ctctggcgga ggaggaagca tagagaacgc agataaggcc    480

ataaaggatt ttcaggataa caaggccccc cacgacaagt ccgccgcata cgaagcaaat    540

tccaagttgc caaaggattt gcgagacaaa aacaatcgct ttgtagagaa agtttcaatt    600

gaaaaagcaa ttgtaaggca tgacgaacgg gtgaagagtg ctaacgatgc aataagtaag    660
```

-continued

```
ctgaacgaga aagactcaat tgagaaccga aggttggctc aacgcgaggt caacaaggca    720

ccaatggacg tgaaagagca tctgcaaaag caacttgact aatgatagac cagcctcaag    780

aacacccgaa tggagtctct aagctacata ataccaactt acactttaca aaatgttgtc    840

ccccaaaatg tagccattcg tatctgctcc taataaaaag aaagtttctt cacattct      898
```

<210> SEQ ID NO 53
<211> LENGTH: 772
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
cttgttcttt ttgcagaagc tcagaataaa cgctcaactt tggccaccat gtatcgcatg     60

cagttgctgt cctgtattgc cctgtctctc gcattggtca ctaactctgc cgcatgcaat    120

ggtgtcgaag gatttaactg ttacttcccc ttgcagagtt acgggtttca gccaaccaat    180

ggggtggggt atcaaccata ccgggtcgtt gtattgagtt tcgaactgtt gcatgctcca    240

gcaacagtat gtggtcccaa aaagagtaca aatctggtga aaaacaaagg tgggggtgga    300

agtggtgggg gaggctctgg cggaggagga agcatagaga acgcagataa ggccataaag    360

gattttcagg ataacaaggc cccccacgac aagtccgccg catacgaagc aaattccaag    420

ttgccaaagg atttgcgaga caaaaacaat cgctttgtag agaaagtttc aattgaaaaa    480

gcaattgtaa ggcatgacga acgggtgaag agtgctaacg atgcaataag taagctgaac    540

gagaaagact caattgagaa ccgaaggttg gctcaacgcg aggtcaacaa ggcaccaatg    600

gacgtgaaag agcatctgca aaagcaactt gactaatgat agaccagcct caagaacacc    660

cgaatggagt ctctaagcta cataatacca acttacactt tacaaaatgt tgtcccccaa    720

aatgtagcca ttcgtatctg ctcctaataa aaagaaagtt tcttcacatt ct            772
```

<210> SEQ ID NO 54
<211> LENGTH: 973
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
cttgttcttt ttgcagaagc tcagaataaa cgctcaactt tggccaccat gtatcgcatg     60

cagttgctgt cctgtattgc cctgtctctc gcattggtca ctaactctgc cgcaacaaac    120

gtctacgcag acagctttgt catcaggggg gacgaagttc gccaaattgc tccagggcag    180

acaggtaaaa ttgcagacta taattacaaa ctcccagacg acttcaccgg ctgtgttatc    240

gcttggaaca gtaacaatct tgacagcaag gtcggtggca actataatta tctctatcga    300

cttttccgaa aatccaattt gaagcccttt gagagggaca tttcaaccga aatataccag    360

gctggatcaa ctccttgcaa tggtgtcgaa ggatttaact gttacttccc cttgcagagt    420

tacgggtttc agccaaccaa tggggtgggg tatcaaccat accgggtcgt tgtattgagt    480

ttcgaactgg gtgggggtgg aagtggtggg ggaggctctg gcggaggagg aagcatagag    540

aacgcagata aggccataaa ggattttcag gataacaagg ccccccacga caagtccgcc    600

gcatacgaag caaattccaa gttgccaaag gatttgcgag acaaaaacaa tcgctttgta    660
```

gagaaagttt caattgaaaa agcaattgta aggcatgacg aacgggtgaa gagtgctaac 720
gatgcaataa gtaagctgaa cgagaaagac tcaattgaga accgaaggtt ggctcaacgc 780
gaggtcaaca aggcaccaat ggacgtgaaa gagcatctgc aaaagcaact tgactaatga 840
tagaccagcc tcaagaacac ccgaatggag tctctaagct acataatacc aacttacact 900
ttacaaaatg ttgtccccca aaatgtagcc attcgtatct gctcctaata aaaagaaagt 960
ttcttcacat tct 973

<210> SEQ ID NO 55
<211> LENGTH: 149
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
tttttttttt tttttttttt tttttttttt tttttttttt tttttttttt tttttttttt 60
tttttttttt tttttttttt tttttttttt tttttttttt tttttttttt tttttttttt 120
agaatgtgaa gaaactttct ttttattag 149

<210> SEQ ID NO 56
<211> LENGTH: 1311
<212> TYPE: DNA
<213> ORGANISM: Staphylococcus aureus

<400> SEQUENCE: 56
atgaaaaata aatatatctc gaagttgcta gttggggcag caacaattac gttagctaca 60
atgatttcaa atggggaagc aaaagcgagt gaaaacacgc aacaaacttc aactaagcac 120
caaacaactc aaaacaacta cgtaacagat caacaaaaag ctttttatca agtattacat 180
ctaaaaggta tcacagaaga acaacgtaac caatacatca aaacattacg cgaacaccca 240
gaacgtgcac aagaagtatt ctctgaatca cttaaagaca gcaagaaccc agaccgacgt 300
gttgcacaac aaaacgcttt ttacaatgtt cttaaaaatg ataacttaac tgaacaagaa 360
aaaaataatt acattgcaca aattaaagaa aaccctgata gaagccaaca agtttgggta 420
gaatcagtac aatcttctaa agctaaagaa cgtcaaaata ttgaaaatgc ggataaagca 480
attaaagatt tccaagataa caaagcacca cacgataaat cagcagcata tgaagctaac 540
tcaaaattac ctaaagattt acgtgataaa aacaaccgct ttgtagaaaa agtttcaatt 600
gaaaaagcaa tcgttcgtca tgatgagcgt gtgaaatcag caaatgatgc aatctcaaaa 660
ttaaatgaaa aagattcaat tgaaaacaga cgtttagcac aacgtgaagt taacaaagca 720
cctatggatg taaaagagca tttacagaaa caattagacg cattagttgc tcaaaaagat 780
gctgaaaaga aagtggcgcc aaaagttgag gctcctcaaa ttcaatcacc acaaattgaa 840
aaacctaaag tagaatcacc aaaagttgaa gtccctcaaa ttcaatcacc aaaagttgag 900
gttcctcaat ctaaattatt aggttactac caatcattaa aagattcatt taactatggt 960
tacaagtatt taacagatac ttataaaagc tataaagaaa aatatgatac agcaaagtac 1020
tactataata cgtactataa atacaaaggt gcgattgatc aaacagtatt aacagtacta 1080
ggtagtggtt ctaaatctta catccaacca ttgaaagttg atgataaaaa cggctactta 1140
gctaaatcat atgcacaagt aagaaactat gtaactgagt caatcaatac tggtaaagta 1200
ttatatactt tctaccaaaa cccaacatta gtaaaaaacag ctattaaagc tcaagaaact 1260

-continued gcatcatcaa tcaaaaatac attaagtaat ttattatcat tctggaaata a 1311

<210> SEQ ID NO 57
<211> LENGTH: 436
<212> TYPE: PRT
<213> ORGANISM: Staphylococcus aureus

<400> SEQUENCE: 57

```
Met Lys Asn Lys Tyr Ile Ser Lys Leu Leu Val Gly Ala Ala Thr Ile
1               5                   10                  15

Thr Leu Ala Thr Met Ile Ser Asn Gly Glu Ala Lys Ala Ser Glu Asn
            20                  25                  30

Thr Gln Gln Thr Ser Thr Lys His Gln Thr Thr Gln Asn Asn Tyr Val
        35                  40                  45

Thr Asp Gln Gln Lys Ala Phe Tyr Gln Val Leu His Leu Lys Gly Ile
    50                  55                  60

Thr Glu Glu Gln Arg Asn Gln Tyr Ile Lys Thr Leu Arg Glu His Pro
65                  70                  75                  80

Glu Arg Ala Gln Glu Val Phe Ser Glu Ser Leu Lys Asp Ser Lys Asn
                85                  90                  95

Pro Asp Arg Arg Val Ala Gln Gln Asn Ala Phe Tyr Asn Val Leu Lys
            100                 105                 110

Asn Asp Asn Leu Thr Glu Gln Glu Lys Asn Asn Tyr Ile Ala Gln Ile
        115                 120                 125

Lys Glu Asn Pro Asp Arg Ser Gln Gln Val Trp Val Glu Ser Val Gln
    130                 135                 140

Ser Ser Lys Ala Lys Glu Arg Gln Asn Ile Glu Asn Ala Asp Lys Ala
145                 150                 155                 160

Ile Lys Asp Phe Gln Asp Asn Lys Ala Pro His Asp Lys Ser Ala Ala
                165                 170                 175

Tyr Glu Ala Asn Ser Lys Leu Pro Lys Asp Leu Arg Asp Lys Asn Asn
            180                 185                 190

Arg Phe Val Glu Lys Val Ser Ile Glu Lys Ala Ile Val Arg His Asp
        195                 200                 205

Glu Arg Val Lys Ser Ala Asn Asp Ala Ile Ser Lys Leu Asn Glu Lys
    210                 215                 220

Asp Ser Ile Glu Asn Arg Arg Leu Ala Gln Arg Glu Val Asn Lys Ala
225                 230                 235                 240

Pro Met Asp Val Lys Glu His Leu Gln Lys Gln Leu Asp Ala Leu Val
                245                 250                 255

Ala Gln Lys Asp Ala Glu Lys Lys Val Ala Pro Lys Val Glu Ala Pro
            260                 265                 270

Gln Ile Gln Ser Pro Gln Ile Glu Lys Pro Lys Val Glu Ser Pro Lys
        275                 280                 285

Val Glu Val Pro Gln Ile Gln Ser Pro Lys Val Glu Val Pro Gln Ser
    290                 295                 300

Lys Leu Leu Gly Tyr Tyr Gln Ser Leu Lys Asp Ser Phe Asn Tyr Gly
305                 310                 315                 320

Tyr Lys Tyr Leu Thr Asp Thr Tyr Lys Ser Tyr Lys Glu Lys Tyr Asp
                325                 330                 335

Thr Ala Lys Tyr Tyr Tyr Asn Thr Tyr Tyr Lys Tyr Lys Gly Ala Ile
            340                 345                 350

Asp Gln Thr Val Leu Thr Val Leu Gly Ser Gly Ser Lys Ser Tyr Ile
        355                 360                 365
```

```
Gln Pro Leu Lys Val Asp Asp Lys Asn Gly Tyr Leu Ala Lys Ser Tyr
    370                 375                 380

Ala Gln Val Arg Asn Tyr Val Thr Glu Ser Ile Asn Thr Gly Lys Val
385                 390                 395                 400

Leu Tyr Thr Phe Tyr Gln Asn Pro Thr Leu Val Lys Thr Ala Ile Lys
                405                 410                 415

Ala Gln Glu Thr Ala Ser Ser Ile Lys Asn Thr Leu Ser Asn Leu Leu
            420                 425                 430

Ser Phe Trp Lys
        435


<210> SEQ ID NO 58
<211> LENGTH: 1273
<212> TYPE: PRT
<213> ORGANISM: Severe acute respiratory syndrome coronavirus 2

<400> SEQUENCE: 58

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300
```

```
Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720
```

-continued

```
Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
```

-continued

```
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270
```

<210> SEQ ID NO 59
<211> LENGTH: 3822
<212> TYPE: DNA
<213> ORGANISM: Severe acute respiratory syndrome coronavirus 2

<400> SEQUENCE: 59

```
atgtttgttt ttcttgtttt attgccacta gtctctagtc agtgtgttaa tcttacaacc     60

agaactcaat taccccctgc atacactaat tctttcacac gtggtgttta ttaccctgac    120

aaagttttca gatcctcagt tttacattca actcaggact tgttcttacc tttcttttcc    180

aatgttactt ggttccatgc tatacatgtc tctgggacca atggtactaa gaggtttgat    240

aaccctgtcc taccatttaa tgatggtgtt tattttgctt ccactgagaa gtctaacata    300

ataagaggct ggatttttgg tactacttta gattcgaaga cccagtccct acttattgtt    360

aataacgcta ctaatgttgt tattaaagtc tgtgaatttc aattttgtaa tgatccattt    420

ttgggtgttt attaccacaa aaacaacaaa agttggatgg aaagtgagtt cagagtttat    480

tctagtgcga ataattgcac ttttgaatat gtctctcagc cttttcttat ggaccttgaa    540

ggaaaacagg gtaatttcaa aaatcttagg gaatttgtgt ttaagaatat tgatggttat    600

tttaaaatat attctaagca cacgcctatt aatttagtgc gtgatctccc tcagggtttt    660

tcggctttag aaccattggt agatttgcca ataggtatta acatcactag gtttcaaact    720

ttacttgctt tacatagaag ttatttgact cctggtgatt cttcttcagg ttggacagct    780

ggtgctgcag cttattatgt gggttatctt caacctagga cttttctatt aaaatataat    840

gaaaatggaa ccattacaga tgctgtagac tgtgcacttg accctctctc agaaacaaag    900

tgtacgttga aatccttcac tgtagaaaaa ggaatctatc aaacttctaa ctttagagtc    960

caaccaacag aatctattgt tagatttcct aatattacaa acttgtgccc ttttggtgaa   1020

gtttttaacg ccaccagatt tgcatctgtt tatgcttgga acaggaagag aatcagcaac   1080

tgtgttgctg attattctgt cctatataat tccgcatcat tttccacttt taagtgttat   1140

ggagtgtctc ctactaaatt aaatgatctc tgctttacta atgtctatgc agattcattt   1200

gtaattagag gtgatgaagt cagacaaatc gctccagggc aaactggaaa gattgctgat   1260
```

-continued

```
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacaaagt tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac agacaacaca   3360
tttgtgtctg gtaactgtga tgttgtaata ggaattgtca acaacacagt ttatgatcct   3420
ttgcaacctg aattagactc attcaaggag gagttagata aatattttaa gaatcataca   3480
tcaccagatg ttgatttagg tgacatctct ggcattaatg cttcagttgt aaacattcaa   3540
aaagaaattg accgcctcaa tgaggttgcc aagaatttaa atgaatctct catcgatctc   3600
caagaacttg gaaagtatga gcagtatata aaatggccat ggtacatttg gctaggtttt   3660
```

atagctggct tgattgccat agtaatggtg acaattatgc tttgctgtat gaccagttgc 3720
tgtagttgtc tcaagggctg ttgttcttgt ggatcctgct gcaaatttga tgaagacgac 3780
tctgagccag tgctcaaagg agtcaaatta cattacacat aa 3822

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Gly Gly Gly Gly Ser
1 5

<210> SEQ ID NO 61
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: SITE
<222> LOCATION: (1)..(50)
<223> OTHER INFORMATION: This sequence may encompass 1-10 “Gly Gly Gly Gly Ser” repeating units

<400> SEQUENCE: 61

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser
50

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
gaatttaata cgactcacta taaggcttgt tctttttgca gaagc 45

<210> SEQ ID NO 63
<211> LENGTH: 59
<212> TYPE: PRT
<213> ORGANISM: Influenza A virus

<400> SEQUENCE: 63

Ile Val Glu Thr Pro Asn Pro Glu Asn Gly Thr Cys Tyr Pro Gly Tyr
1 5 10 15

Phe Ala Asp Tyr Glu Glu Leu Arg Glu Gln Leu Ser Ser Val Ser Ser
20 25 30

Phe Glu Arg Phe Glu Ile Phe Pro Lys Glu Ser Ser Trp Pro Asn His
35 40 45

```
Thr Val Thr Gly Val Ser Ala Ser Cys Ser His
    50                  55


<210> SEQ ID NO 64
<211> LENGTH: 60
<212> TYPE: PRT
<213> ORGANISM: Influenza A virus

<400> SEQUENCE: 64

Ile Ala Glu Thr Pro Asn Ser Glu Asn Gly Ala Cys Tyr Pro Gly Asp
1               5                   10                  15

Phe Ala Asp Tyr Glu Glu Leu Arg Glu Gln Leu Ser Ser Val Ser Ser
            20                  25                  30

Phe Glu Arg Phe Glu Ile Phe Pro Lys Glu Arg Ser Trp Pro Lys His
        35                  40                  45

Asn Ile Thr Arg Gly Val Thr Ala Ala Cys Ser His
    50                  55                  60


<210> SEQ ID NO 65
<211> LENGTH: 60
<212> TYPE: PRT
<213> ORGANISM: Influenza A virus

<400> SEQUENCE: 65

Ile Ala Glu Thr Pro Asn Ser Glu Asn Gly Thr Cys Tyr Pro Gly Tyr
1               5                   10                  15

Phe Ala Asp Tyr Glu Glu Leu Arg Glu Gln Leu Ser Ser Val Ser Ser
            20                  25                  30

Phe Glu Arg Phe Glu Ile Phe Pro Lys Glu Arg Ser Trp Pro Lys His
        35                  40                  45

Asn Val Thr Arg Gly Val Thr Ala Ser Cys Ser His
    50                  55                  60


<210> SEQ ID NO 66
<211> LENGTH: 59
<212> TYPE: PRT
<213> ORGANISM: Influenza A virus

<400> SEQUENCE: 66

Ile Val Glu Thr Pro Asn Ser Glu Asn Gly Ala Cys Tyr Pro Gly Asp
1               5                   10                  15

Phe Ile Asp Tyr Glu Glu Leu Arg Glu Gln Leu Ser Ser Val Ser Ser
            20                  25                  30

Leu Glu Arg Phe Glu Ile Phe Pro Lys Glu Ser Ser Trp Pro Asn His
        35                  40                  45

Thr Phe Asn Gly Val Thr Val Ser Cys Ser His
    50                  55


<210> SEQ ID NO 67
<211> LENGTH: 60
<212> TYPE: PRT
<213> ORGANISM: Influenza A virus

<400> SEQUENCE: 67

Ile Val Glu Thr Ser Asn Ser Glu Asn Gly Thr Cys Tyr Pro Gly Asp
1               5                   10                  15

Phe Ile Asp Tyr Glu Glu Leu Arg Glu Gln Leu Ser Ser Val Ser Ser
            20                  25                  30

Phe Glu Lys Phe Glu Ile Phe Pro Lys Thr Ser Ser Trp Pro Asn His
        35                  40                  45
```

```
Glu Thr Thr Lys Gly Val Thr Ala Ala Cys Ser Tyr
    50                  55                  60
```

<210> SEQ ID NO 68
<211> LENGTH: 60
<212> TYPE: PRT
<213> ORGANISM: Influenza A virus

<400> SEQUENCE: 68

```
Ile Val Glu Thr Pro Ser Ser Asp Asn Gly Thr Cys Tyr Pro Gly Asp
1               5                   10                  15

Phe Ile Asp Tyr Glu Glu Leu Arg Glu Gln Leu Ser Ser Val Ser Ser
            20                  25                  30

Phe Glu Arg Phe Glu Ile Phe Pro Lys Thr Ser Ser Trp Pro Asn His
        35                  40                  45

Asp Ser Asn Lys Gly Val Thr Ala Ala Cys Pro His
    50                  55                  60
```

<210> SEQ ID NO 69
<211> LENGTH: 60
<212> TYPE: PRT
<213> ORGANISM: Influenza A virus

<400> SEQUENCE: 69

```
Asn Gly Lys Ser Ser Phe Tyr Arg Asn Leu Leu Trp Leu Thr Lys Lys
1               5                   10                  15

Asn Gly Leu Tyr Pro Asn Leu Ser Lys Ser Tyr Val Asn Asn Lys Glu
            20                  25                  30

Lys Glu Val Leu Val Leu Trp Gly Val His His Pro Ser Asn Ile Gly
        35                  40                  45

Asp Gln Arg Thr Ile Tyr His Thr Glu Asn Ala Tyr
    50                  55                  60
```

<210> SEQ ID NO 70
<211> LENGTH: 60
<212> TYPE: PRT
<213> ORGANISM: Influenza A virus

<400> SEQUENCE: 70

```
Ala Gly Lys Ser Ser Phe Tyr Lys Asn Leu Leu Trp Leu Thr Glu Thr
1               5                   10                  15

Asp Gly Ser Tyr Pro Lys Leu Ser Lys Ser Tyr Val Asn Asn Lys Glu
            20                  25                  30

Lys Glu Val Leu Val Leu Trp Gly Val His His Pro Ser Asn Ile Glu
        35                  40                  45

Asp Gln Lys Thr Leu Tyr Arg Lys Glu Asn Ala Tyr
    50                  55                  60
```

<210> SEQ ID NO 71
<211> LENGTH: 60
<212> TYPE: PRT
<213> ORGANISM: Influenza A virus

<400> SEQUENCE: 71

```
Lys Gly Lys Ser Ser Phe Tyr Arg Asn Leu Leu Trp Leu Thr Glu Lys
1               5                   10                  15

Asn Gly Ser Tyr Pro Asn Leu Ser Lys Ser Tyr Val Asn Asn Lys Glu
            20                  25                  30

Lys Glu Val Leu Val Leu Trp Gly Val His His Pro Ser Asn Ile Glu
```

-continued

```
        35                  40                  45

Asp Gln Lys Thr Ile Tyr Arg Lys Glu Asn Ala Tyr
    50                  55                  60


<210> SEQ ID NO 72
<211> LENGTH: 60
<212> TYPE: PRT
<213> ORGANISM: Influenza A virus

<400> SEQUENCE: 72

Arg Gly Lys Ser Ser Phe Tyr Arg Asn Leu Leu Trp Leu Thr Lys Lys
1               5                   10                  15

Gly Asp Ser Tyr Pro Lys Leu Thr Asn Ser Tyr Val Asn Asn Lys Gly
            20                  25                  30

Lys Glu Val Leu Val Leu Trp Gly Val His His Pro Ser Ser Ser Asp
        35                  40                  45

Glu Gln Gln Ser Leu Tyr Ser Asn Gly Asn Ala Tyr
    50                  55                  60


<210> SEQ ID NO 73
<211> LENGTH: 60
<212> TYPE: PRT
<213> ORGANISM: Influenza A virus

<400> SEQUENCE: 73

Ala Gly Ala Ser Ser Phe Tyr Arg Asn Leu Leu Trp Leu Thr Lys Lys
1               5                   10                  15

Gly Ser Ser Tyr Pro Lys Leu Ser Lys Ser Tyr Val Asn Asn Lys Gly
            20                  25                  30

Lys Glu Val Leu Val Leu Trp Gly Val His His Pro Pro Thr Gly Thr
        35                  40                  45

Asp Gln Gln Ser Leu Tyr Gln Asn Ala Asp Ala Tyr
    50                  55                  60


<210> SEQ ID NO 74
<211> LENGTH: 60
<212> TYPE: PRT
<213> ORGANISM: Influenza A virus

<400> SEQUENCE: 74

Ala Gly Ala Lys Ser Phe Tyr Lys Asn Leu Ile Trp Leu Val Lys Lys
1               5                   10                  15

Gly Asn Ser Tyr Pro Lys Leu Ser Lys Ser Tyr Ile Asn Asp Lys Gly
            20                  25                  30

Lys Glu Val Leu Val Leu Trp Gly Ile His His Pro Ser Thr Ser Ala
        35                  40                  45

Asp Gln Gln Ser Leu Tyr Gln Asn Ala Asp Thr Tyr
    50                  55                  60
```